(12) United States Patent
Nuss et al.

(10) Patent No.: US 7,767,669 B2
(45) Date of Patent: Aug. 3, 2010

(54) SMALL MOLECULE PI 3-KINASE INHIBITORS AND METHODS OF THEIR USE

(75) Inventors: John M. Nuss, Danville, CA (US); Sabina Pecchi, Oakland, CA (US); Paul A. Renhowe, Danville, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/188,984

(22) Filed: Aug. 8, 2008

(65) Prior Publication Data

US 2009/0060912 A1 Mar. 5, 2009

Related U.S. Application Data

(63) Continuation of application No. 10/719,896, filed on Nov. 21, 2003, now Pat. No. 7,423,148.

(60) Provisional application No. 60/523,081, filed on Nov. 19, 2003, provisional application No. 60/438,568, filed on Jan. 7, 2003, provisional application No. 60/428,473, filed on Nov. 21, 2002.

(51) Int. Cl.
*C07D 413/14* (2006.01)
*C07D 417/14* (2006.01)
*A61K 31/506* (2006.01)
*A61K 31/5377* (2006.01)
*A61P 35/00* (2006.01)

(52) U.S. Cl. .................... 514/231.5; 544/114; 544/320; 544/321; 544/330; 544/331; 514/269; 514/272; 514/275

(58) Field of Classification Search ................ 544/320, 544/321, 330, 331, 114; 514/272, 275, 269, 514/231.5
See application file for complete search history.

(56) References Cited

U.S. PATENT DOCUMENTS

| 3,975,384 | A | 8/1976 | Narr |
| 4,929,726 | A | 5/1990 | Strekowski |
| 5,786,355 | A | 7/1998 | Konno |
| 5,976,758 | A | 11/1999 | Fukui |
| 5,990,105 | A | 11/1999 | Bös |
| 6,251,900 | B1 | 6/2001 | Kawashima |
| 6,288,228 | B1 | 9/2001 | Henkin |
| 6,495,558 | B1 | 12/2002 | Armistead |
| 6,599,926 | B2 | 7/2003 | Pinto |
| 6,603,000 | B2 | 8/2003 | Yee |
| 6,743,788 | B2 | 6/2004 | Cirillo |
| 6,846,928 | B2 | 1/2005 | Bebbington |
| 2004/0002496 | A1 | 1/2004 | Bebbington |
| 2004/0009974 | A1 | 1/2004 | Bebbington |
| 2004/0009981 | A1 | 1/2004 | Bebbington |
| 2005/0014753 | A1 | 1/2005 | Ding et al. |

FOREIGN PATENT DOCUMENTS

| DE | 2341925 A1 | 3/1975 |
| EP | 0459 830 A1 | 12/1991 |
| EP | 1 277 738 A1 | 1/2003 |
| EP | 1 277 741 A1 | 1/2003 |
| WO | 00/43373 A2 | 7/2000 |
| WO | 01/72745 A1 | 10/2001 |
| WO | 01/83456 A1 | 11/2001 |
| WO | 02/22606 A1 | 3/2002 |
| WO | 02/22608 A1 | 3/2002 |
| WO | 02/36586 A1 | 5/2002 |
| WO | 02/062789 A1 | 8/2002 |
| WO | 02/102313 A2 | 12/2002 |
| WO | 03/030909 A1 | 4/2003 |
| WO | 2004/084824 A2 | 10/2004 |
| WO | 2005/007648 A2 | 1/2005 |
| WO | 2005/009977 A1 | 2/2005 |
| WO | 2005/028444 A1 | 3/2005 |
| WO | 2006/005914 A1 | 1/2006 |

OTHER PUBLICATIONS

Brown, D.M., and G.A.R. Kon, "Some Heterocyclic Analogues of Stilbenes," *Journal of the Chemical Society*, 2147-2153, 1948.

Bundy, G.L., et al., "Synthesis of 2,4-Diaminopyrrolo[2,3-*d*]Pyrimidines Via Thermal Fischer Indolization. Pyrazole Formation With Ytterbium Triflate Catalysis," *Journal of Heterocyclic Chemistry* 37:1471-1477, Nov.-Dec. 2000.

Bundy, G.L., et al., "Synthesis of Novel 2,4-Diaminopyrrolo-[2,3-*d*]Pyrimidines With Antioxidant, Neuroprotective, and Antiasthma Activity," *Journal of Medicinal Chemistry* 38(21):4161-4163, Oct. 1995.

Cabaj, J.E., et al., "Bromine-Mediated Addition of Nucleophiles to the Electron-Rich Pyrimidine Subunit of Tirilazad," *Journal of Organic Chemistry* 59:5090-5092, 1994.

(Continued)

*Primary Examiner*—Venkataraman Balasubramanian

(57) ABSTRACT

Compounds having formula I are provided where the variables have the values described herein.

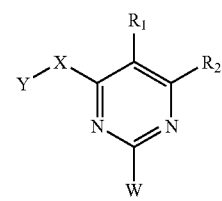

Pharmaceutical formulations include the compounds or pharmaceutically acceptable salts thereof and a pharmaceutically acceptable carrier and combinations with other agents. A method of treating a patient comprises administering a pharmaceutical formulation according to the invention to a patient in need thereof.

13 Claims, No Drawings

OTHER PUBLICATIONS

Crowder, R.J., and M.J. Ellis, "Treating Breast Cancer Through Novel Inhibitors of the Phosphatidylinositol 3'-Kinase Pathway," *Breast Cancer Research* 7(5):212-214, Oct. 2005.

Falco, E.A., et al., "2 : 4-Diaminopyrimidines—A New Series of Antimalarials," *British Journal of Pharmacology and Chemotherapy* 6:185-200, 1951.

Font, D., et al., Development of an Efficient and Straightforward Methodology Toward the Synthesis of Molecularly Diverse 2,6-Disubstituted 3,4-Dihydropyrimidin-4(3*H*)-ones,: *Synthesis* 13:1833-1842, Sep. 2002.

Kowalewski, A., et al., "Unfused Heterobicycles as Amplifiers of Phleomycin. IV 4,5'-Bipyrimidines with Dimethylamino and/or Dimethylaminoethylamino Substituents," *Australian Journal of Chemistry* 34(12):2929-2933, 1981.

Li, S.Y., et al., "*PIK3CA* Mutations in Breast Cancer Are Associated With Poor Outcome," *Breast Cancer Research and Treatment* 96(1):91-95, Mar. 2006.

Mokrosz, M.J., et al., "Structure-Activity Relationship Studies of CNS Agents, Part 25: 4,6-Di(hyteroarly)-2-(N-methylpiperazino)pyrimidines as New, Potent 5-HT2A Receptor Ligands: A Verification of the Topographic Model," *Archiv der Pharmazie* 328(9):659-666, 1995.

Nahta, R., et al., "Signal Transduction Inhibitors in the Treatment of Breast Cancer," *Current Medicinal Chemistry—Anti-Cancer Agents* 3(3):201-216, May 2003.

Ouf, A.A.A., et al., "Preparation of Some Methyl Pyrimidines Expected to be Antimetabolites," *Egyptian Journal of Pharmaceutical Science* 14(2):180-195, 1973.

Andrisano, R., "Pyrimidine. IV," Bollettino Scientifico della Facolta di Chimica Industriale di Bologna 5:48-51, 1947. Volume Date 1944-1947. CA 44:19897, 1950 (1 page).

Balant, L.P., and E. Doelker, "Metabolic Considerations in Prodrug Design," in M.E. Wolff (ed.), "Burger's Medicinal Chemistry and Drug Discovery," vol. 1, "Principles and Practice," 5th ed., Wiley, New York, 1995, pp. 975-977.

Banker, G.S., and C.T. Rhodes (eds.), "Modern Pharmaceutics," 3rd ed., Marcel Dekker, New York, 1996, pp. 451 and 596.

Bennet, J.C., and F. Plum (eds.), "Cecil Textbook of Medicine," 20th ed., W.B. Saunders, Philadelphia, 1996, Part XIV, "Oncology," pp. 1004-1101.

Caine, G.J., et al., "Coagulopathic Complications in Breast Cancer," *Cancer* 98(8):1578-1586, Oct. 2003.

Kothari, S., et al., "A Facile One Pot Conversion of 3',5'-Dibromo-4'-hydroxy Substituted Chalcones to Pyrimidine Derivatives and Their Antibacterial and Herbicidal Activity," Indian Journal of Heterocyclic Chemistry 8(4):285-288, 1999. CA 131:257520, 1999 (3 pages).

Mamaev, V.P., et al., "Reaction Kinetics of Substituted 2-Chloropyrimidines With Piperidine," Reaktsionnaya Sposobnost Organicheskikh Soedinenii 5(3):824-837, 1968. CA 70:76976, 1969 (1 page).

Mikhaleva, M.A., et al., "Pyrimidines. 70. Relative Reactivity of the Chlorine Atoms of 2,2',4-Trichloro-4',5-bipyrimidine in the Reaction With Piperidine," Khimiya Geterotsiklicheskikh Soedinenii 6:821-826, 1979. CA 91:107951, 1979 (1 page).

Sharma, P., et al., "A Convenient One-Pot Synthesis of 2-Substituted-4,6-diaryl Pyrimidines," Indian Journal of Chemistry 38B:966-968, Aug. 1999.

Sukhwal, S., et al., "A New Route to 2-Piperidino-4,6-diarylpyrimidines," Indian Journal of Heterocyclic Chemistry 4(1):67-68, 1994. CA 122:105796, 1995 (2 pages).

Tani, H., et al., "2,4,6-Trisubstituted Pyrimidines," JP 49021148, May 30, 1974. CA 82:140173, 1975 (2 pages).

SMALL MOLECULE PI 3-KINASE INHIBITORS AND METHODS OF THEIR USE

CROSS-REFERENCES TO RELATED APPLICATIONS

This application is a continuation of U.S. patent application Ser. No. 10/719,896, filed Nov. 21, 2003, now U.S. Pat. No. 7,423,148, which claims the benefit of U.S. Provisional Application No. 60/428,473, filed Nov. 21, 2002, U.S. Provisional Application No. 60/438,568, filed Jan. 7, 2003, and U.S. Provisional Application No. 60/523,081, filed Nov. 19, 2003, priority of the filing dates of which is hereby claimed under 35 U.S.C. §§120 and 119, respectively. Each of these applications is incorporated herein.

FIELD OF THE INVENTION

This invention pertains generally to the treatment of diseases, such as cancer, characterized by the abnormal activity of growth factors, protein serine/threonine kinases, and phospholipid kinases. In other aspects, the present invention provides small molecule inhibitors of phosphotidylinositol (PI) 3-kinase, pharmaceutical formulations containing such inhibitors, methods of treating patients with such pharmaceutical formulations, and to methods of preparing such pharmaceutical formulations and inhibitors.

BACKGROUND OF THE INVENTION

Phosphotidylinositol 3-kinase (PI3K) is both a phospholipid kinase, and a protein serine/threonine kinase as described in Carpenter et al., *Mol. Cell. Biol.* 13:1657-1665 (1993). PI3K is an enzyme stimulated by growth factors that is responsible for phosphorylating phosphotidylinositol (PI) at the D-3' position of the inositol ring as described in Whitman et al., *Nature* 332:644-646 (1988). PI3K association with Src-like or receptor tyrosine kinases also implicates PI3K in the oncogenic or mitogenic responses induced by these protein kinases, as described in Cantley et al., *Cell* 64:281-302 (1991), Escobedo and Williams, *Nature* 335:85-87 (1988), and Fantl et al., *Cell* 69:413-423 (1992).

Previously, studies to elucidate the downstream effects of PI 3-kinase activation have been conducted with receptor mutants constructed to alter the signal transduction of PI3K, or by constructing mutant oncogenes to study a PI3K inducible oncogenic response. The failure of receptor mutants of platelet derived growth factor (PDGF) receptor to activate PI3K has been correlated with deficiency of the receptor mutants in triggering a mitogenic response. Similarly, mutants of certain oncogenes have failed to trigger the oncogenic transformation inducible by the parent oncogene. A method was subsequently constructed to facilitate downstream effects of PI3K directly, without growth factor activation to determine whether PI3K was distinctly involved oncogenesis and mitogenesis. The results elucidated that PI3K can be directly or indirectly responsible for many cellular processes, such as mitogenesis and oncogenesis, as well as histamine secretion, neutrophil activation, platelet activation, cell migration, glucose transport, antilipolysis, and vesicle sorting.

With the many regulatory responses associated with PI3-kinase, which is known to be involved in signal cascades involving other well known oncogenic proteins, such as receptor tyrosine kinases (e.g., VEGF-RTK), it would be highly desirable to produce small molecules capable of modulating, e.g. inhibiting, the activity of PI3-kinase.

It is an object of this invention to provide potent inhibitors of PI3K. It is further an object of the instant invention to provide compounds alone or in combination with other known agents to modulate cellular proliferation in patients in need thereof. Additionally, it is an object of this invention to provide medicaments for use in the treatment cancer.

SUMMARY OF THE INVENTION

The present invention provides novel pyrimidine based compounds, pharmaceutical formulations comprising the compounds, methods of inhibiting phosphotidylinositol 3-kinase (PI3K), and methods of treating cancer.

In one aspect, the present invention provides compounds of formula (I):

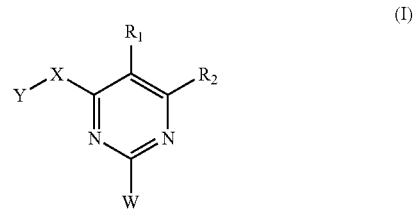

its stereoisomers, tautomers, pharmaceutically acceptable salts, esters, and prodrugs, wherein
Y is selected from the groups consisting of
(1) substituted or unsubstituted $C_1$-$C_6$-alkyl,
(2) substituted or unsubstituted $C_2$-$C_6$-alkenyl,
(3) substituted or unsubstituted $C_2$-$C_6$-alkynyl,
(4) substituted or unsubstituted aryl,
(5) substituted or unsubstituted heterocyclyl, and
(6) substituted or unsubstituted heteroaryl;
X is selected from the group consisting of
(1) a direct link,
(2) —N($R^{1x}$)—,
(3) —($CH_2$)$_m$—C($R^{2x}$,$R^{3x}$)—N($R^{1x}$)—,
(4) —O—,
(5) —S—,
(6) —SO—,
(7) —$SO_2$—,
(8) —C($R^{2x}$,$R^{3x}$)—, and
(9)

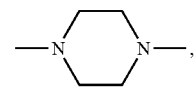

wherein $R^{1x}$, $R^{2x}$, and $R^{3x}$ are selected from the group consisting of
(a) H,
(b) substituted or unsubstituted $C_1$-$C_6$-alkyl,
(c) substituted or unsubstituted $C_2$-$C_6$-alkenyl,
(d) substituted or unsubstituted $C_2$-$C_6$-alkynyl,
(e) substituted or unsubstituted aryl,
(f) substituted or unsubstituted heterocyclyl,
(g) substituted or unsubstituted heteroaryl; and
m is 0, 1, 2, 3, or 4;
$R_1$ is selected from the group consisting of
(1) H,
(2) substituted or unsubstituted $C_1$-$C_6$-alkyl,
(3) —COOH,
(4) halo, (5) —OR$^{1t}$, and
(6) —NHR$^{1t}$,
  wherein R$^{1t}$ is H or C$_1$-C$_6$-alkyl;
R$_2$ is selected from the group consisting of
(1) substituted or unsubstituted aryl,
(2) substituted or unsubstituted heteroaryl, and
(3) substituted or unsubstituted heterocyclyl; and
W is selected from the group consisting of
(1) substituted or unsubstituted C$_1$-C$_6$-alkyl,
(2) —N(R$^{1w}$,R$^{2w}$), and
(3)

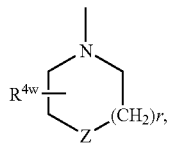

wherein R$^{1w}$ and R$^{2w}$ are selected from the group consisting of
(a) H,
(b) substituted or unsubstituted C$_1$-C$_6$-alkyl,
(c) substituted or unsubstituted aryl,
(d) substituted or unsubstituted heterocyclyl, and
(e) substituted or unsubstituted heteroaryl, wherein R$^{1w}$ and R$^{2w}$ are not both H;
Z is selected from the group consisting of
(a) —O—,
(b) —NR$^z$—,
(c) —S—,
(d) —SO—,
(e) —SO$_2$—, and
(f) —CH$_2$—,
  wherein R$^z$ is H or substituted or unsubstituted alkyl group; and
R$^{4w}$ is selected from the group consisting of
(a) H,
(b) substituted or unsubstituted C$_1$-C$_6$-alkyl,
(c) —COOR$^{5w}$,
(d) —CONH$_2$,
(e) —OR$^{5w}$, and
(f) —NHR$^{5w}$,
  wherein R$^{5w}$ is H or C$_1$-C$_6$-alkyl; and r is 0, 1, or 2;
with the proviso that when X is O, then Y is substituted or unsubstituted aryl, substituted or unsubstituted heterocyclyl, or substituted or unsubstituted heteroaryl;

with the proviso that when W is morpholino, thiomorpholino, 1-oxido-thiomorpholino, 1,1-dioxido morpholino, piperazino, or N-substituted piperazino, R$_2$ is morpholino, thiomorpholino, 1-oxido-thiomorpholino, 1,1-dioxido-thiomorpholino, piperazino, or N'-[acetyl(alkanoyl of 1 to 3 carbon atoms)]piperazino, and X is NH, then Y is not hydrogen, alkyl of 1 to 3 carbon atoms, cyclohexyl, phenyl, chlorophenyl, carboxy-phenyl, carbomethoxy-phenyl, or pyridyl;

with the proviso that when W is morpholino, thiomorpholino, 1-oxido-thiomorpholino, 1,1-dioxido morpholino, piperazino, or N-substituted piperazino, R$_2$ is morpholino, thiomorpholino, 1-oxido-thiomorpholino, 1,1-dioxido-thiomorpholino, piperazino, or N'-[acetyl(alkanoyl of 1 to 3 carbon atoms)]piperazino, and X is a direct link, then Y is not phenyl, substituted or unsubstituted C1-C6-alkyl, or 1-oxidothiomorpholino; and with the proviso that when R$_2$ is phenyl independently substituted with one to five substituents selected from hydrogen, cycloalkyl, heterocycloalkyl, halo, nitro, amino, sulphonamido, or alkylsulphonylamino, R$_1$ is hydrogen, haloalkyl, alkyl, or halo, and X is NR$^{1x}$, then Y is substituted or unsubstituted heteroaryl or substituted or unsubstituted heterocyclyl.

In one embodiment, the invention provides compounds of formula (I), wherein
Y is selected from the group consisting of
(1) substituted or unsubstituted C$_1$-C$_6$-alkyl,
(2) substituted or unsubstituted aryl,
(3) substituted or unsubstituted heterocyclyl, and
(4) substituted or unsubstituted heteroaryl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

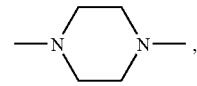

wherein R$^{1x}$, R$^{2x}$, R$^{3x}$ are independently H or substituted or unsubstituted C$_1$-C$_6$-alkyl; and
W is selected from the group consisting of

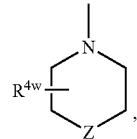

wherein Z is —O— or —NR$^z$—, wherein R$^{4w}$ is H or substituted or unsubstituted C$_1$-C$_6$-alkyl.

In another embodiment, the invention provides compounds of formula (I), wherein
Y is selected from the groups consisting of
(1) substituted or unsubstituted heterocyclyl,
(2) substituted or unsubstituted heteroaryl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

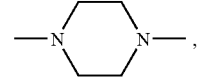

wherein R$^{1x}$, R$^{2x}$, R$^{3x}$ are independently H or substituted or unsubstituted C$_1$-C$_6$-alkyl; and
W is selected from the group consisting of

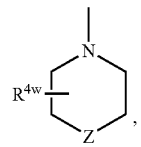

wherein Z is —O— or —NR$^z$—, wherein R$^{4w}$ is H or substituted or unsubstituted C$_1$-C$_6$-alkyl.

In another embodiment, the invention provides compounds of formula (I), wherein
Y is substituted or unsubstituted aryl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

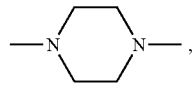

wherein R$^{1x}$, R$^{2x}$, R$^{3x}$ are independently H or substituted or unsubstituted C$_1$-C$_6$-alkyl; and
W is selected from the group consisting of

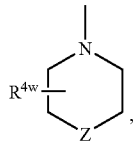

wherein Z is —O— or —NR$^z$—, wherein R$^{4w}$ is H or substituted or unsubstituted C$_1$-C$_6$-alkyl.

In another embodiment, the invention provides compounds of formula (I), wherein
Y is substituted or unsubstituted alkyl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

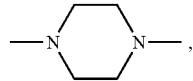

wherein R$^{1x}$, R$^{2x}$, R$^{3x}$ are independently H or substituted or unsubstituted C$_1$-C$_6$-alkyl; and
W is selected from the group consisting of

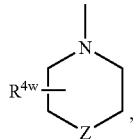

wherein Z is —O— or —NR$^z$—, wherein R$^{4w}$ is H or substituted or unsubstituted C$_1$-C$_6$-alkyl.

In another embodiment, the invention provides compounds of formula (I), wherein
Y is selected from the group consisting of
(1) substituted or unsubstituted heterocyclyl,
(2) substituted or unsubstituted heteroaryl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

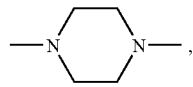

wherein R$^{1x}$, R$^{2x}$, R$^{3x}$ are independently H or substituted or unsubstituted C$_1$-C$_6$-alkyl;
R$_2$ is substituted or unsubstituted aryl; and
W is

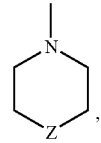

wherein Z is —O— or —NH—.

In another embodiment, the invention provides compounds of formula (I), wherein
Y is substituted or unsubstituted aryl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

wherein R$^{1x}$, R$^{2x}$, R$^{3x}$ are independently H or substituted or unsubstituted C$_1$-C$_6$-alkyl;
R$_2$ is substituted or unsubstituted aryl; and
W is

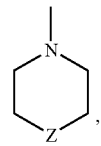

wherein Z is —O— or —NH—.

In another embodiment, the invention provides compounds of formula (I), wherein
Y is substituted or unsubstituted alkyl;
X is selected from the group consisting of
(1) a direct link,
(2) —N(R$^{1x}$)—,
(3) —(CH$_2$)$_m$—C(R$^{2x}$,R$^{3x}$)—N(R$^{1x}$)—, and
(4)

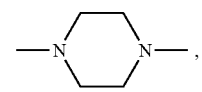

wherein R$^{1x}$, R$^{2x}$, R$^{3x}$ are independently H or substituted or unsubstituted C$_1$-C$_6$-alkyl;
R$_2$ is substituted or unsubstituted aryl; and
W is

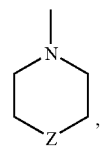

wherein Z is —O— or —NH—.

In another embodiment, the invention provides compounds of formula (I) having structure (II):

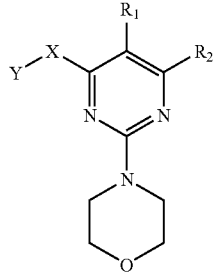

wherein Y is selected from the group consisting of
(1) substituted or unsubstituted $C_1$-$C_6$-alkyl,
(2) substituted or unsubstituted aryl,
(3) substituted or unsubstituted heterocyclyl, and
(4) substituted or unsubstituted heteroaryl; and
X is selected from the group consisting of
(1) a direct link,
(2) —N($R^{1x}$)—,
(3) —(CH$_2$)$_m$—C($R^{2x}$,$R^{3x}$)—N($R^{1x}$)—, and
(4)

In another embodiment, the invention provides compounds of formula (I) having structure (II), wherein Y and X, taken together, are selected from the group consisting of

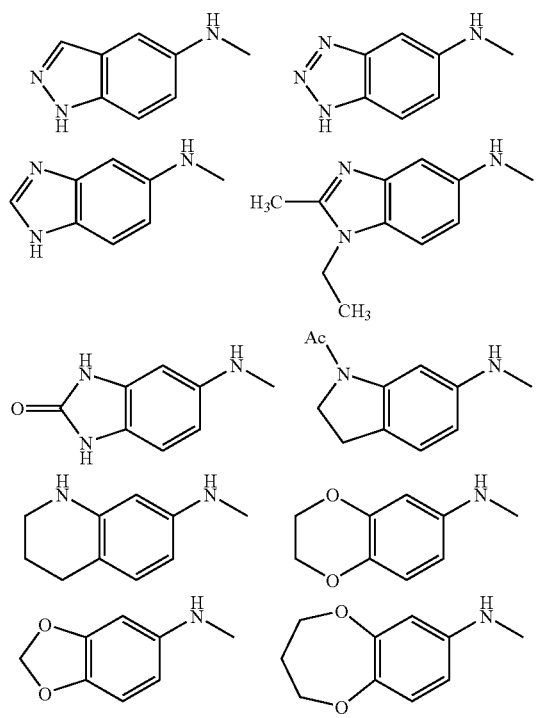

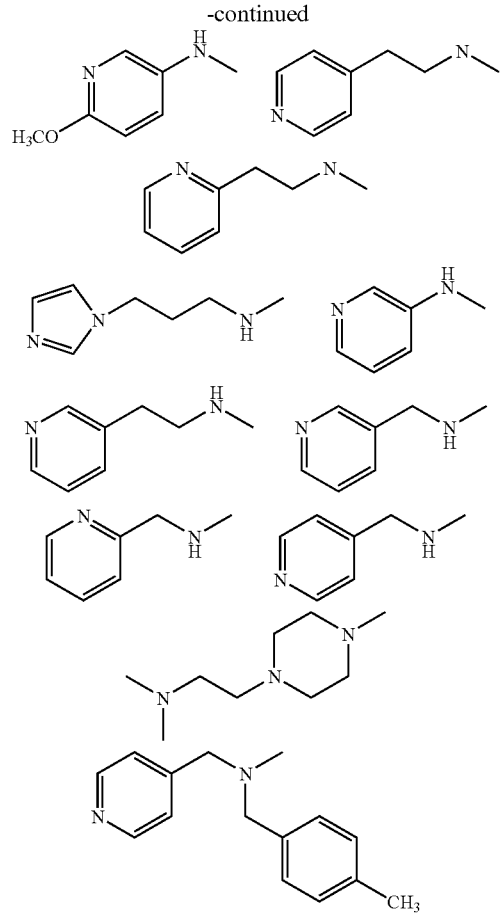

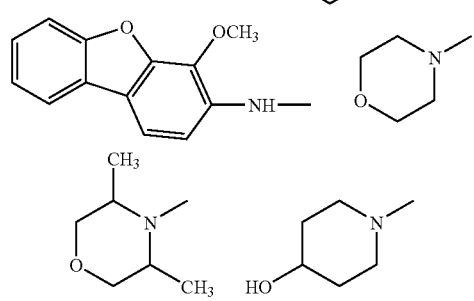

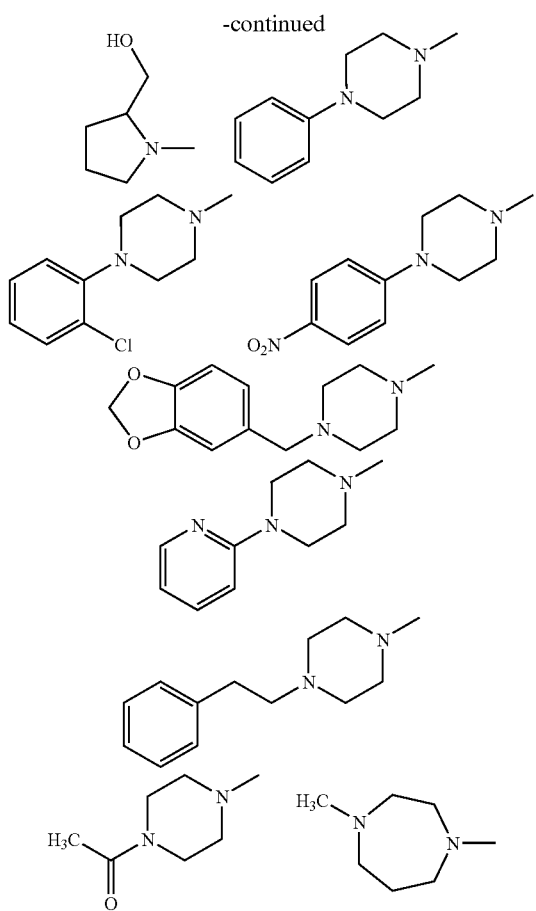
In another embodiment, the invention provides compounds of formula (I) having structure (II), wherein Y and X, taken together, are selected from the group consisting of
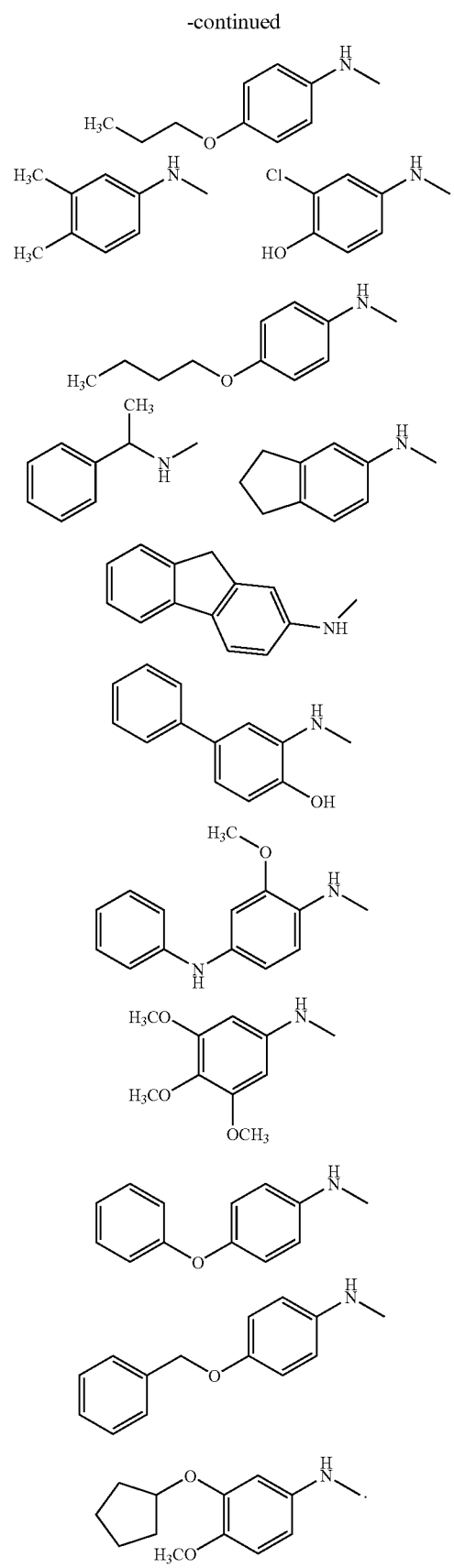

In another embodiment, the invention provides compounds of formula (I) having structure (II), wherein Y and X, taken together, are selected from the group consisting of

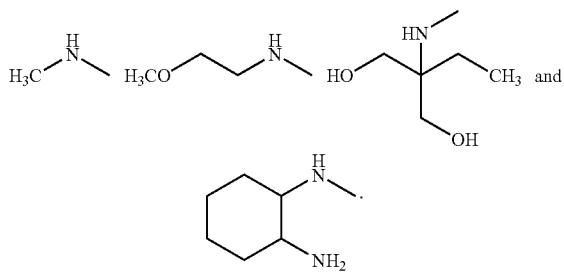

In another embodiment, the invention provides compounds of formula (I) having structure (III):

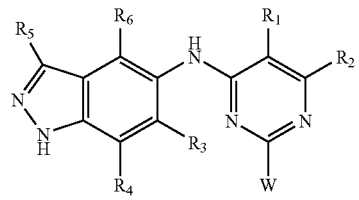

(III)

wherein $R_3$, $R_4$, $R_5$, $R_6$ are selected from the group consisting of
(1) H,
(2) substituted or unsubstituted $C_1$-$C_6$-alkyl,
(3) —COORt$^1$,
(4) —CONH$_2$,
(5) —OR$^{1t}$, and
(6) —NHR$^{1t}$.

In another embodiment, the invention provides compounds of formula (I) having structure (IV):

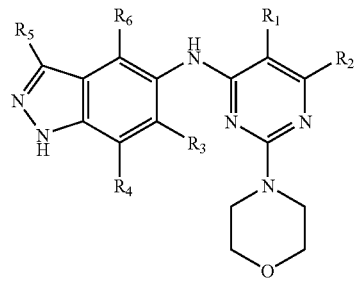

(IV)

wherein $R_3$, $R_4$, $R_5$, $R_6$ are selected from the group consisting of
(1) H,
(2) substituted or unsubstituted $C_1$-$C_6$-alkyl,
(3) —COOR$^{1t}$,
(4) —CONH$_2$,
(5) —OR$^{1t}$, and
(6) —NHR$^{1t}$.

In another embodiment, the invention provides compounds of formula (I) having structure (V):

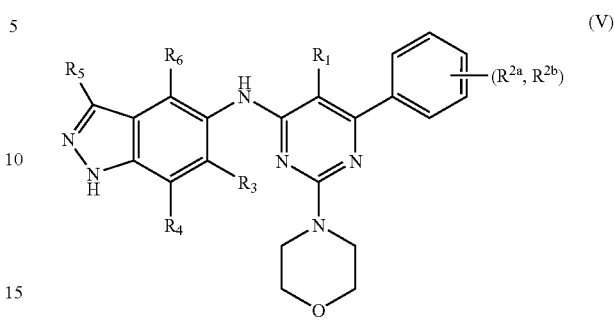

(V)

wherein $R_3$, $R_4$, $R_5$, $R_6$ are selected from the group consisting of
(1) H,
(2) substituted or unsubstituted $C_1$-$C_6$-alkyl,
(3) —COOR$^{1t}$,
(4) —CONH$_2$,
(5) —OR$^{1t}$, and
(6) —NHR$^{1t}$; and
$R^{2a}$ and $R^{2b}$ are selected from the group consisting of
(1) H,
(2) substituted or unsubstituted alkyl,
(3) halo,
(4) —(CH$_2$)$_q$—N(R$^{2c}$,R$^{2d}$),
(5) —(CH$_2$)$_q$—N(R$^{2c}$,R$^{2d}$)COR$^{2e}$,
(6) —(CH$_2$)$_q$—OR$^{2e}$,
(7) —(CH$_2$)$_q$—OCOR$^{2e}$,
(8) —(CH$_2$)$_q$—OCOOR$^{2e}$,
(9) —(CH$_2$)$_q$—COOR$^{2e}$,
(10) —(CH$_2$)$_q$—CONR$^{2c}$,
(11) —CN,
(12) —NO$_2$,
(13) —SO$_2$NH$_2$,
(14) —NHSO$_2$CH$_3$, and
(15) —SO$_2$R$^{2f}$,
wherein R$^{2c}$, R$^{2d}$, R$^{2e}$, and R$^{2f}$ are selected from the group consisting of
(a) H,
(b) substituted or unsubstituted alkyl, and
(c) substituted or unsubstituted phenyl; and
q is 0, 1, 2, 3, or 4.

In another embodiment, the invention provides compounds of formula (I) having structure (VI):

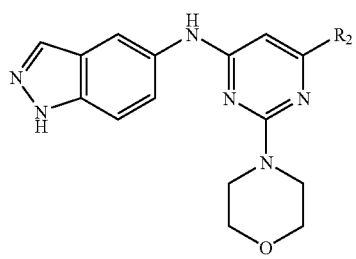

(VI)

wherein $R_2$ is selected from the group consisting of
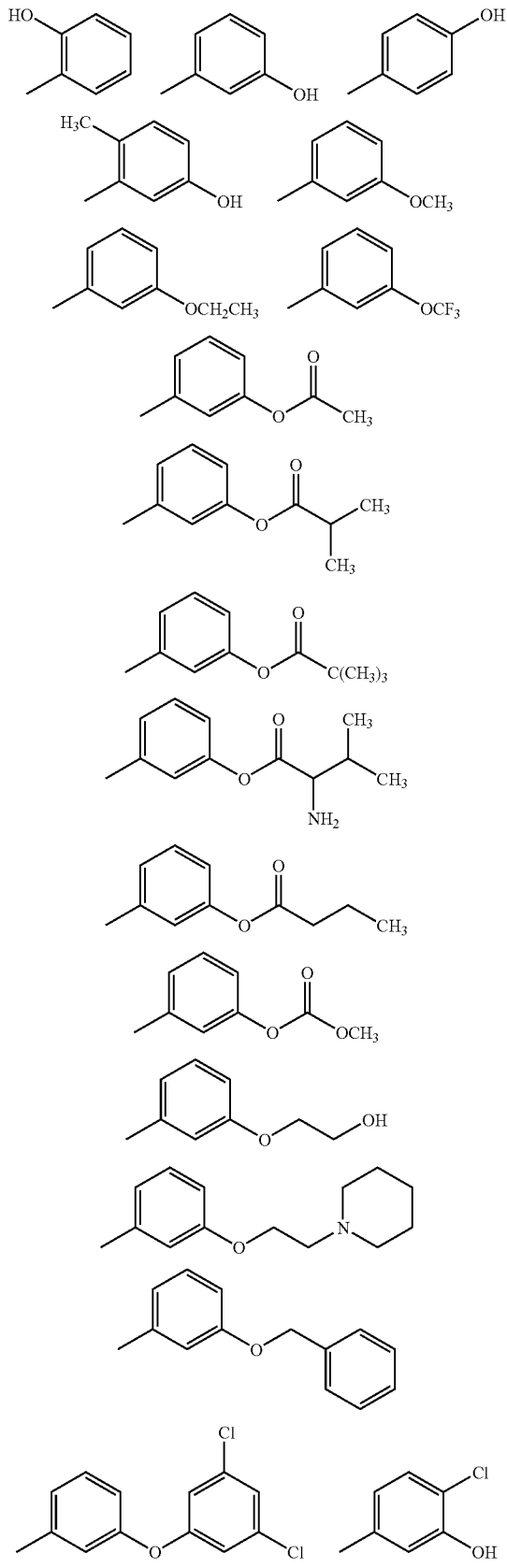
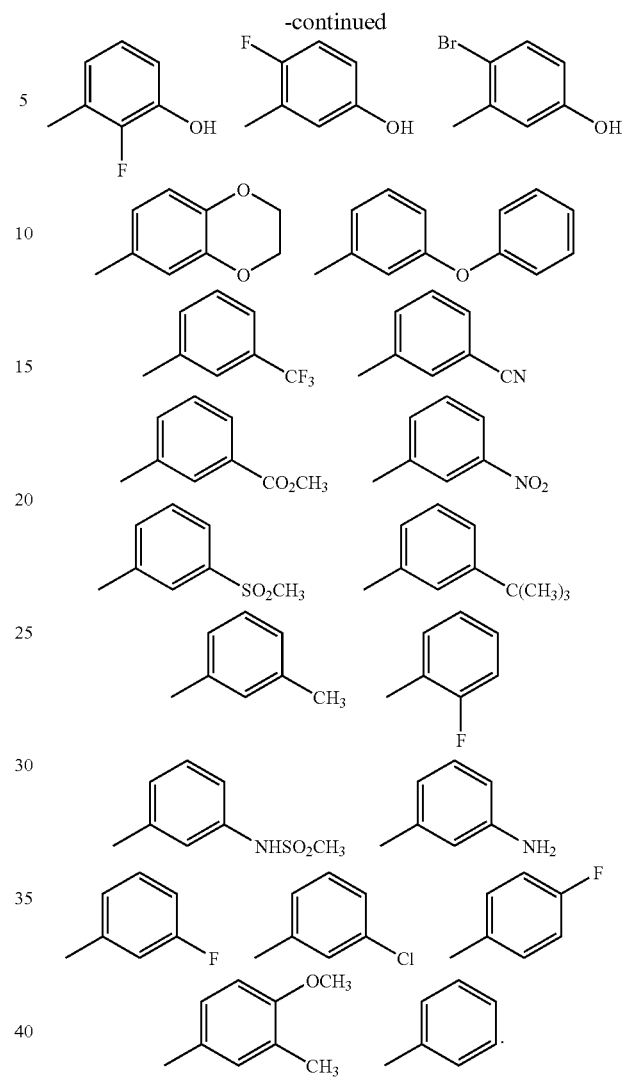
In another embodiment, the invention provides compounds of formula (I) having structure (VII):
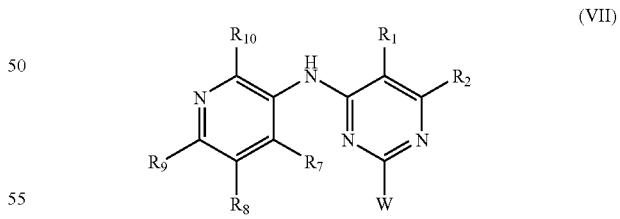
wherein $R_7$, $R_8$, $R_9$, and $R_{10}$ are selected from the group consisting of
(1) H,
(2) substituted or unsubstituted $C_1$-$C_6$-alkyl,
(3) —COOR$^{1r}$,
(4) —COONH$_2$,
(5) —OR$^{1r}$, and
(6) —NHR$^{1r}$.

In another embodiment, the invention provides compounds of formula (I) having structure (VIII):

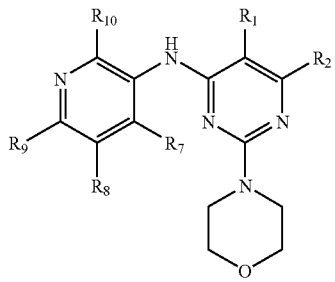

(VIII)

wherein $R_7$, $R_8$, $R_9$, $R_{10}$ are selected from the group consisting of
(1) H,
(2) substituted or unsubstituted $C_1$-$C_6$-alkyl,
(3) —COOR$^{1t}$,
(4) —CONH$_2$,
(5) —OR$^{1t}$, and
(6) —NHR$^{1t}$.

In another embodiment, the invention provides compounds of formula (I) having structure (IX):

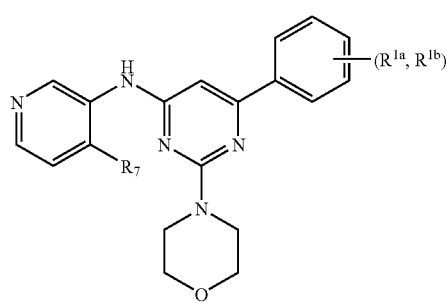

(IX)

wherein $R^{1a}$ and $R^{1b}$ are selected from the group consisting of
(1) H,
(2) substituted or unsubstituted alkyl,
(3) halo,
(4) —(CH$_2$)$_q$—N(R$^{2c}$,R$^{2d}$),
(5) —(CH$_2$)$_q$—N(R$^{2c}$,R$^{2d}$)COR$^{2e}$,
(6) —(CH$_2$)$_q$—OR$^{2e}$,
(7) —(CH$_2$)$_q$—OCOR$^{2e}$,
(8) —(CH$_2$)$_q$—OCOOR$^{2e}$,
(9) —(CH$_2$)$_q$—COOR$^{2e}$,
(10) —(CH$_2$)$_q$—CONR$^{2c}$,
(11) —CN,
(12) —NO$_2$,
(13) —SO$_2$NH$_2$,
(14) —NHSO$_2$CH$_3$, and
(15) —SO$_2$R$^{2f}$,
wherein R$^{2c}$, R$^{2d}$, R$^{2e}$, and R$^{2f}$ are selected from the group consisting of
(a) H,
(b) substituted or unsubstituted alkyl, and
(c) substituted or unsubstituted phenyl; and
R$_7$ is selected from the group consisting of
(1) H,
(2) substituted or unsubstituted $C_1$-$C_6$-alkyl,
(3) —COOR$^{1t}$,
(4) —COONH$_2$,
(5) —OR$^{1t}$, and
(6) —NHR$^{1t}$.

In another embodiment, the invention provides compounds of formula (I) having structure (X):

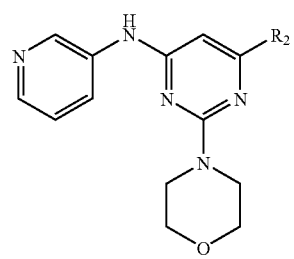

(X)

wherein $R_2$ is selected from the group consisting of

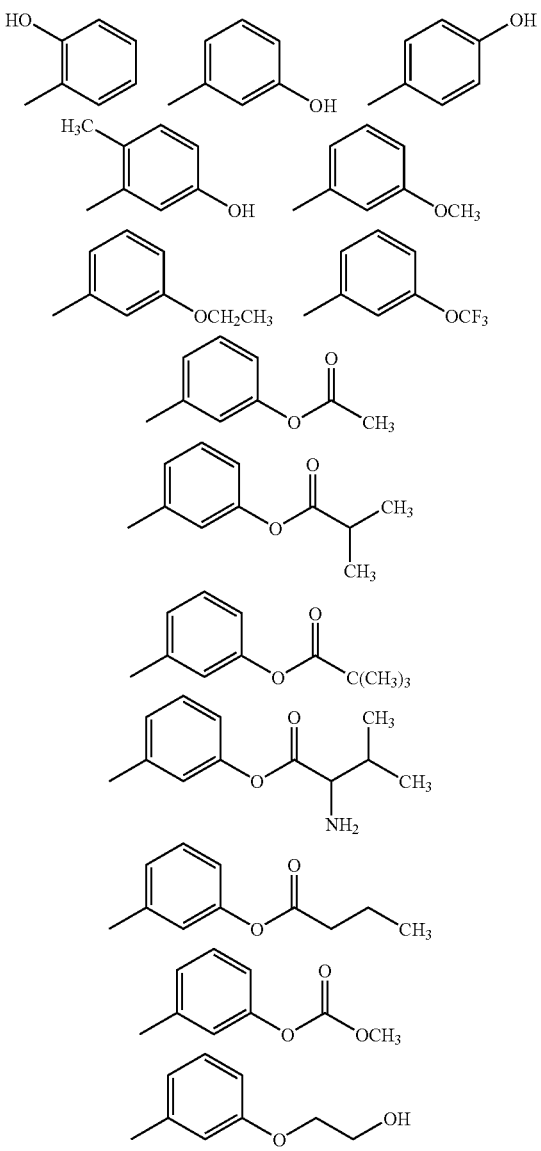

-continued

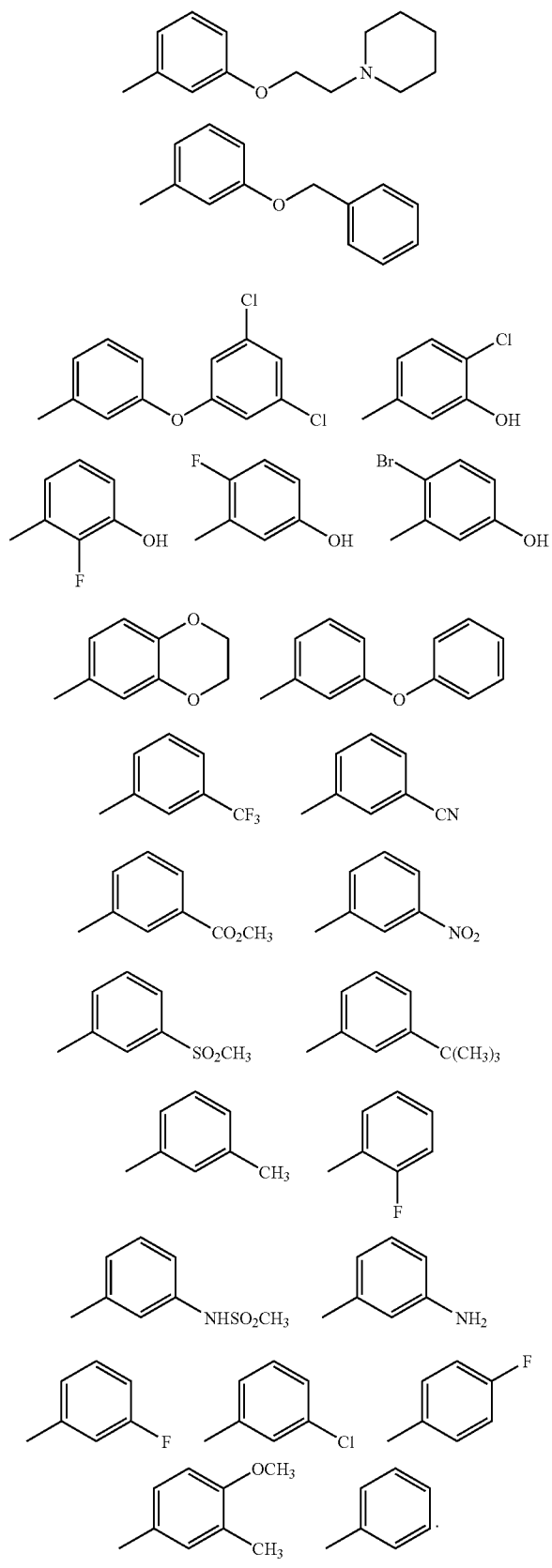

In another embodiment, the invention provides compounds of formula (I) having structure (XI):

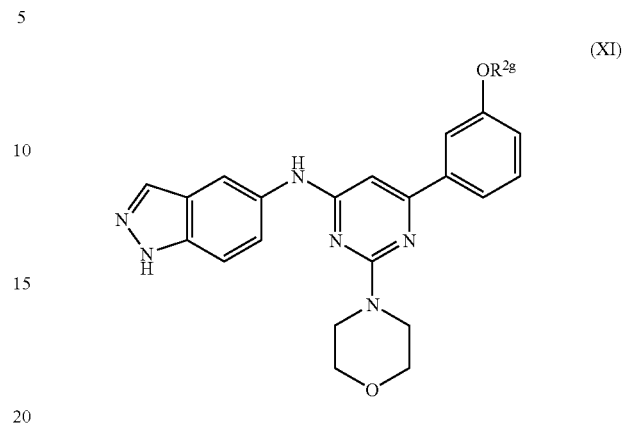

(XI)

wherein $R^{2g}$ is selected from the group consisting of
(1) H,
(2) substituted or unsubstituted alkyl,
(3) —CONHR$^{2h}$,
(4) —CON(R$^{2h}$)—(CH$_2$)$_{2-3}$—N(R$^{2h}$,R$^{2i}$),
(5) —COR$^{2j}$,
(6) —CO$_2$R$^{2j}$,
(7) —COC$_1$-C$_6$-alkyl-CO$_2$H,
(8) —CH$_2$—C(=O)R$^{2i}$,
(9) —CH$_2$—OC(=O)NHCHR$^{2i}$CO$_2$R$^{2j}$,
(10) —P(=O)(OR$^{2k}$,OR$^{2p}$),
(11)

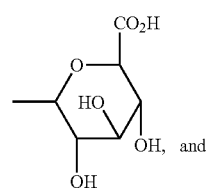, and (12)

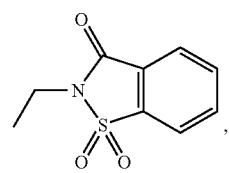, wherein R$^{2h}$, R$^{2i}$, R$^{2j}$, R$^{2k}$, and R$^{2p}$ are selected from the group consisting of
(a) H,
(b) substituted or unsubstituted alkyl, and
(c) substituted or unsubstituted aryl.

In another embodiment, the invention provides compounds of formula (I) having structure (XII):

(XII)

[Structure: pyrimidine with N-H linked pyridin-3-yl, 3-(OR$^{2g}$)phenyl, and morpholinyl substituents]

wherein R$^{2g}$ is selected from the group consisting of
(1) H,
(2) substituted or unsubstituted alkyl,
(3) —CONHR$^{2h}$,
(4) —CON(R$^{2h}$)—(CH$_2$)$_{2-3}$—N(R$^{2h}$,R$^{2i}$),
(5) —COR$^{2j}$,
(6) —CO$_2$R$^{2j}$,
(7) —COC$_1$-C$_6$-alkyl-CO$_2$H,
(8) —CH$_2$—OC(=O)R$^{2i}$,
(9) —CH$_2$—OC(=O)NHCHR$^{2i}$CO$_2$R$^{2j}$,
(10) —P(=O)(OR$^{2k}$,OR$^{2p}$).
(11)

[Structure: glucuronic acid-type sugar with CO$_2$H, OH groups], and (12)

[Structure: N-ethyl saccharin (1,2-benzisothiazol-3(2H)-one 1,1-dioxide)]

wherein R$^{2h}$, R$^{2i}$, R$^{2j}$, R$^{2k}$, and R$^{2p}$ are selected from the group consisting of
(a) H,
(b) substituted or unsubstituted alkyl, and
(c) substituted or unsubstituted aryl.

In another embodiment, the present invention provides compounds of the following formula (I):

I

[Structure: pyrimidine with Y—X— at 4-position, R$_1$ at 5-position, R$_2$ at 6-position, W at 2-position]

wherein W is:

[Structure: six-membered ring with N at top (attachment point), Z at bottom, (R$_3$)$_m$ substituents, n designation]

wherein Z is selected from the group consisting of —CH$_2$—, —NH—, —O—, —S—, and —NR$_6$—, where R$_6$ is an alkyl or substituted alkyl group;

R$_3$ is absent or selected from the group consisting of alkyl, substituted alkyl, amino, alkylamino, aminoalkyl, dialkylamino, dialkylaminoalkyl, alkoxy, alkenyl, substituted alkenyl, alkynyl, carbonylamino, and alkoxycarbonyl; and m and n are integers from 0-2;

X is a covalent bond or is selected from the group consisting of —CH$_2$—, —CHF—, —CF$_2$—, —NH—, —O—, —S—, and —NR$_5$—, where R$_5$ is an alkyl or substituted alkyl group;

Y is selected from the group consisting of heterocyclyl, substituted heterocyclyl, aryl, substituted aryl, heteroaryl, and substituted heteroaryl;

R$_1$ is selected from the group consisting of hydrogen, halogen, carboxylic acid, and alkyl; and R$_2$ is selected from the group consisting of heterocyclyl, substituted heterocyclyl, aryl, substituted aryl, heteroaryl, and substituted heteroaryl;

the tautomers thereof;

and the pharmaceutically acceptable salts, esters, or prodrugs thereof.

In another aspect of the compound of formula (I), W is a morpholinyl group as shown below:

[Structure: morpholine ring with (R$_3$)$_m$, O at bottom, n designation]

wherein, R$_3$, m, and n are as described above.

In another more particular embodiment of compound (I), W is an unsubstituted morpholinyl group.

In another more particular embodiment of compound (I), X is —NH—.

In another more particular embodiment of compound (I), Y is a heteroaryl or substituted heteroaryl group selected from pyridyl, and alkoxypyridyl.

In another more particular embodiment of compound (I), R$_1$ is hydrogen.

In another more particular embodiment of compound (I), R$_2$ is an aryl or substituted aryl group.

In another more particular embodiment of compound (I), R$_2$ is selected from the group consisting of phenyl, phenol, aniline, hydroxybenzyl, phenylalkoxycarbonyl, phenylcarbonylalkoxy, phenylaminocarbonyl, and phenylcarbonylamino.

In another more particular embodiment of compound (I), R$_3$ is absent.

In another embodiment, compounds of formula (II) are provided:

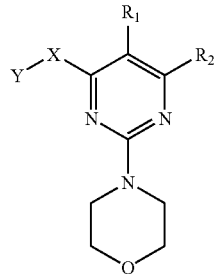

II wherein X is selected from the group consisting of —NH—, —O—, and —S—;

Y is selected from the group consisting of heterocyclyl, substituted heterocyclyl, aryl, substituted aryl, heteroaryl, and substituted heteroaryl;

$R_1$ is hydrogen, halogen, or a carboxylic acid group;

$R_2$ is selected from the group consisting of aryl, substituted aryl, heteroaryl, and substituted heteroaryl;

the tautomers thereof;

and the pharmaceutically acceptable salts, esters, or prodrugs thereof.

In another aspect of the compound of formula (II), X is —NH—.

In another aspect of the compound of formula (II), Y is a heteroaryl or substituted heteroaryl group selected from pyridyl, and alkoxypyridyl.

In another aspect of the compound of formula (II), $R_1$ is absent.

In another aspect of the compound of formula (II), $R_2$ is an aryl or substituted aryl group.

In another aspect of the compound of formula (II), $R_2$ is selected from the group consisting of phenyl, phenol, aniline, hydroxybenzyl, phenylalkoxycarbonyl, phenylcarbonylalkoxy, phenylaminocarbonyl, and phenylcarbonylamino.

In another aspect of the compound of formula (II), $R_3$ is absent.

In another embodiment, compounds of formula (XIII) are provided:

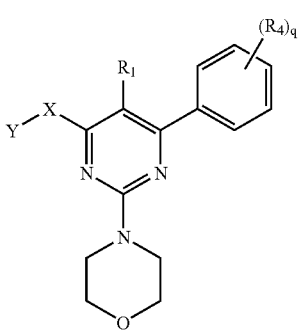

XIII wherein,

X is selected from the group consisting of —NH—, —O—, and —S—;

Y is selected from the group consisting of heterocyclyl, substituted heterocyclyl, aryl, substituted aryl, heteroaryl, and substituted heteroaryl;

$R_1$ is hydrogen, halogen, or a carboxylic acid;

$R_4$ is independently selected from the group consisting of hydrogen, halogen, alkyl, substituted alkyl, hydroxy, alkoxy, amino, alkylamino, aminoalkyl, dialkylamino, dialkylaminoalkyl, aryl, heteroaryl, heterocyclyl, carbonylamino, and alkoxycarbonyl; and q is an integer from 1-5;

the tautomers thereof;

and the pharmaceutically acceptable salts, esters, or prodrugs thereof.

In another aspect of the compound of formula (XIII), X is —NH— and $R_1$ is hydrogen.

In another aspect of the compound of formula (XIII), $R_4$ is selected from the group consisting of hydrogen, halogen, alkyl, substituted alkyl, hydroxy, alkoxy, amino, alkylamino, aminoalkyl, dialkylamino, dialkylaminoalkyl, carbonylamino, and alkoxycarbonyl.

In addition to the compounds described above with the noted provisos, the present invention also includes compounds defined as above, but that do not include the noted provisos. This second class of compounds of the invention does include the following provisos:

when X is O, then Y is substituted or unsubstituted aryl, substituted or unsubstituted heterocyclyl, or substituted or unsubstituted heteroaryl;

when W is morpholino, thiomorpholino, 1-oxido-thiomorpholino, 1,1-dioxido morpholino, piperazino, or N-substituted piperazino, $R_2$ is morpholino, thiomorpholino, 1-oxido-thiomorpholino, 1,1-dioxido-thiomorpholino, piperazino, or N'-[acetyl(alkanoyl of 1 to 3 carbon atoms)]piperazino, and X is NH, then Y is not hydrogen, alkyl of 1 to 3 carbon atoms, cyclohexyl, phenyl, chloro-phenyl, carboxy-phenyl, carbomethoxy-phenyl, or pyridyl;

when W is morpholino, thiomorpholino, 1-oxido-thiomorpholino, 1,1-dioxido morpholino, piperazino, or N-substituted piperazino, $R_2$ is morpholino, thiomorpholino, 1-oxido-thiomorpholino, 1,1-dioxido-thiomorpholino, piperazino, or N'-[acetyl(alkanoyl of 1 to 3 carbon atoms)]piperazino, and X is a direct link, then Y is not substituted or unsubstituted C1-C6-alkyl, or 1-oxidothiomorpholino; and when $R_2$ is phenyl independently substituted with one to five substituents selected from hydrogen, cycloalkyl, heterocycloalkyl, halo, nitro, amino, sulphonamido, or alkylsulphonylamino, $R_1$ is hydrogen, haloalkyl, alkyl, or halo, and X is $NR^{1x}$, then Y is substituted or unsubstituted heteroaryl or substituted or unsubstituted heterocyclyl.

Thus, in one aspect, the present invention provides two class of compounds, each including provisos. The difference between the two classes of compounds being the difference in provisos.

In other aspects, the invention provides methods for using compounds that are inhibitors of phosphotidylinositol 3-kinase (PI3K).

In another aspect of the invention, pharmaceutical formulations are provided that include one or more of the compounds described herein in combination with a pharmaceutically acceptable carrier.

Further objects, features, and advantages of the invention will be apparent from the following detailed description.

DETAILED DESCRIPTION OF THE PREFERRED EMBODIMENT

The present invention provides novel compounds that act as inhibitors of serine/threonine kinases, phospholipid kinases, and, more particularly, as inhibitors of phosphotidylinositol 3-kinase (PI3K) function. The compounds provided herein can be formulated into pharmaceutical formulations that are useful in treating patients with a need for an inhibitor of PI3K, especially, in particular embodiments, to provide compositions and methods for reducing cellular proliferation and in the treatment of cancer.

The following abbreviations and definitions are used throughout this application:

| Abbreviation | Meaning |
|---|---|
| PI3K | phosphotidylinositol 3-kinase |
| AcOH | acetic acid |
| ATP: | adenosine triphosphate |
| BOC | tert-butoxycarbonyl |
| CPT 11 | irinotecan |
| DIBAL-H | diisobutylaluminum hydride |
| DCM | dichloromethane |
| DDQ | 2,3-dichloro-5,6-dicyano-1,4-benzoquinone |
| DIEA | diisopropylethylamine |
| DMA: | N,N-Dimethylacetamide |
| DMF: | N,N-Dimethylformamide |
| DMSO | dimethyl sulfoxide |
| EDTA: | ethylene diamine tetraacetic acid |
| EtOAc: | ethyl acetate |
| EtOH: | ethanol |
| 5-FU | 5-fluourouracil |
| GCMS | Gas Chromatography/Mass Spectroscopy |
| HBTU: | O-benzotriazol-1-yl-N,N,N',N'-tetramethyl-uronium hexafluorophosphate |
| HPLC | High Performance Liquid Chromatography |
| $IC_{50}$ value: | the concentration of an inhibitor that causes a 50% reduction in a measured activity. |
| LCMS | Liquid Chromatography/Mass Spectroscopy |
| MeOH: | methanol |
| NMP: | N-methylpyrrolidone |
| NMR | nuclear magnetic resonance |
| Rt | room temperature (25° C.) |
| THF: | tetrahydrofuran |
| TLC | thin-layer chromatography |

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)—CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups include primary alkyl groups, secondary alkyl groups, and tertiary alkyl groups. Preferred alkyl groups include straight and branched chain alkyl groups and cyclic alkyl groups having 1 to 12 carbon atoms.

The phrase "substituted alkyl" refers to an alkyl group as defined above in which one or more bonds to a carbon(s) or hydrogen(s) are replaced by a bond to non-hydrogen non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group.

By halo is meant chloro, bromo, iodo, or fluoro or by halogen is meant chlorine, bromine, iodine or fluorine.

The phrase "alkenyl" refers to straight and branched chain and cyclic groups such as those described with respect to alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others. The phrase "substituted alkenyl" has the same meaning with respect to alkenyl groups that substituted alkyl groups has with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to straight and branched chain groups such as those described with respect to alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "heterocyclyl" refers to both aromatic and non-aromatic ring compounds including monocyclic, bicyclic, and polycyclic ring compounds such as, but not limited to, quinuclidinyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3- to 8-membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g., 1H-tetrazolyl, 2H-tetrazolyl, etc.); saturated 3- to 8-membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3- to 8-membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxa-diazolyl, etc.); saturated 3- to 8-membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3- to 8-membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3- to 8-membered rings containing 1 to 2 sulfur atoms and 1 to 3 nitrogen atoms such as, but not limited to, thiazolodinyl; saturated and unsaturated 3- to 8-membered rings containing 1 to 2 sulfur atoms such as, but not limited to, thienyl, dihydrodithienyl, dihydrodithionyl, tetrahydrothiophene, tetra-hydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3- to 8-membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3- to 8-membered rings containing an oxygen atom and 1 to 2 sulfur atoms such as, but not limited to, dihydrooxathienyl; saturated 3- to 8-membered rings containing 1 to 2 oxygen atoms and 1 to 2 sulfur atoms such as 1,4-oxathiane; unsaturated condensed rings containing 1 to 2 sulfur atoms such as benzothienyl, benzodithienyl; and unsaturated condensed heterocyclic rings containing an oxygen atom and 1 to 2 oxygen atoms such as benzoxathienyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to a heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" as used herein refers to a heteroaryl group as defined herein substituted by independent replacement of one, two or three of the hydrogen atoms thereon with Cl, Br, F, I, —OH, —CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]acetamide, 1,4-diphenylbenzene, N-[4-(2-phenylethynyl)phenyl]-2-[benzylamino]acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)phenyl]acetamide, 2-(ethylamino)-N-[4-(2-phenyl-ethynyl)phenyl]acetamide, 2-[(2-methylpropyl)amino]-N-[4-(2-phenylethynyl)phenyl]-acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl)phenyl]carboxamide, 2-{[(4-fluorophenyl)methyl]amino}-N-[4-(2-phenylethynyl)phenyl]acetamide, 2-{[(4-methyl-phenyl)methyl]amino}-N-[4-(2-phenylethynyl)phenyl]acetamide, 4-phenyl-1-(trifluoro-methyl)benzene, 1-butyl-4-phenylbenzene, 2-(cyclohexylamino)-N-[4-(2-phenylethynyl)-phenyl]acetamide, 2-(ethylmethylamino)-N-[4-(2-phenylethynyl)phenyl]acetamide, 2-(butylamino)-N-[4-(2-phenylethynyl)phenyl]acetamide, N-[4-(2-phenylethynyl)phenyl]-2-(4-pyridylamino)acetamide, N-[4-(2-phenylethynyl)phenyl]-2-(quinuclidin-3-ylamino)acetamide, N-[4-(2-phenylethynyl)phenyl]pyrrolidin-2-ylcarboxamide, 2-amino-3-methyl-N-[4-(2-phenylethynyl)phenyl]butanamide, 4-(4-phenylbuta-1,3-diynyl)phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl) [4-(4-phenylbuta-1,3-diynyl)phenyl]-carboxamide, N-[4-(2-phenylethynyl)phenyl]propanamide, 4-methoxyphenyl phenyl ketone, phenyl-N-benzamide, (tert-butoxy)-N-[(4-phenylphenyl)methyl]carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))methane, 5-[(4-methylpiperazinyl)methyl]-2-phenylthiophene, 2-(4-ethylphenyl)thiophene, 4-methylthio-1-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]amide, 2-(phenylmethylthio)pyridine, and benzylimidazole.

The term "heteroarylheteroaryl" refers to a biaryl group where both of the aryl groups are heteroaryl groups. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))amine, and dimethyl{2-[2-(5-methylpyrazin-2-yl)ethynyl] (4-pyridyl)}amine.

"Optionally substituted" refers to the optional replacement of hydrogen with one or more monovalent or divalent radicals. Optionally substituted groups include those described herein, for each group in which a distinct definition for substitution is supplied. Additionally, suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

Representative substituted aminocarbonyl groups include, for example, those shown below. These can be further substituted by heterocyclyl groups and heteroaryl groups as will be apparent to those having skill in the organic and medicinal chemistry arts in conjunction with the disclosure herein. Preferred aminocarbonyl groups include: N-(2-cyanoethyl)carboxamide, N-(3-methoxypropyl)carboxamide, N-cyclopropylcarboxamide, N-(2-hydroxy-isopropyl)carboxamide, methyl 2-carbonylamino-3-hydroxypropanoate, N-(2-hydroxypropyl)carboxamide, N-(2-hydroxy-isopropyl)carboxamide, N-[2-hydroxy-1-(hydroxymethyl)ethyl]carboxamide, N-(2-carbonylaminomethyl)acetamide, N-(2-(2-pyridyl)ethyl)carboxamide, N-(2-pyridylmethyl)carboxamide, N-(oxolan-2-ylmethyl)-carboxamide, N-(4-hydroxypyrrolidin-2-yl)carboxamide, N-[2-(2-hydroxyethoxy)ethyl]-carboxamide, N-(4-hydroxycyclohexyl)carboxamide, N-[2-(2-oxo-4-imidazolinyl)ethyl]-carboxamide, N-(carbonylaminomethyl)acetamide, N-(3-pyrrolidinylpropyl)carboxamide, N-[1-(carbonylaminomethyl)pyrrolidin-3-yl]acetamide, N-(2-morpholin-4-ylethyl)carboxamide, N-[3-(2-oxopyrrolidinyl)propyl]carboxamide, 4-methyl-2-oxopiperazinecarbaldehyde, N-(2-hydroxy-3-pyrrolidinylpropyl)carboxamide, N-(2-hydroxy-3-morpholin-4-ylpropyl)carboxamide, N-{2-[(5-cyano-2-pyridyl)amino]ethyl}carboxamide, 3-(dimethylamino)pyrrolidinecarbaldehyde, N-[(5-methylpyrazin-2-yl)methyl]carboxamide, 2,2,2-trifluoro-N-(1-formylpyrrolidin-3-yl)acetamide,

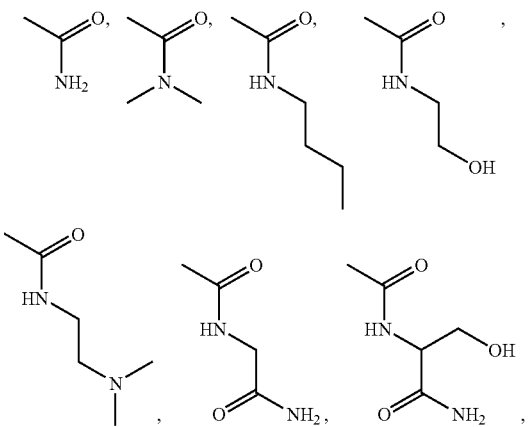

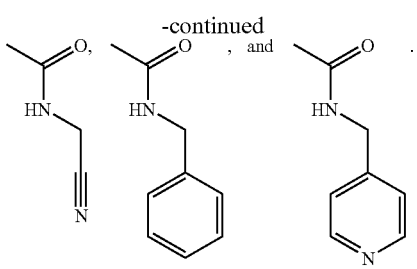

Representative substituted alkoxycarbonyl groups include, for example, those shown below. These alkoxycarbonyl groups can be further substituted as will be apparent to those having skill in the organic and medicinal chemistry arts in conjunction with the disclosure herein.

Representative substituted alkoxycarbonyl groups include, for example, those shown below. These alkoxycarbonyl groups can be further substituted as will be apparent to those having skill in the organic and medicinal chemistry arts in conjunction with the disclosure herein.

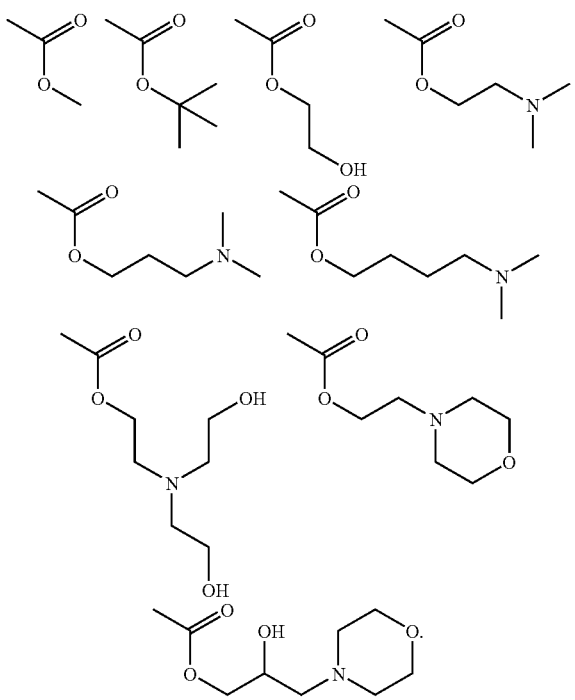

The term "protected" with respect to hydroxyl groups, amine groups, and sulfhydryl groups refers to forms of these functionalities which are protected from undesirable reaction with a protecting group known to those skilled in the art such as those set forth in *Protective Groups in Organic Synthesis*, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

As used herein, "limit", "treat" and "treatment" are interchangeable terms as are "limiting" and "treating" and, as used herein, include preventative (e.g., prophylactic) and palliative treatment or the act of providing preventative or palliative treatment.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of PI3K, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in antisense and gene therapy.

The PI3K inhibitors of this invention, as described herein, can be administered in the form of acid addition salts. The salts are conveniently formed by reacting a compound, if basic, with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. It will also be recognized that it is possible to administer amorphous forms of the PI3K inhibitors.

The subject invention also includes isotopically-labeled PI3K inhibitors, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Generally, the invention provides compounds having the formula I. The invention also provides tautomers of the compounds, pharmaceutically acceptable salts, esters and prodrugs of the compounds, and pharmaceutically acceptable salts, esters and prodrugs of the tautomers. Formula I has the following structure:

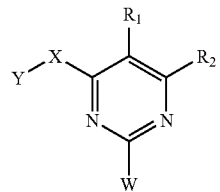

I

In one embodiment, W is:

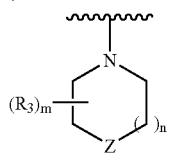

wherein Z is selected from the group consisting of —$CH_2$—, —NH—, —O—, —S—, and —$NR_6$—, where $R_6$ is an alkyl or substituted alkyl group;

$R_3$ is absent or selected from the group consisting of alkyl, substituted alkyl, amino, alkylamino, aminoalkyl, dialkylamino, dialkylaminoalkyl, alkoxy, alkenyl, substituted alkenyl, alkynyl, carbonylamino, and alkoxycarbonyl; and m and n are integers from 0-2;

X is a covalent bond or is selected from the group consisting of —$CH_2$—, —CHF—, —$CF_2$—, —NH—, —O—, —S—, and —$NR_5$—, where $R_5$ is an alkyl or substituted alkyl group;

Y is selected from the group consisting of heterocyclyl, substituted heterocyclyl, aryl, substituted aryl, heteroaryl, and substituted heteroaryl;

$R_1$ is selected from the group consisting of hydrogen, halogen, carboxylic acid, and alkyl; and $R_2$ is selected from the group consisting of heterocyclyl, substituted heterocyclyl, aryl, substituted aryl, heteroaryl, and substituted heteroaryl;

the tautomers thereof; and the pharmaceutically acceptable salts, esters, or prodrugs thereof.

In another aspect of the compound of formula (I), X is a covalent bond and Y is a morpholinyl group as shown below:

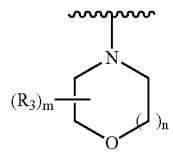

wherein, $R_3$, m, and n are as described above.

In another more particular embodiment of compound (I), X is a covalent bond and Y is an unsubstituted morpholinyl group.

In another more particular embodiment of compound (I), X is —NH—.

In another more particular embodiment of compound (I), Y is a heteroaryl or substituted heteroaryl group selected from pyridyl and alkoxypyridyl.

In another more particular embodiment of compound (I), $R_1$ is hydrogen.

In another more particular embodiment of compound (I), $R_2$ is an aryl or substituted aryl group.

In another more particular embodiment of compound (I), $R_2$ is selected from the group consisting of phenyl, phenol, aniline, hydroxybenzyl, phenylalkoxycarbonyl, phenylcarbonylalkoxy, phenylaminocarbonyl, and phenylcarbonylamino.

In another more particular embodiment of compound (I), $R_3$ is absent.

In one aspect of the invention, a compound of formula (II) is provided:

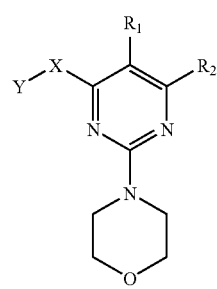

(II)

wherein, X is selected from the group consisting of —NH—, —O—, and —S—;

Y is selected from the group consisting of heterocyclyl, substituted heterocyclyl, aryl, substituted aryl, heteroaryl, and substituted heteroaryl;

$R_1$ is hydrogen, halogen, or a carboxylic acid group;

$R_2$ is selected from the group consisting of aryl, substituted aryl, heteroaryl, and substituted heteroaryl;

the tautomers thereof;

and the pharmaceutically acceptable salts, esters, or prodrugs thereof.

In another aspect of the compound of formula (II), X is —NH—.

In another aspect of the compound of formula (II), Y is a heteroaryl or substituted heteroaryl group selected from pyridyl and alkoxypyridyl.

In another aspect of the compound of formula (II), $R_1$ is hydrogen.

In another aspect of the compound of formula (II), $R_2$ is an aryl or substituted aryl group.

In another aspect of the compound of formula (II), $R_2$ is selected from the group consisting of phenyl, phenol, aniline, hydroxybenzyl, phenylalkoxycarbonyl, phenylcarbonylalkoxy, phenylaminocarbonyl, and phenylcarbonylamino.

In another aspect of the compound of formula (II), $R_3$ is absent.

In another aspect of the invention, compounds of formula (XIII) are provided:
wherein,

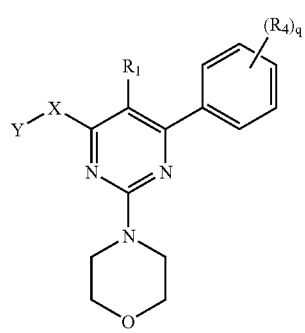

XIII

X is selected from the group consisting of —NH—, —O—, and —S—;

Y is selected from the group consisting of heterocyclyl, substituted heterocyclyl, aryl, substituted aryl, heteroaryl, and substituted heteroaryl;

$R_1$ is hydrogen, halogen, or a carboxylic acid;

$R_4$ is independently selected from the group consisting of hydrogen, halogen, alkyl, substituted alkyl, hydroxy, alkoxy, amino, alkylamino, aminoalkyl, dialkylamino, dialkylaminoalkyl, aryl, heteroaryl, heterocyclyl, carbonylamino, and alkoxycarbonyl;

q is an integer from 1-5.

the tautomers thereof;

and the pharmaceutically acceptable salts, esters, or prodrugs thereof.

In another aspect of the compound of formula (XIII), X is —NH— and $R_1$ is hydrogen.

In another aspect of the compound of formula (XIII), $R_4$ is selected from the group consisting of hydrogen, halogen, alkyl, substituted alkyl, hydroxy, alkoxy, amino, alkylamino, aminoalkyl, dialkylamino, dialkylaminoalkyl, carbonylamino, and alkoxycarbonyl.

Other compounds of the invention are described above in the Summary of the Invention.

In other aspects, the present invention provides compositions that include the phosphotidylinositol 3-kinase inhibitor compounds described herein, and methods that utilize the phosphotidylinositol 3-kinase inhibitor compounds described herein. In addition to the compounds described above, the compositions and methods of the invention can also include and utilize compounds having the following formula:

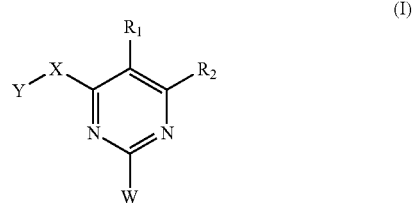

(I)

its stereoisomers, tautomers, pharmaceutically acceptable salts, esters, and prodrugs, wherein Y is selected from the groups consisting of
(1) substituted or unsubstituted $C_1$-$C_6$-alkyl,
(2) substituted or unsubstituted $C_2$-$C_6$-alkenyl,
(3) substituted or unsubstituted $C_2$-$C_6$-alkynyl,
(4) substituted or unsubstituted aryl,
(5) substituted or unsubstituted heterocyclyl, and
(6) substituted or unsubstituted heteroaryl;

X is selected from the group consisting of
(1) a direct link,
(2) —N($R^{1x}$)—,
(3) —(CH$_2$)$_m$—C($R^{2x}$,$R^{3x}$)—N($R^{1x}$)—,
(4) —O—,
(5) —S—,
(6) —SO—,
(7) —SO$_2$—,
(8) —C($R^{2x}$,$R^{3x}$)—, and
(9)

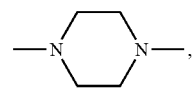

wherein $R^{1x}$, $R^{2x}$, and $R^{3x}$ are selected from the group consisting of
(a) H,
(b) substituted or unsubstituted $C_1$-$C_6$-alkyl,
(c) substituted or unsubstituted $C_2$-$C_6$-alkenyl, (d) substituted or unsubstituted $C_2$-$C_6$-alkynyl,
(e) substituted or unsubstituted aryl,
(f) substituted or unsubstituted heterocyclyl,
(g) substituted or unsubstituted heteroaryl; and
m is 0, 1, 2, 3, or 4;
$R^1$ is selected from the group consisting of
(1) H,
(2) substituted or unsubstituted $C_1$-$C_6$-alkyl,
(3) —COOH,
(4) halo,
(5) —$OR^{1t}$, and
(6) —$NHR^{1t}$,
wherein $R^{1t}$ is H or $C_1$-$C_6$-alkyl;
$R_2$ is selected from the group consisting of
(1) substituted or unsubstituted aryl,
(2) substituted or unsubstituted heteroaryl, and
(3) substituted or unsubstituted heterocyclyl; and
W is selected from the group consisting of
(1) substituted or unsubstituted $C_1$-$C_6$-alkyl,
(2) —$N(R^{1w},R^{2w})$, and
(3)

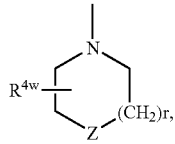

wherein $R^{1w}$ and $R^{2w}$ are selected from the group consisting of
(a) H,
(b) substituted or unsubstituted $C_1$-$C_6$-alkyl,
(c) substituted or unsubstituted aryl,
(d) substituted or unsubstituted heterocyclyl, and
(e) substituted or unsubstituted heteroaryl, wherein $R^{1w}$ and $R^{2w}$ are not both H;
Z is selected from the group consisting of
(a) —O—,
(b) —$NR^z$—,
(c) —S—,
(d) —SO—,
(e) —$SO_2$—, and
(f) —$CH_2$—,
wherein $R^z$ is H or substituted or unsubstituted alkyl group; and
$R^{4w}$ is selected from the group consisting of
(a) H,
(b) substituted or unsubstituted $C_1$-$C_6$-alkyl,
(c) —$COOR^{5w}$,
(d) —$CONH_2$,
(e) —$OR^{5w}$, and
(f) —$NHR^{5w}$,
wherein $R^{5w}$ is H or $C_1$-$C_6$-alkyl; and
r is 0, 1, or 2.

In one aspect, the invention provides pharmaceutical formulation that include one or more compounds described herein in combination with a pharmaceutically acceptable carrier. The pharmaceutical formulations of the invention can include additional therapeutic agents including, for example, other conventional cytotoxic agents. Representative other conventional cytotoxic agents include for example, irinotecan, topotecan, gemcitabine, gleevec, herceptin, 5-fluorouracil, leucovorin, carboplatin, cisplatin, taxanes, tezacitabine, cyclophosphamide, vinca alkaloids, imatinib, anthracyclines, rituximab, tamoxifen, CPT 11, and trastuzumab, and the like, and are considered to fall within the scope of this invention.

In another aspect, the invention provides methods for using the compounds described herein. For example, the compounds described herein can be used in the treatment of cancer. The compounds described herein can also be used in the manufacture of a medicament for the treatment of cancer.

The methods can utilize pharmaceutical formulations that include one or more compounds described herein in combination with a pharmaceutically acceptable carrier. The methods can also utilize pharmaceutical formulations of the invention that include additional therapeutic agents.

In one embodiment, the invention provides a method for inhibiting phosphotidylinositol (PI) 3-kinase activity in a human or animal subject. In the method, an amount of a compound described herein effective to inhibit phosphotidylinositol (PI) 3-kinase activity in the human or animal subject is administered to the human or animal subject.

In another embodiment, the invention provides a method of treating a patient in need of an inhibitor of phosphotidylinositol 3-kinase (PI3K) is provided. In the method, a pharmaceutical formulation containing an effective amount of a compound described herein is administered to a patient in need thereof.

In another embodiment, the invention provides a method for treating a condition (e.g., cancer) by modulation of phosphotidylinositol (PI) 3-kinase activity. In the method, an effective amount of a compound described herein is administered to a human or animal subject in need of such treatment.

In another embodiment, the invention provides a method for treating a cancer disorder in a human or animal subject. In the method, a composition comprising an amount of a compound described herein effective to treat cancer is administered to a human or animal subject in need thereof. As noted above, the administered composition can further include additional therapeutic agents (e.g., conventional cytotoxic agents).

In another embodiment, the invention provides a method for inhibiting tumor growth in a patient. In the method, an effective amount of a compound described herein is administered to a patient having a tumor.

In another embodiment, the invention provides a method for inhibiting the proliferation of capillaries in a patient. In the method, an effective amount of a compound described herein is administered to a patient in need.

The invention also provides methods of preparing pharmaceutical formulations comprising mixing any of the above-described compounds with a pharmaceutically acceptable carrier, water, or an aqueous solution.

Pharmaceutical Compositions

Pharmaceutical compositions of the present invention comprise a therapeutically effective amount of a phosphotidylinositol 3-kinase inhibitor compound described herein formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil;

olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracistemally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5μ. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, tumor growth is reduced or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat tumor growth, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

A "kit" as used in the instant application comprises a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card, e.g., as follows "First Week, Monday, Tuesday," . . . etc . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

The kits of the present invention may also comprise, in addition to a PI3K inhibitor, one or more additional pharmaceutically active compounds. Preferably, the additional compound is another PI3K inhibitor or another compound useful to treat cancer, angiogenesis, or tumor growth. The additional compounds may be administered in the same dosage form as the PI3K inhibitor or in different dosage forms. Likewise, the additional compounds can be administered at the same time as the PI3K inhibitor or at different times.

All references and patents cited herein are incorporated by reference.

The present invention, thus generally described, will be understood more readily by reference to the following examples, which are provided by way of illustration and are not intended to be limiting of the present invention.

EXAMPLES

Experimental

Compounds of the invention may be generally prepared using procedures well known to those skilled in the art, for example in accordance with the following representative methods (e.g., Methods 1 and 2 below) and reaction schemes.

Method 1

Resin bound 2-(pyrazolo)trihydropyrimidin-4-one (3) (Step 1)

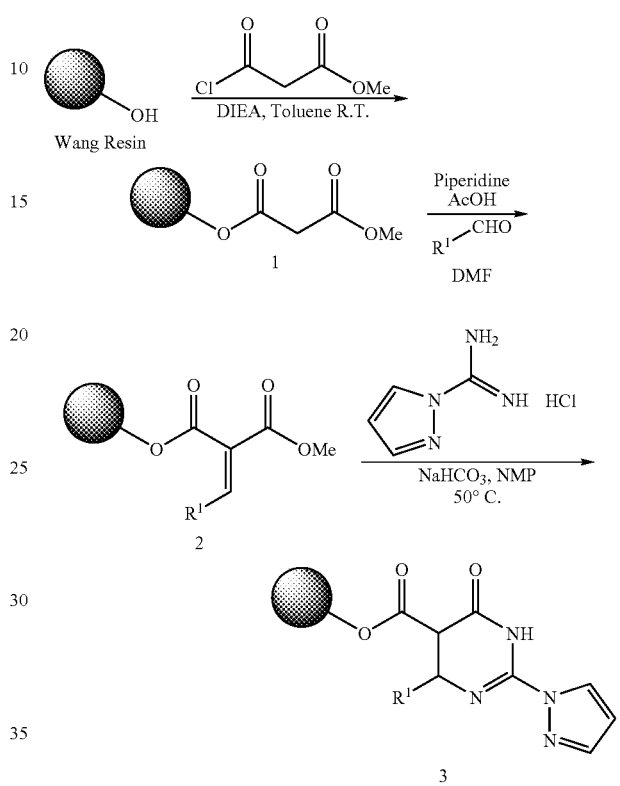

Wang resin (1.0 g, 0.55 mmol, 1 eq) was suspended in toluene (10 mL) and DIEA (0.377 mL, 2.2 mmol, 4.0 eq) was added, followed by methyl malonyl chloride (0.236 mL, 2.2 mmol, 4.0 eq). The mixture was shaken overnight at room temperature. The resin was filtered and washed with $CH_2Cl_2$, MeOH, water, DMF, $CH_2Cl_2$ then dried to obtain resin bound methyl malonate 1. Resin 1 (300 mg, 0.165 mmol, 1.0 eq) was suspended in a solution of piperidine (16.3 µL, 0.165 mmol, 1.0 eq) and acetic acid (9.4 µL, 0.165 mmol, 1.0 eq) in DMF (3 mL) and the aldehyde (10.0 eq) was added. The mixture was shaken at room temperature overnight. The resin was filtered, washed with DMF and $CH_2Cl_2$, then dried to give the resin bound α,β unsaturated diester 2, which was used in the next step without analytics, since cleavage from the resin causes extensive decomposition. Resin 2 (300 mg, 0.165 mmol, 1.0 eq) was suspended in NMP (3 mL), and 1-H-pyrazole carboxamidine hydrochloride (121 mg 0.825 mmol, 5.0 eq) was added, followed by $NaHCO_3$ (35 mg, 0.412 mmol, 2.5 eq). The reaction mixture was shaken overnight at 50° C., then the resin was filtered, washed with DMF, water, MeOH, $CH_2Cl_2$ and dried, to obtain the desired resin bound 6-$R^1$-4-oxo-2-pyrazolyl-3,5,6-trihydropyrimidine-5-carboxylic acid 3. An analytical sample of the cleaved product was obtained treating the resin with 95% TFA/$H_2O$ for 1.5 h at room temperature, filtering and evaporating under reduced pressure.

Resin bound 2-pyrazolopyrimidinone (4) (Step 2)

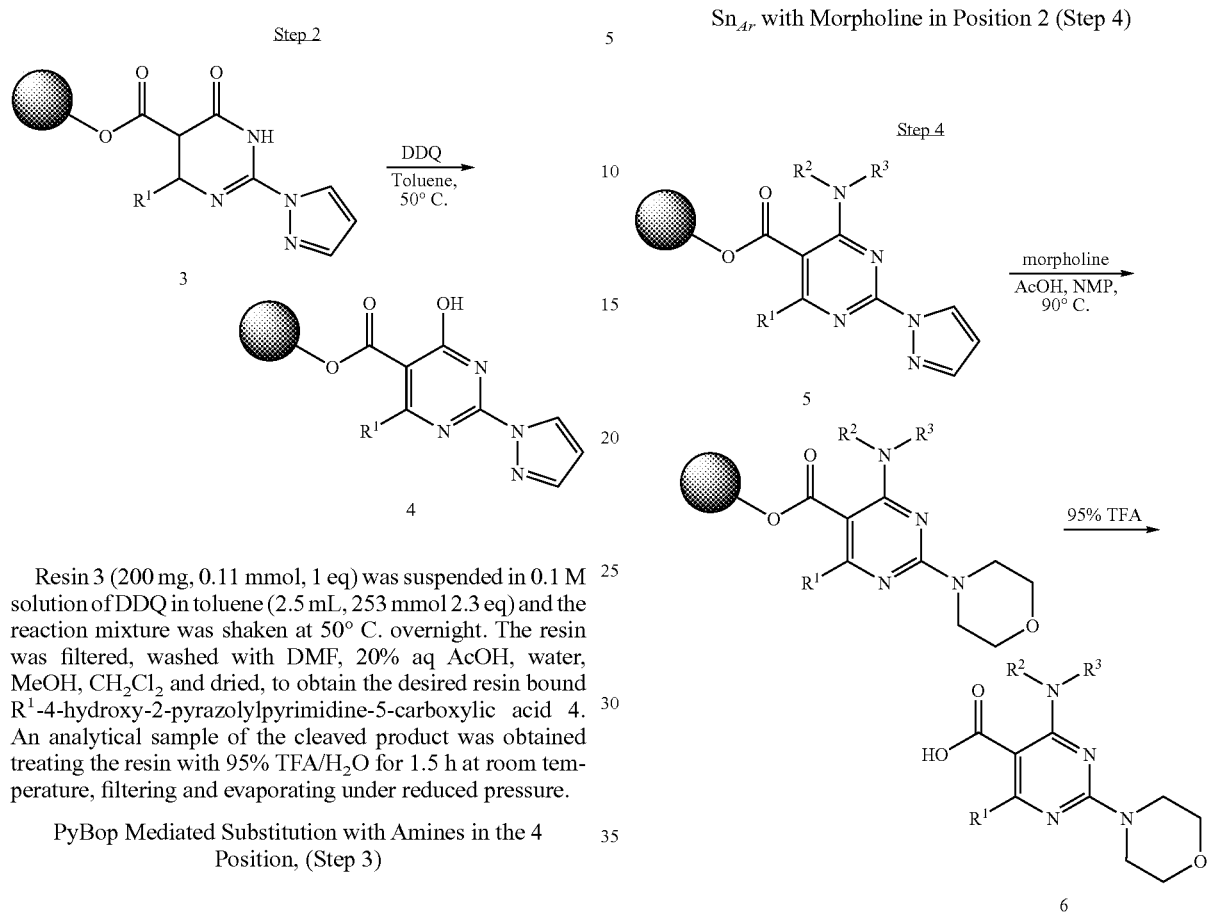

Resin 3 (200 mg, 0.11 mmol, 1 eq) was suspended in 0.1 M solution of DDQ in toluene (2.5 mL, 253 mmol 2.3 eq) and the reaction mixture was shaken at 50° C. overnight. The resin was filtered, washed with DMF, 20% aq AcOH, water, MeOH, $CH_2Cl_2$ and dried, to obtain the desired resin bound $R^1$-4-hydroxy-2-pyrazolylpyrimidine-5-carboxylic acid 4. An analytical sample of the cleaved product was obtained treating the resin with 95% TFA/$H_2O$ for 1.5 h at room temperature, filtering and evaporating under reduced pressure.

PyBop Mediated Substitution with Amines in the 4 Position, (Step 3)

A mixture of resin 4 (150 mg, 0.082 mmol, 1 eq), the amine of choice (10 eq), and PyBop (85 mg, 0.164 mmol, 2 eq) in NMP was shaken at room temperature overnight. The resin was filtered, washed with DMF, MeOH, and $CH_2Cl_2$, and dried, to obtain the desired resin bound 6-$R^1$-4-aminoalkyl (or aryl)-2-pyrazolylpyrimidine-5-carboxylic acid 5. An analytical sample of the cleaved product was obtained treating the resin 95% TFA/$H_2O$ for 1.5 h at room temperature, filtering and evaporating under reduced pressure.

$Sn_{Ar}$ with Morpholine in Position 2 (Step 4)

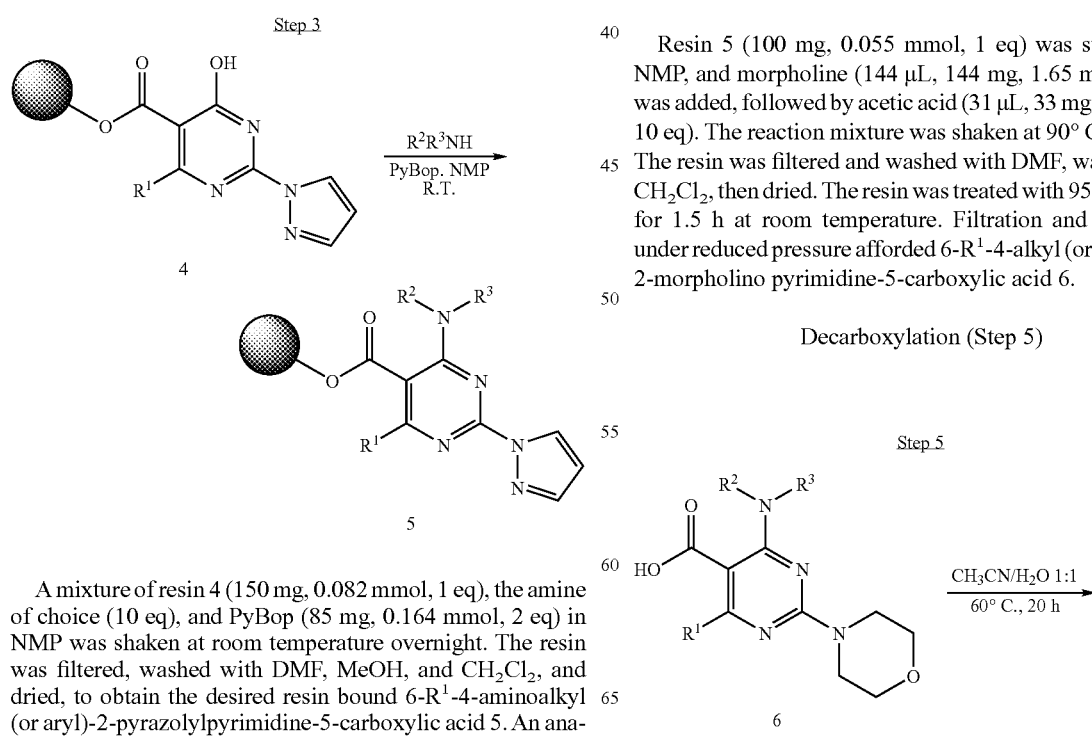

Resin 5 (100 mg, 0.055 mmol, 1 eq) was suspended in NMP, and morpholine (144 μL, 144 mg, 1.65 mmol, 30 eq) was added, followed by acetic acid (31 μL, 33 mg, 0.55 mmol, 10 eq). The reaction mixture was shaken at 90° C. overnight. The resin was filtered and washed with DMF, water, MeOH, $CH_2Cl_2$, then dried. The resin was treated with 95% TFA/$H_2O$ for 1.5 h at room temperature. Filtration and evaporation under reduced pressure afforded 6-$R^1$-4-alkyl (or aryl)amino-2-morpholino pyrimidine-5-carboxylic acid 6.

Decarboxylation (Step 5)

-continued

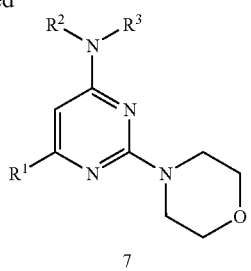

The carboxylic acid 6 was dissolved in a mixture of acetonitrile and water (1:1, 2 mL) and the solution was heated at 60° C. overnight. The solution was cooled down to room temperature and then lyophilized. After purification by reverse phase liquid chromatography, the desired trisubstituted pyrimidine 7 was obtained as a solid.

Example 1

(Synthesis of 3-[6-(1H-indazol-5-ylamino)-2-morpholin-4-ylpyrimidin-4-yl]phenol)

6-(3-hydroxyphenyl)-4-oxo-2-pyrazolyl-3,5,6-trihydropyrimidine-5-carboxylic acid Wang resin (1.0 g, 0.55 mmol, 1 eq) was suspended in toluene (10 mL) and DIEA (0.377 mL, 2.2 mmol, 4.0 eq) was added, followed by methyl malonyl chloride (0.236 mL, 2.2 mmol, 4.0 eq). The mixture was shaken overnight at room temperature. The resin was filtered and washed with $CH_2Cl_2$, MeOH, water, DMF, $CH_2Cl_2$ then dried to obtain resin bound methyl malonate (1). Resin 1 (300 mg, 0.165 mmol, 1.0 eq) was suspended in a solution of piperidine (16.3 µL, 0.165 mmol, 1.0 eq) and acetic acid (9.4 µL, 0.165 mmol, 1.0 eq) and 3-hydroxybenzaldehyde (201 mg, 1.65 mmol, 10.0 eq) was added. The mixture was shaken at room temperature overnight. The resin was filtered, washed with DMF and $CH_2Cl_2$, dried, suspended in NMP, and 1-H-pyrazole carboxamidine hydrochloride (121 mg 0.825 mmol, 5.0 eq) was added, followed by $NaHCO_3$ (35 mg, 0.412 mmol, 2.5 eq). The reaction mixture was shaken overnight at 50° C., then the resin was filtered, washed with DMF, water, MeOH, $CH_2Cl_2$ and dried. To obtain an analytical sample, 20 mg of the resin were treated with 95% $TFA/H_2O$ for 1.5 h at room temperature. Filtration and evaporation under reduced pressure afforded 6-(3-hydroxyphenyl)-4-oxo-2-pyrazolyl-3,5,6-trihydropyrimidine-5-carboxylic acid.

HPLC (Buffer A: 0.1% $TFA/H_2O$; Buffer B: 0.1% TFA/$CH_3CN$; column: C18, 4.6×250 mm; flow: 1 mL/min; gradient: 2.1%, 5%-80% B in 36 min.): $R_t$=14.70.

LC/MS (ion spray, 50 eV, m/z): 275 ($M+H_2O+H^+$).

4-hydroxy-6-(3-hydroxyphenyl)-2-pyrazolylpyrimidine-5-carboxylic acid

Resin bound 6-(3-hydroxyphenyl)-4-oxo-2-pyrazolyl-3,5,6-trihydropyrimidine-5-carboxylic acid (200 mg, 0.11 mmol, 1 eq) was suspended in 0.1 M solution of DDQ in toluene (2.5 mL, 253 mmol 2.3 eq) and the reaction mixture was shaken at 50° C. overnight. The resin was filtered, washed with DMF, 20% aq AcOH, water, MeOH, $CH_2Cl_2$ and dried. To obtain an analytical sample, 20 mg of the resin were treated with 95% $TFA/H_2O$ for 1.5 h at room temperature. Filtration and evaporation under reduced pressure afforded 4-hydroxy-6-(3-hydroxyphenyl)-2-pyrazolylpyrimidine-5-carboxylic acid.

HPLC (Buffer A: 0.1% $TFA/H_2O$; Buffer B: 0.1% TFA/$CH_3CN$; column: C18, 4.6×250 mm; flow: 1 mL/min; gradient: 2.1%, 5%-80% B in 36 min.): $R_t$=15.78.

LC-MS (ion spray, 50 eV, m/z): 299 ($M+H^+$).

Resin bound 6-(3-hydroxyphenyl)-4-(1H-indazol-5-ylamino)-2-pyrazolylpyrimidine-5-carboxylic acid A mixture of resin bound 4-hydroxy-6-(3-hydroxyphenyl)-2-pyrazolylpyrimidine-5-carboxylic acid (150 mg, 0.082 mmol, 1 eq), 5-aminoindazole (110 mg, 0.82 mmol, 10 eq), and PyBop (85 mg, 0.164 mmol, 2 eq) in NMP was shaken at room temperature overnight. The resin was filtered, washed with DMF, MeOH, and $CH_2Cl_2$, and dried. To obtain an analytical sample, 20 mg of the resin were treated with 95% $TFA/H_2O$ for 1.5 h at room temperature. Filtration and evaporation under reduced pressure afforded 6-(3-hydroxyphenyl)-4-(1H-indazol-5-ylamino)-2-pyrazolylpyrimidine-5-carboxylic acid.

HPLC (Buffer A: 0.1% $TFA/H_2O$; Buffer B: 0.1% TFA/$CH_3CN$; column: C18, 4.6×250 mm; flow: 1 mL/min; gradient: 2.1%, 5%-80% B in 36 min.): $R_t$=20.72.

LC-MS (ion spray, 50 eV, m/z): 414 ($M+H^+$).

Resin bound 6-(3-hydroxyphenyl)-4-(1H-indazol-5-ylamino)-2-morpholin-4-ylpyrimidine-5-carboxylic acid Resin bound 6-(3-hydroxyphenyl)-4-(1H-indazol-5-ylamino)-2-pyrazolylpyrimidine-5-carboxylic acid (100 mg, 0.055 mmol, 1 eq) was suspended in NMP, and morpholine (144 µL, 144 mg, 1.65 mmol, 30 eq) was added, followed by acetic acid (31 µL, 33 mg, 0.55 mmol, 10 eq). The reaction mixture was shaken at 90° C. overnight. The resin was filtered and washed with DMF, water, MeOH, $CH_2Cl_2$, then dried. The resin was treated with 95% $TFA/H_2O$ for 1.5 h at room temperature. Filtration and evaporation under reduced pressure afforded 6-(3-hydroxyphenyl)-4-(1H-indazol-5-ylamino)-2-morpholin-4-ylpyrimidine-5-carboxylic acid.

HPLC (Buffer A: 0.1% $TFA/H_2O$; Buffer B: 0.1% TFA/$CH_3CN$; column: C18, 4.6×250 mm; flow: 1 mL/min; gradient: 2.1%, 5%-80% B in 36 min.): $R_t$=16.97.

LC-MS (ion spray, 50 eV, m/z): 433 ($M+H^+$).

3-[6-(1H-indazol-5-ylamino)-2-morpholin-4-ylpyrimidin-4-yl]phenol 6-(3-hydroxyphenyl)-4-(1H-indazol-5-ylamino)-2-morpholin-4-ylpyrimidine-5-carboxylic acid was dissolved in a mixture of acetonitrile and water (1:1, 2 mL) and the solution was heated at 60° C. overnight. The solution was cooled down to room temperature and then lyophilized. After purification by reverse phase liquid chromatography (Buffer A: 0.1% $TFA/H_2O$; Buffer B: 0.1% $TFA/CH_3CN$, column: C18, 5µ, 10×50 mm, gradient 5% B-95% B in 9 min) the Bis TFA salt of 3-[6-(1H-indazol-5-ylamino)-2-morpholin-4-ylpyrimidin-4-yl]phenol was obtained as a pale yellow solid.

$^1$H-NMR (HCl salt, 60% $CD_3CN/D_2O$, 300 MHz): 8.09 (s, 1H), 8.03 (bs, 1H), 7.61 (1H, d, J=8.7), 7.55 (bm, 1H), 7.38 (app. t, 1H, J=7.8), 7.17 (bd, 1H, J=7.8), 7.10 (bs, 1H), 7.06 (d, 1H, J=8.7), 6.42 (bs, 1H), 3.75 (app. s, 8H).

HPLC (Buffer A: 0.1% $TFA/H_2O$; Buffer B: 0.1% TFA/$CH_3CN$; column: C18, 4.6×250 mm; flow: 1 mL/min; gradient: 2.1%, 5%-80% B in 36 min.): $R_t$=18.17.

LC-MS (ion spray, 50 eV, m/z): 389 ($M+H^+$).

Method 2

Solution Phase Synthesis of 3-[2-Morpholin-4-yl-6-(3-pyridylamino)pyrimidin-4-yl]phenol

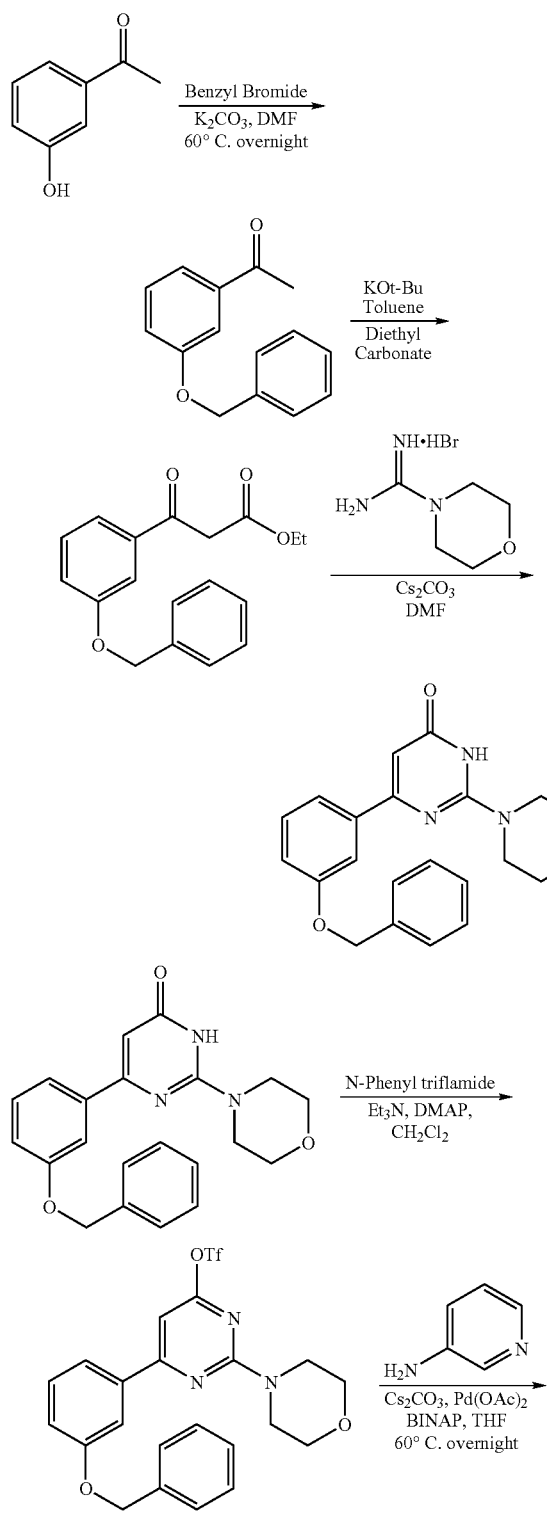

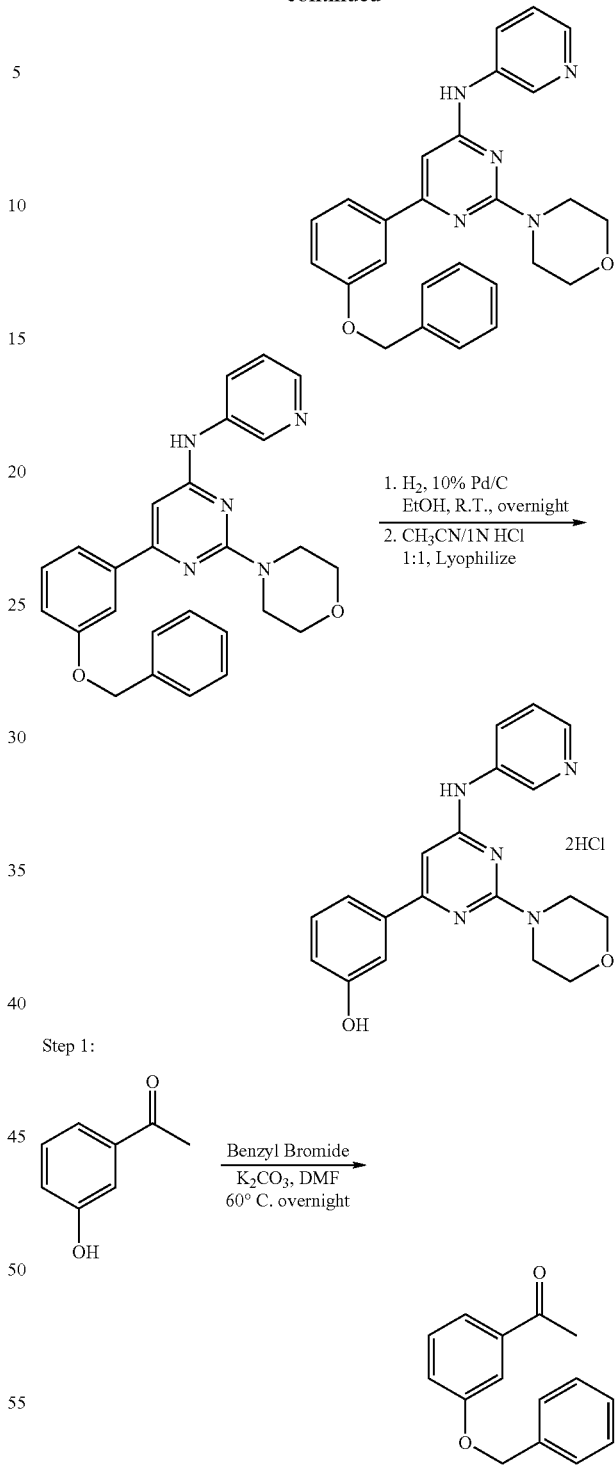

Step 1:

To a stirred solution of 3'-hydroxyacetophenone (1 eq) and benzyl bromide (1.5 eq) in dry DMF under $N_2$, solid $K_2CO_3$ (2 eq) was added in one portion. The reaction mixture was stirred at 60° C. for 3 days, then cooled down to room temperature. Most of the DMF was distilled off under reduced pressure. The residue was taken up in EtOAc and washed with 1N HCl, $H_2O$, Brine and dried ($Na_2SO_4$). Evaporation of the solvent under reduced pressure afforded a brown oil which was about a 1:1 mixture of the starting material and the desired product. The latter was isolated by chromatography on silica gel (EtOAc/Hexanes, 1:1) affording the desired 3'-benzyloxy acetophenone (51%). See for example: Schmidhammer, H.; Brossi, A. *J. Org. Chem.* 1983, 48, 1469.

TLC (silica gel, Ethyl acetate/hexanes 1:2, vanillin stain): $R_f$=0.58, orange brown ($R_f$ starting material=0.28).

$^1$H NMR (CDCl$_3$, 300 MHz): 7.6-7.1 (9H, m), 5.11 (2H, s, CH$_2$Ph); 2.59 (3H, s, CH$_3$).

Step 2:

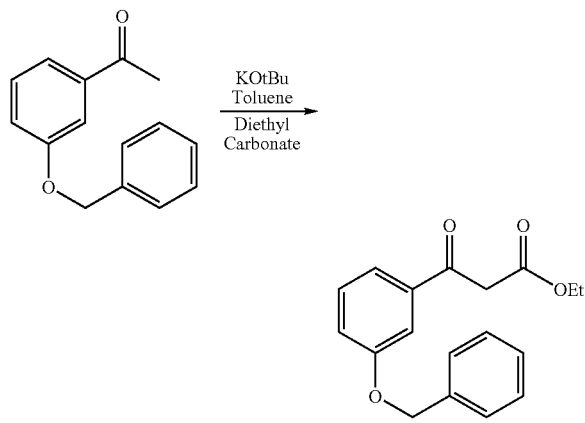

A round bottom flask, oven dried and kept under N$_2$ atmosphere, was charged with potassium tert-butoxide (2.2 eq) and dry toluene was added. The suspension was cooled down to 0° C. and a solution of 3'-benzyloxy acetophenone (1 eq) and diethylcarbonate (2 eq) in toluene was added dropwise via a dropping funnel, with vigorous stirring. During the addition the temperature should not raise above 10° C. After the end of the addition the reaction mixture was stirred at room temperature for 1 h and then at 60° C. overnight. The reaction mixture was again cooled down to room temperature and quenched with a 1:10 mixture of acetic acid and water. The addition must be slow and occasional cooling might be necessary to keep the temperature below 20° C. The two phases were separated and the aqueous phase was extracted with EtOAc (×3). The organic extracts were collected and dried (Na$_2$SO$_4$). After evaporation of the solvent under reduced pressure of crude ethyl 3-oxo-3-[3-(phenylmethoxy)phenyl]propanoate were obtained. The compound could be carried on to the next step without further purification.

TLC (silica gel, ethyl acetate/hexanes 1:5, vanillin stain): $R_f$=0.26, faint orange brown LC-MS (ion spray, 50 eV, m/z): 299 (M+H$^+$).

$^1$H NMR (CDCl$_3$, 300 MHz): 7.6-7.1 (9H, m); 5.10 (2H, bs, CH$_2$Ph); 4.21 (2H, q, J=7.2 Hz OCH$_2$); 3.96 (2H, s, COCH$_2$); 1.25 (3H, t, J=7.2 Hz, CH$_3$).

Step 3:

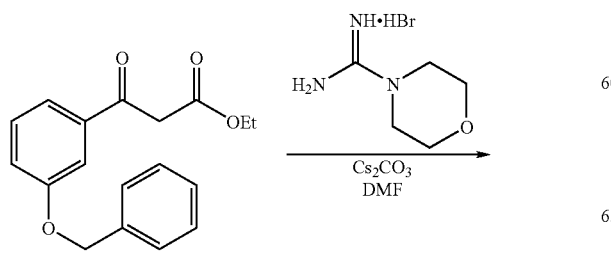

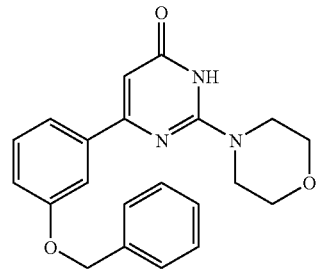

In a round bottom flask, oven dried and kept under N$_2$ atmosphere, Cs$_2$CO$_3$ (1.5 eq) was suspended in dry DMF. Morpholino formamidine hydrobromide (1.2 eq) was added, followed by ethyl 3-oxo-3-[3-(phenylmethoxy)phenyl]propanoate (1 eq). The reaction mixture was stirred at 115° C. overnight, then cooled down to room temperature. The DMF was distilled off under reduced pressure and the residue was taken up in water, neutralizing with 5% HCl solution. The aqueous phase was then extracted with CH$_2$Cl$_2$ (×5). The organic extracts were collected and dried (Na$_2$SO$_4$). After evaporation of the solvent under reduced pressure the desired 2-morpholin-4-yl-6-[3-(phenylmethoxy)phenyl]-3-hydropyrimidin-4-one were obtained as an off white solid (60%). The crude is already pure enough for the next step, but it can be purified further by trituration with acetonitrile.

TLC (silica gel, CH$_2$Cl$_2$/MeOH 1:10): $R_f$=0.32 ($R_f$ of the starting material=0.9).

LC-MS (ion spray, 50 eV, m/z): 364 (M+H$^+$).

$^1$H NMR (CDCl$_3$, 300 MHz): 7.65-7.3 (8H, m); 7.06 (1H, ddd, J=8.4, 2.7, 0.9 Hz); 6.25 (1H, s); 5.13 (2H, s, CH$_2$Ph); 3.83 (8H, bs, morpholine).

Step 4:

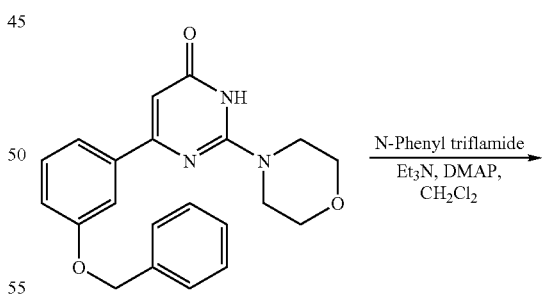

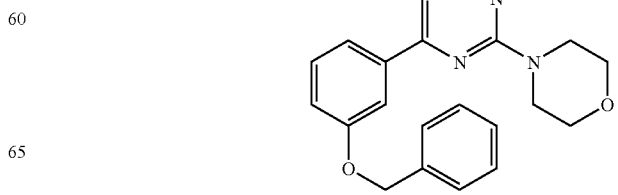

2-morpholin-4-yl-6-[3-(phenylmethoxy)phenyl]-3-hydropyrimidin-4-one (1 eq) was dissolved in CH₂Cl₂ in a round bottom flask, oven dried and kept under N₂ atmosphere. The compound is not completely soluble. Triethylamine was added (1.4 eq) followed by N-Phenyl trifluoromethanesulfonimide (1.2 eq) and DMAP (10 mol %). The reaction mixture was stirred at room temperature overnight, obtaining a bright orange solution. The solvent was evaporated under reduced pressure and the residue purified by chromatography on silica gel (ethyl acetate/hexanes 1:5), obtaining (99%) the desired 2-morpholin-4-yl-6-[3-(phenylmethoxy)phenyl]pyrimidin-4-yl (trifluoromethyl) sulfonate.

TLC (silica gel, EtOAc/Hexanes 1:5): R$_f$=0.31.

¹H NMR (CDCl₃, 300 MHz): 7.64 (1H, dd, J=2.4, 1.5 Hz); 7.55 (1H, app. dt, J=7.8, 1.2 Hz); 7.2-7.3 (6H, m); 7.12 (1H, ddd, J=8.4, 2.4, 0.9 Hz); 6.66 (1H, s, pyrimidine CH), 5.14 (2H, s, CH₂Ph), 3.86 (4H, bm, morpholine); 3.79 (4H, m, morpholine).

Step 5:

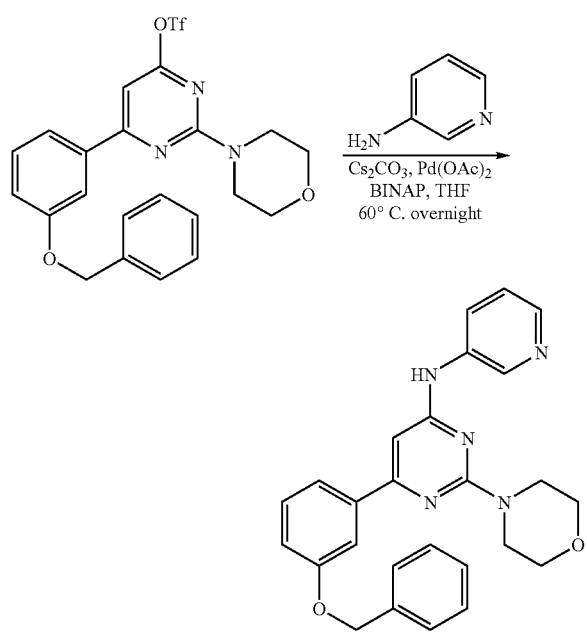

A round bottom flask, oven dried and kept under N₂ atmosphere was charged with Cs₂CO₃ (1.4 eq), Pd(OAc)₂ (5 mol %), and S-(−)-BINAP (1.5×mol of Pd catalyst). The flask was purged with N₂ for about 5-10 min and a solution of 2-morpholin-4-yl-6-[3-(phenylmethoxy)phenyl]pyrimidin-4-yl (trifluoromethyl)sulfonate (1 eq) in dry THF (20 mL) was added via a syringe, followed by 3-aminopyridine (2 eq,) in one portion. The flask was equipped with a reflux condenser, purged again with N₂ for 5 min and the reaction mixture was refluxed overnight. An efficient stirring is very important. The reaction mixture was cooled down to room temperature and the solvent was evaporated under reduced pressure. The residue was washed with water (×2) and triturated with methanol to afford the desired {2-morpholin-4-yl-6-[3-(phenylmethoxy)phenyl]pyrimidin-4-yl}-3-pyridylamine.

Step 6:

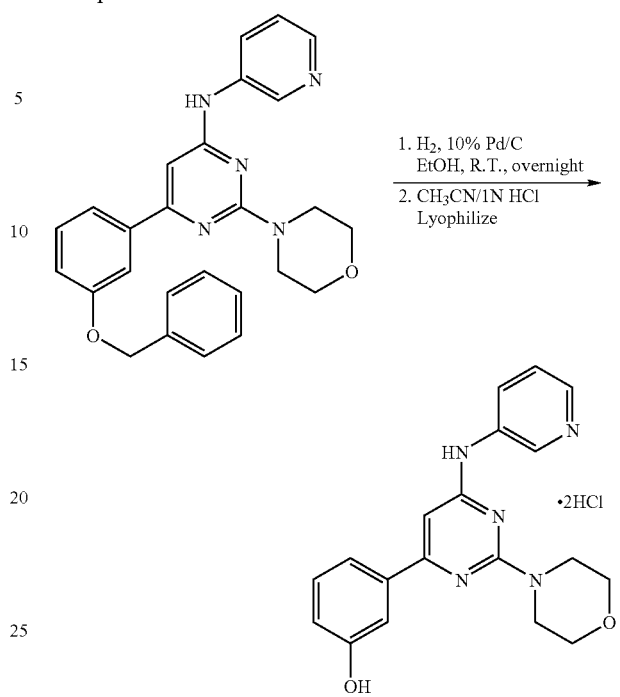

{2-Morpholin-4-yl-6-[3-(phenylmethoxy)phenyl]pyrimidin-4-yl}-3-pyridylamine (1 eq) is suspended in ethanol in a round bottom flask, purged with N₂. 10% Pd/C (20% wt) was added. The flask was evacuated and filled up with H₂ (contained in a balloon) for five times, then the reaction mixture was stirred under H₂ for 20 h. The catalyst was filtered off through a pad of celite washing thoroughly with EtOH, MeOH, CH₂Cl₂, and acetonitrile (almost one liter of the mixture of solvents was used to ensure the complete solubilization of the product). The solvent was evaporated under reduced pressure and the residue purified by reverse phase chromatography (Buffer A: 0.1% TFA in H₂O, Buffer B: 0.1% TFA in CH₃CN; Column: Waters, C18, 47×300 mm; gradient: 1.1%, 10%-60% B in 45 min). The free base thus obtained was lyophilized from a 1:1 mixture of acetonitrile and 1N HCl, obtaining the desired 3-[2-morpholin-4-yl-6-(3-pyridylamino)pyrimidin-4-yl]phenol as the bis HCl salt. The spectral data are the following:

HPLC: (Buffer A: 0.1% TFA in H₂O, Buffer B: 0.1% TFA in CH₃CN; Column: Waters, C18, 4.6×250 mm; gradient: 4.2%, 5%-80% B in 18 min) R$_t$=4.47.

LC-MS (ion spray, 50 eV, m/z): 350 (M+H⁺).

¹H NMR (DMSO+D₂O, 300 MHz): 9.22 (1H, bs), 8.37 (2H, app d, J=5.7), 7.79 (1H, dd, J=7.2, 5.4), 7.43, (2H, m). 7.30 (1H, app t, J=7.5), 6.89 (1H, dd, J=7.0, 2.1), 6.59 (1H, s), 3.6-3.8 (8H, m).

Compounds of the following Examples were synthesized following the synthetic method described above in Methods 1 and 2. The precursors are readily recognizable by one skilled in the art and are commercially available from Aldrich (Milwaukee, Wis.), Acros Organics (Pittsburgh, Pa.), Biosynth International (Naperville, Ill.), Asymchem International, Inc. (Durham, N.C.) Maybridge Chemical Company Ltd. (Cornwall), and/or UK Peakdale Molecular (High Peak, UK).

The compounds were named using ACD/Name v. 5.04, 2001 and Nomenclator (v. 6.0) from ChemInovation Software, Inc.

| Example | Structure | Name | LC/MS m/z (MH+) |
|---|---|---|---|
| 2 | 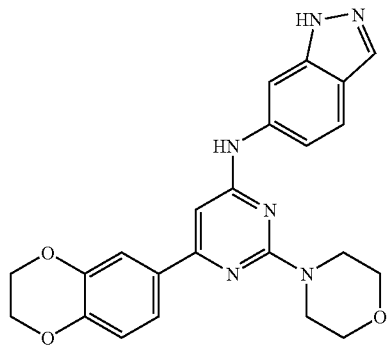 | N-[6-(2,3-dihydro-1,4-benzodioxin-6-yl)-2-morpholin-4-ylpyrimidin-4-yl]-1H-indazol-6-amine | 431.5 |
| 3 | 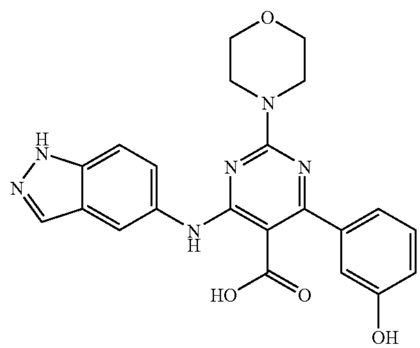 | 4-(3-hydroxyphenyl)-6-(1H-indazol-5-ylamino)-2-morpholin-4-ylpyrimidine-5-carboxylic acid | 433.4 |
| 4 | 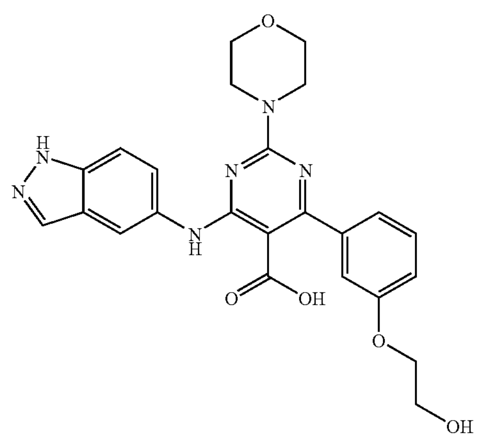 | 4-[3-(2-hydroxyethoxy)phenyl]-6-(1H-indazol-5-ylamino)-2-morpholin-4-ylpyrimidine-5-carboxylic acid | 477.5 |
| 5 | 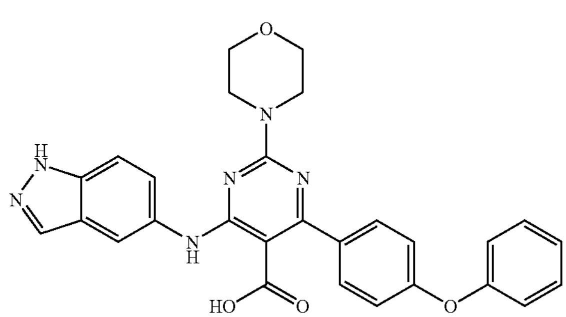 | 4-(1H-indazol-5-ylamino)-2-morpholin-4-yl-6-(4-phenoxyphenyl)pyrimidine-5-carboxylic acid | 509.5 |

-continued
| Example | Structure | Name | LC/MS m/z (MH+) |
|---|---|---|---|
| 6 | 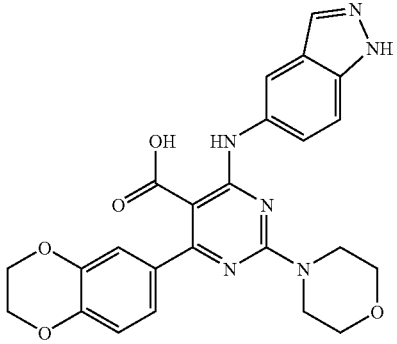 | 4-(2,3-dihydro-1,4-benzodioxin-6-yl)-6-(1H-indazol-5-ylamino)-2-morpholin-4-ylpyrimidine-5-carboxylic acid | 475.5 |
| 7 | 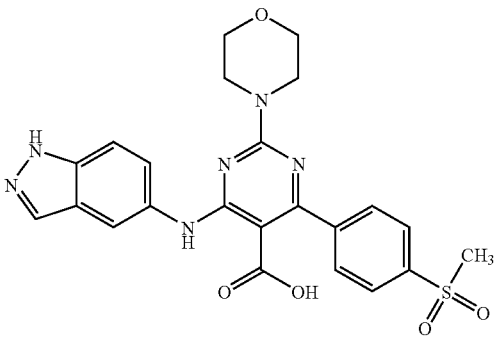 | 4-(1H-indazol-5-ylamino)-6-[4-(methylsulfonyl)phenyl]-2-morpholin-4-ylpyrimidine-5-carboxylic acid | 495.5 |
| 8 | 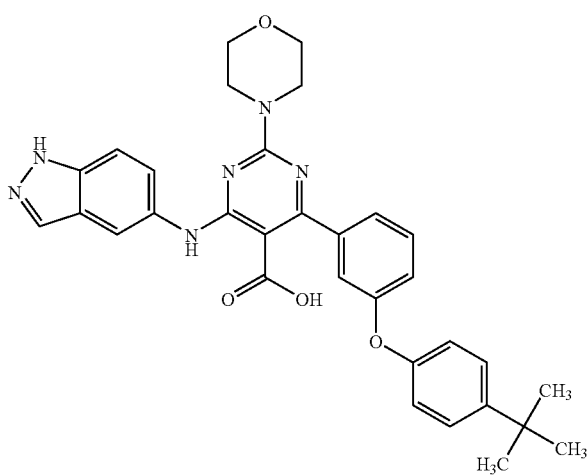 | 4-[3-(4-tert-butylphenoxy)phenyl]-6-(1H-indazol-5-ylamino)-2-morpholin-4-ylpyrimidine-5-carboxylic acid | 565.6 |

-continued

| Example | Structure | Name | LC/MS m/z (MH+) |
|---|---|---|---|
| 9 | 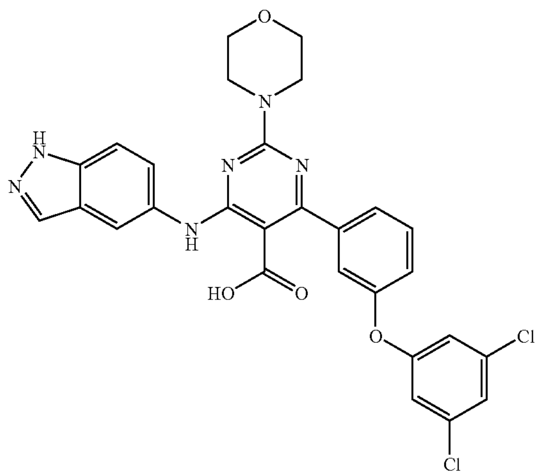 | 4-[3-(3,5-dichlorophenoxy)phenyl]-6-(1H-indazol-5-ylamino)-2-morpholin-4-ylpyrimidine-5-carboxylic acid | 578.4 |
| 10 | 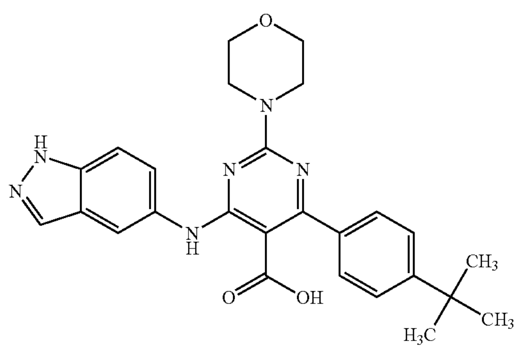 | 4-(4-tert-butylphenyl)-6-(1H-indazol-5-ylamino)-2-morpholin-4-ylpyrimidine-5-carboxylic acid | 473.5 |
| 11 | 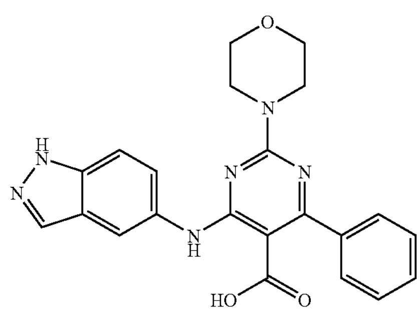 | 4-(1H-indazol-5-ylamino)-2-morpholin-4-yl-6-phenylpyrimidine-5-carboxylic acid | 417.4 |
| 11a | 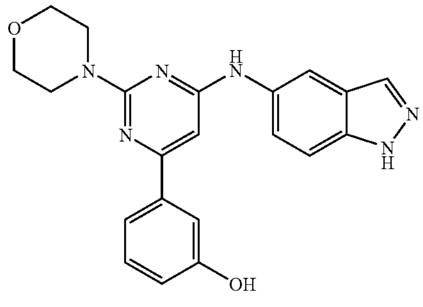 | | |

-continued

| Example | Structure | Name | LC/MS m/z (MH+) |
|---|---|---|---|
| 12 | 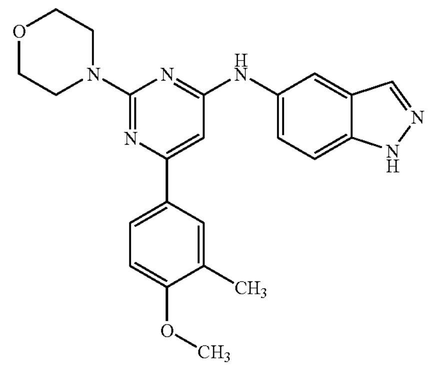 | N-[6-(4-methoxy-3-methylphenyl)-2-morpholin-4-ylpyrimidin-4-yl]-1H-indazol-5-amine | 417.5 |
| 13 | 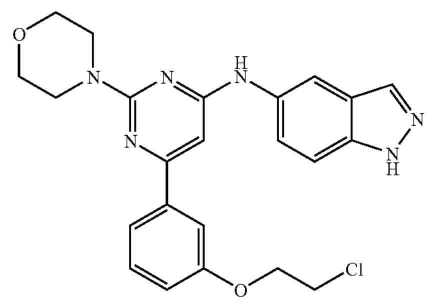 | 2-{3-[6-(1H-indazol-5-ylamino)-2-morpholin-4-ylpyrimidin-4-yl]phenoxy}ethanol | 433.5 |
| 14 | 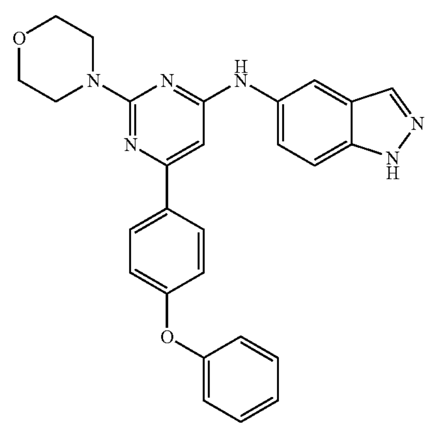 | N-[2-morpholin-4-yl-6-(4-phenoxyphenyl)pyrimidin-4-yl]-1H-indazol-5-amine | 465.5 |
| 15 | 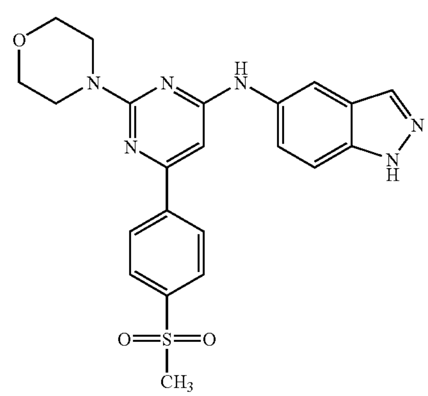 | N-{6-[4-(methylsulfonyl)phenyl]-2-morpholin-4-ylpyrimidin-4-yl}-1H-indazol-5-amine | 451.5 |

-continued

| Example | Structure | Name | LC/MS m/z (MH+) |
|---|---|---|---|
| 16 | 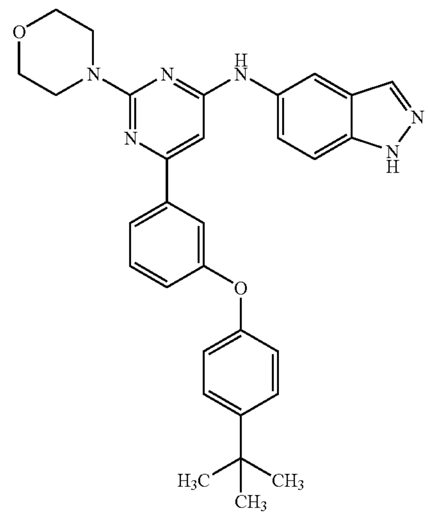 | N-{6-[3-(4-tert-butylphenoxy)phenyl]-2-morpholin-4-ylpyrimidin-4-yl}-1H-indazol-5-amine | 521.6 |
| 17 | 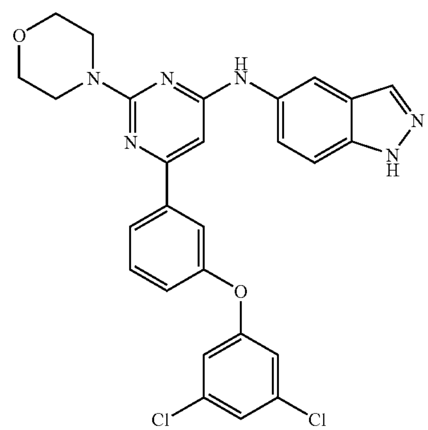 | N-{6-[3-(3,5-dichlorophenoxy)phenyl]-2-morpholin-4-ylpyrimidin-4-yl}-1H-indazol-5-amine | 534.4 |
| 18 | 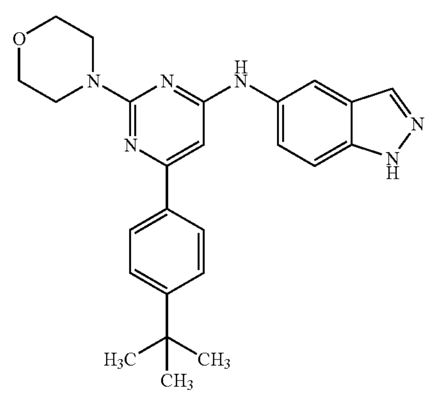 | N-[6-(4-tert-butylphenyl)-2-morpholin-4-ylpyrimidin-4-yl]-1H-indazol-5-amine | 429.5 |

-continued

| Example | Structure | Name | LC/MS m/z (MH+) |
|---|---|---|---|
| 19 | 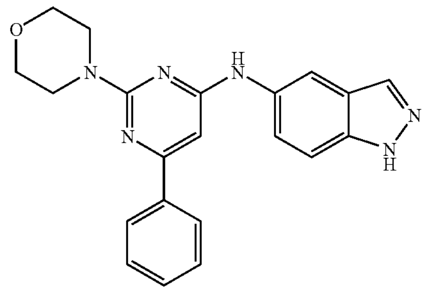 | N-(2-morpholin-4-yl-6-phenylpyrimidin-4-yl)-1H-indazol-5-amine | 373.4 |
| 20 | 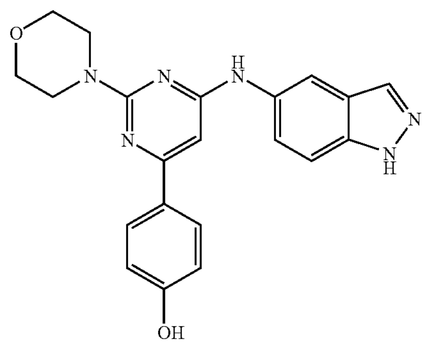 | 4-[6-(1H-indazol-5-ylamino)-2-morpholin-4-ylpyrimidin-4-yl]phenol | 389.4 |
| 21 | 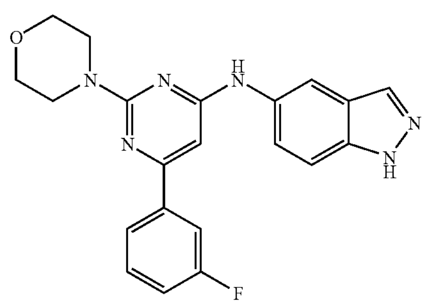 | N-[6-(3-fluorophenyl)-2-morpholin-4-ylpyrimidin-4-yl]-1H-indazol-5-amine | 391.4 |
| 22 | 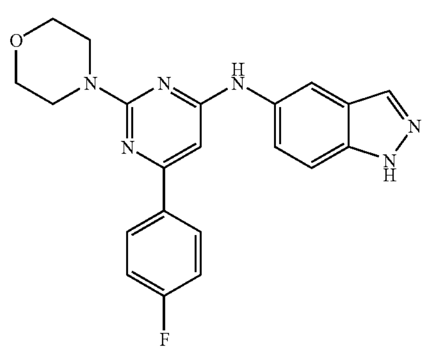 | N-[6-(4-fluorophenyl)-2-morpholin-4-ylpyrimidin-4-yl]-1H-indazol-5-amine | 391.4 |

-continued

| Example | Structure | Name | LC/MS m/z (MH+) |
|---|---|---|---|
| 23 | 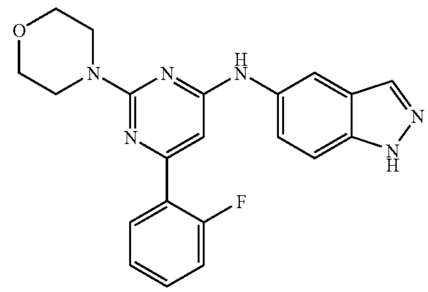 | N-[6-(2-fluorophenyl)-2-morpholin-4-ylpyrimidin-4-yl]-1H-indazol-5-amine | 391.4 |
| 24 | 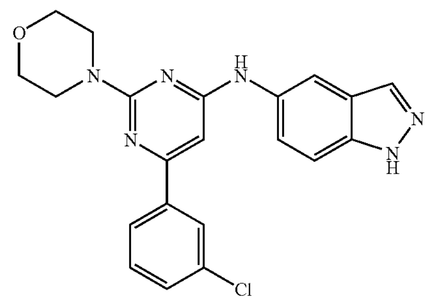 | N-[6-(3-chlorophenyl)-2-morpholin-4-ylpyrimidin-4-yl]-1H-indazol-5-amine | 407.9 |
| 25 | 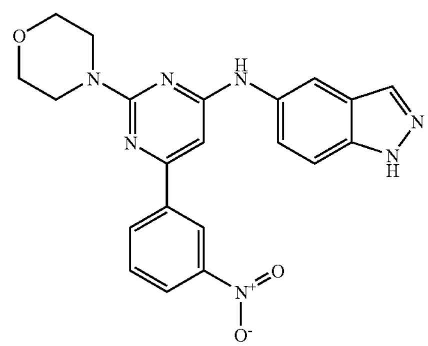 | N-[2-morpholin-4-yl-6-(3-nitrophenyl)pyrimidin-4-yl]-1H-indazol-5-amine | 418.4 |
| 26 | 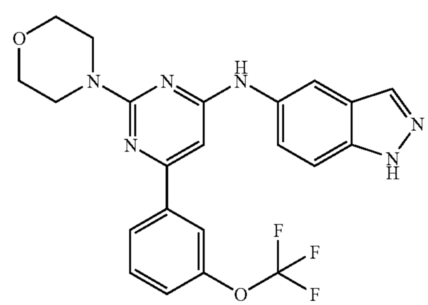 | N-{2-morpholin-4-yl-6-[3-(trifluoromethoxy)phenyl]pyrimidin-4-yl}-1H-indazol-5-amine | 457.4 |

| Example | Structure | Name | LC/MS m/z (MH+) |
|---|---|---|---|
| 27 | 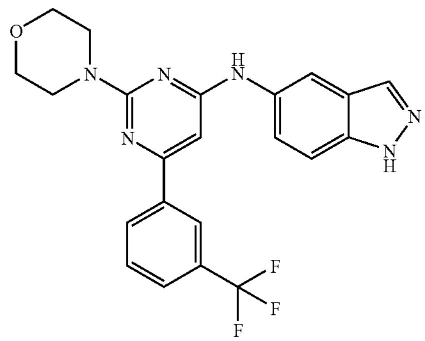 | N-{2-morpholin-4-yl-6-[3-(trifluoromethyl)phenyl]pyrimidin-4-yl}-1H-indazol-5-amine | 441.4 |
| 28 | 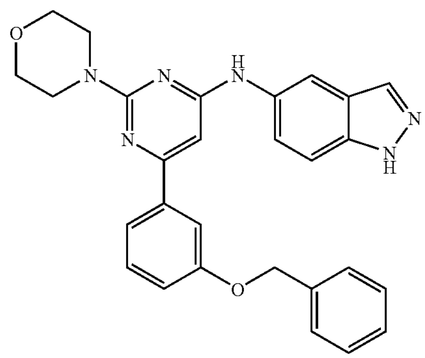 | N-{6-[3-(benzyloxy)phenyl]-2-morpholin-4-ylpyrimidin-4-yl}-1H-indazol-5-amine | 479.6 |
| 29 | 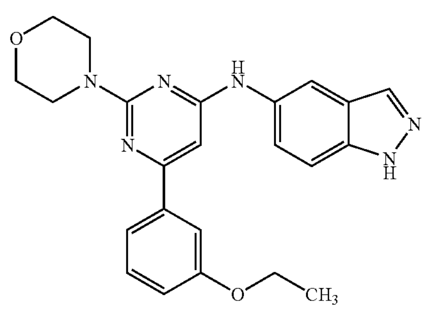 | N-[6-(3-ethoxyphenyl)-2-morpholin-4-ylpyrimidin-4-yl]-1H-indazol-5-amine | 417.5 |
| 30 | 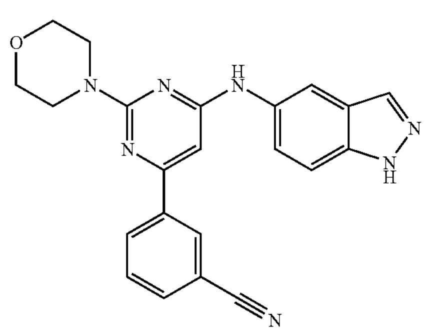 | 3-[6-(1H-indazol-5-ylamino)-2-morpholin-4-ylpyrimidin-4-yl]benzonitrile | 398.4 |

| Example | Structure | Name | LC/MS m/z (MH+) |
|---|---|---|---|
| 31 | 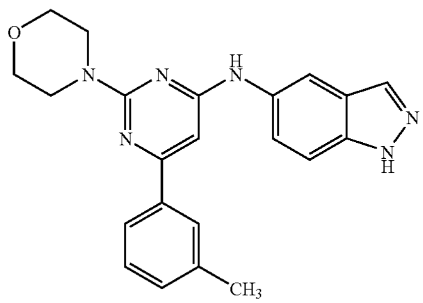 | N-[6-(3-methylphenyl)-2-morpholin-4-ylpyrimidin-4-yl]-1H-indazol-5-amine | 387.5 |
| 32 | 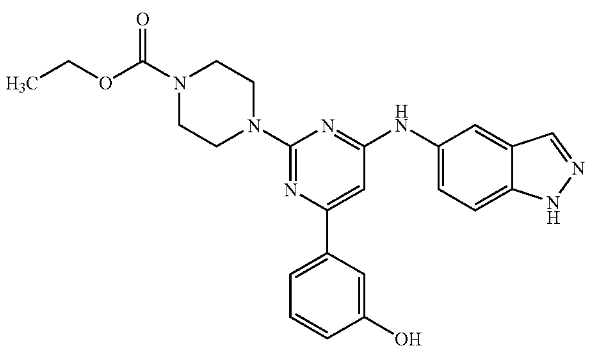 | ethyl 4-[4-(3-hydroxyphenyl)-6-(1H-indazol-5-ylamino)pyrimidin-2-yl]piperazine-1-carboxylate | 460.5 |
| 33 | 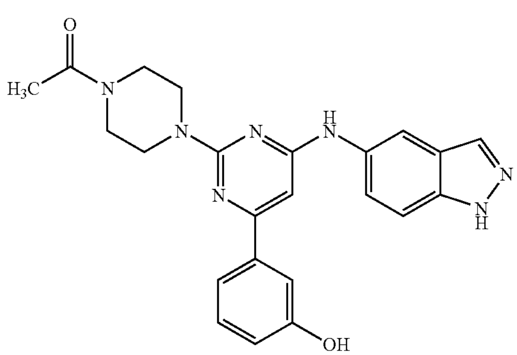 | 3-[2-(4-acetylpiperazin-1-yl)-6-(1H-indazol-5-ylamino)pyrimidin-4-yl]phenol | 430.5 |
| 34 | 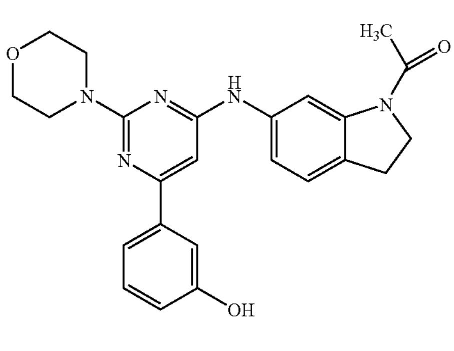 | 3-{6-[(1-acetyl-2,3-dihydro-1H-indol-6-yl)amino]-2-morpholin-4-ylpyrimidin-4-yl}phenol | 432.5 |

-continued

| Example | Structure | Name | LC/MS m/z (MH+) |
|---|---|---|---|
| 35 | 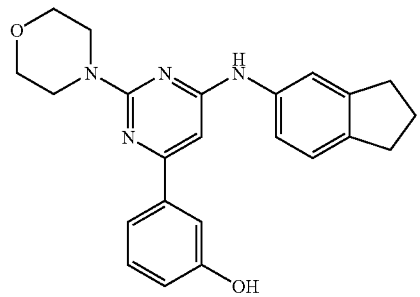 | 3-[6-(2,3-dihydro-1H-inden-5-ylamino)-2-morpholin-4-ylpyrimidin-4-yl]phenol | 389.5 |
| 36 | 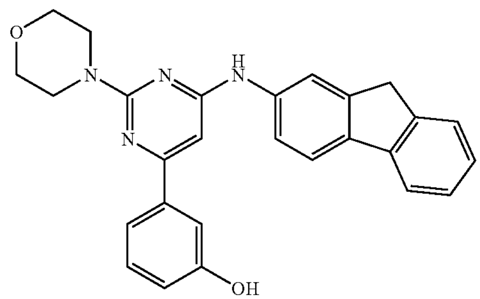 | 3-[6-(9H-fluoren-2-ylamino)-2-morpholin-4-ylpyrimidin-4-yl]phenol | 437.5 |
| 37 | 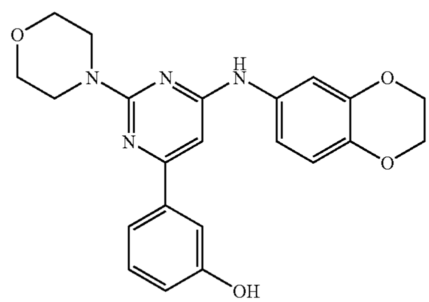 | 3-[6-(2,3-dihydro-1,4-benzodioxin-6-ylamino)-2-morpholin-4-ylpyrimidin-4-yl]phenol | 407.4 |
| 38 | 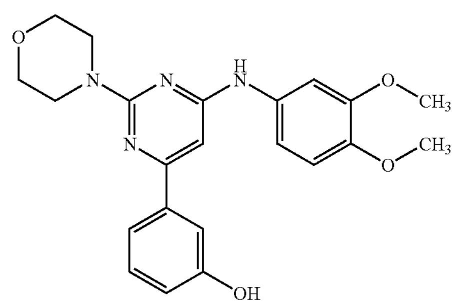 | 3-{6-[(3,4-dimethoxyphenyl)amino]-2-morpholin-4-ylpyrimidin-4-yl}phenol | 409.5 |
| 39 | 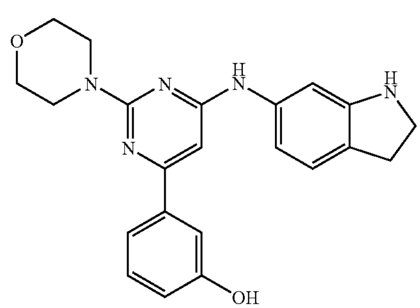 | 3-[6-(2,3-dihydro-1H-indol-6-ylamino)-2-morpholin-4-ylpyrimidin-4-yl]phenol | 390.5 |

-continued

| Example | Structure | Name | LC/MS m/z (MH+) |
|---|---|---|---|
| 40 | 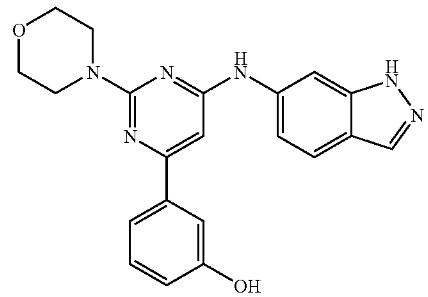 | 3-[6-(1H-indazol-6-ylamino)-2-morpholin-4-ylpyrimidin-4-yl]phenol | 389.4 |
| 41 | 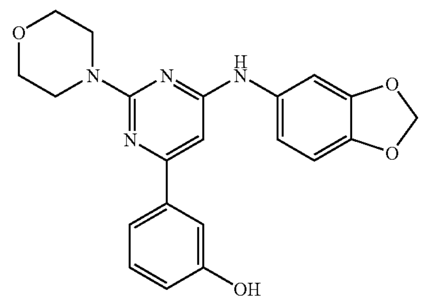 | 3-[6-(1,3-benzodioxol-5-ylamino)-2-morpholin-4-ylpyrimidin-4-yl]phenol | 393.4 |
| 42 | 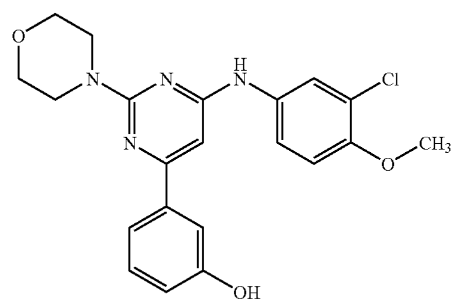 | 3-{6-[(3-chloro-4-methoxyphenyl)amino]-2-morpholin-4-ylpyrimidin-4-yl}phenol | 413.9 |
| 43 | 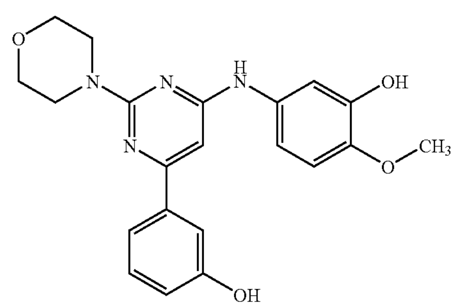 | 5-{[6-(3-hydroxyphenyl)-2-morpholin-4-ylpyrimidin-4-yl]amino}-2-methoxyphenol | 395.4 |
| 44 | 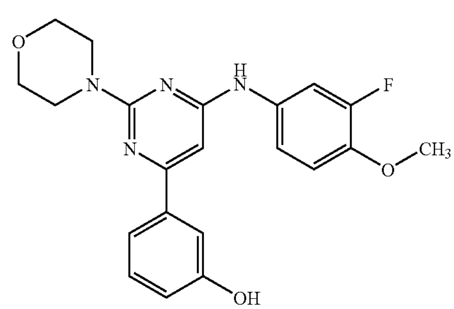 | 3-{6-[(3-fluoro-4-methoxyphenyl)amino]-2-morpholin-4-ylpyrimidin-4-yl}phenol | 397.4 |

| Example | Structure | Name | LC/MS m/z (MH+) |
|---|---|---|---|
| 45 | 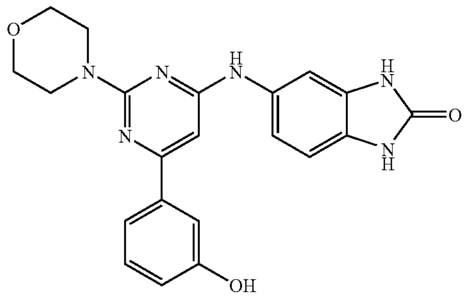 | 5-{[6-(3-hydroxyphenyl)-2-morpholin-4-ylpyrimidin-4-yl]amino}-1,3-dihydro-2H-benzimidazol-2-one | 405.4 |
| 46 | 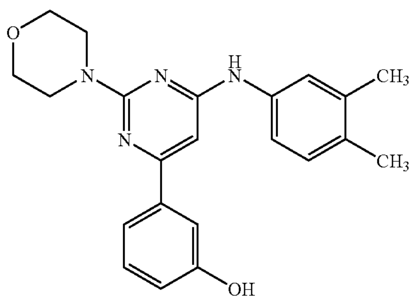 | 3-{6-[(3,4-dimethylphenyl)amino]-2-morpholin-4-ylpyrimidin-4-yl}phenol | 377.5 |
| 47 | 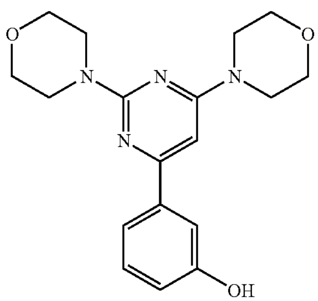 | 3-(2,6-dimorpholin-4-pyrimidin-4-yl)phenol | 343.4 |
| 48 | 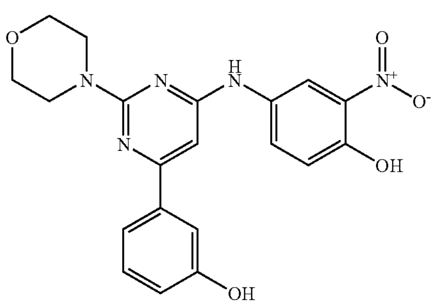 | 4-{[6-(3-hydroxyphenyl)-2-morpholin-4-ylpyrimidin-4-yl]amino}-2-nitrophenol | 410.4 |
| 49 | 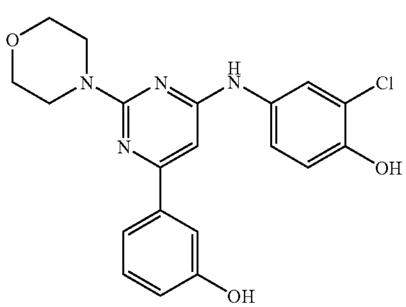 | 2-chloro-4-{[6-(3-hydroxyphenyl)-2-morpholin-4-ylpyrimidin-4-yl]amino}phenol | 399.8 |

-continued

| Example | Structure | Name | LC/MS m/z (MH+) |
|---|---|---|---|
| 50 | 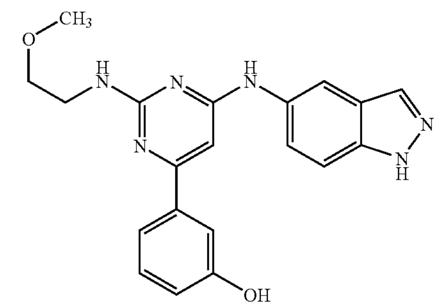 | 3-{6-(1H-indazol-5-ylamino)-2-[(2-methoxyethyl)amino]pyrimidin-4-yl}phenol | 377.4 |
| 51 | 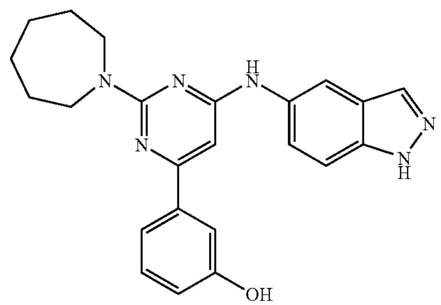 | 3-[2-azepan-1-yl-6-(1H-indazol-5-ylamino)pyrimidin-4-yl]phenol | 401.5 |
| 52 | 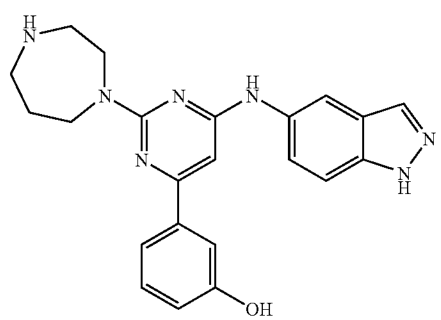 | 3-[2-(1,4-diazepan-1-yl)-6-(1H-indazol-5-ylamino)pyrimidin-4-yl]phenol | 402.5 |
| 53 | 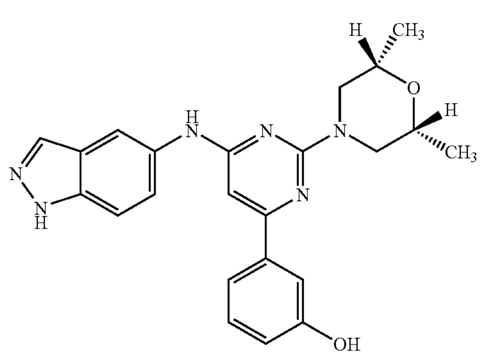 | 3-[2-[(2R,6S)-2,6-dimethylmorpholin-4-yl]-6-(1H-indazol-5-ylamino)pyrimidin-4-yl]phenol | 417.5 |

-continued

| Example | Structure | Name | LC/MS m/z (MH+) |
|---|---|---|---|
| 54 | 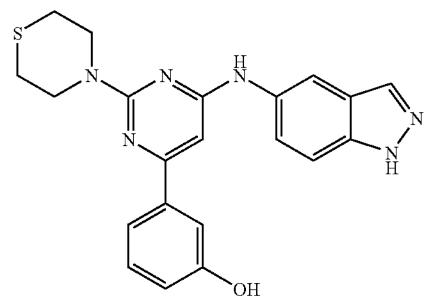 | 3-[6-(1H-indazol-5-ylamino)-2-thiomorpholin-4-ylpyrimidin-4-yl]phenol | 405.5 |
| 55 | 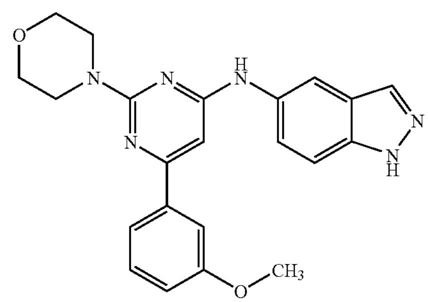 | N-[6-(3-methoxyphenyl)-2-morpholin-4-ylpyrimidin-4-yl]-1H-indazol-5-amine | 403.5 |
| 56 | 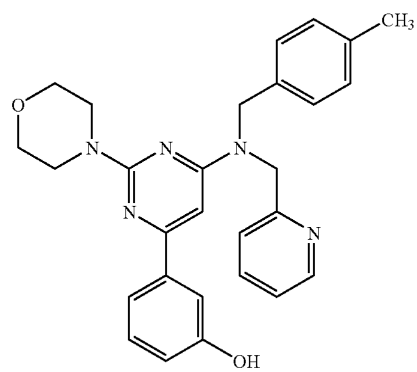 | 3-{6-[(4-methylbenzyl)(pyridin-2-ylmethyl)amino]-2-morpholin-4-ylpyrimidin-4-yl}phenol | 468.6 |
| 57 | 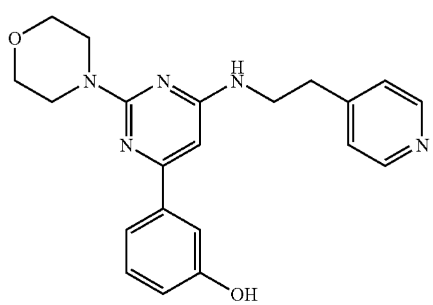 | 3-{2-morpholin-4-yl-6-[(2-pyridin-4-ylethyl)amino]pyrimidin-4-yl}phenol | 378.4 |

-continued

| Example | Structure | Name | LC/MS m/z (MH+) |
|---|---|---|---|
| 58 | 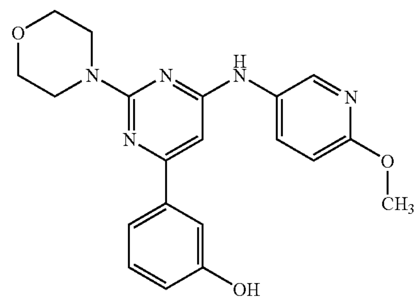 | 3-{6-[(6-methoxypyridin-3-yl)amino]-2-morpholin-4-ylpyrimidin-4-yl}phenol | 380.4 |
| 59 | 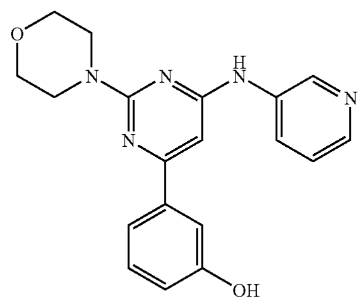 | 3-[2-morpholin-4-yl-6-(pyridin-3-ylamino)pyrimidin-4-yl]phenol | 350.4 |
| 60 | 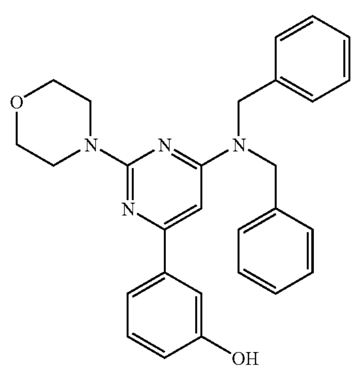 | 3-[6-(dibenzylamino)-2-morpholin-4-ylpyrimidin-4-yl]phenol | 453.6 |
| 61 | 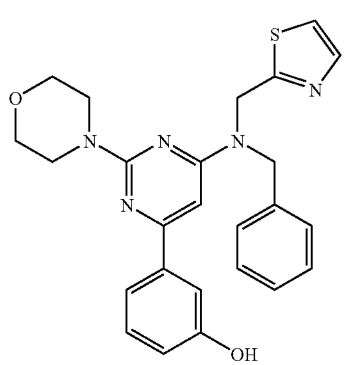 | 3-{6-[benzyl(1,3-thiazol-2-ylmethyl)amino]-2-morpholin-4-ylpyrimidin-4-yl}phenol | 460.6 |

-continued
| Example | Structure | Name | LC/MS m/z (MH+) |
|---|---|---|---|
| 62 | 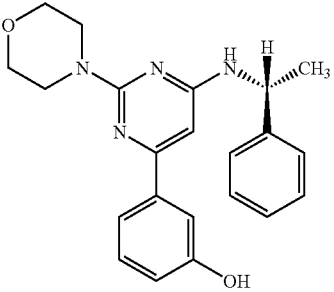 Chiral | 3-(2-morpholin-4-yl-6-{[(1R)-1-phenylethyl]amino}pyrimidin-4-yl)phenol | 377.5 |
| 63 | 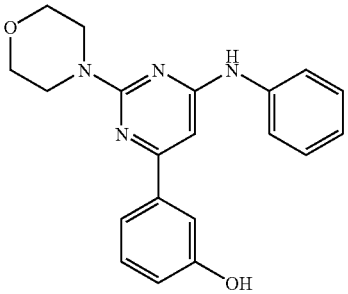 | 3-(6-anilino-2-morpholin-4-ylpyrimidin-4-yl)phenol | 349.4 |
| 64 | 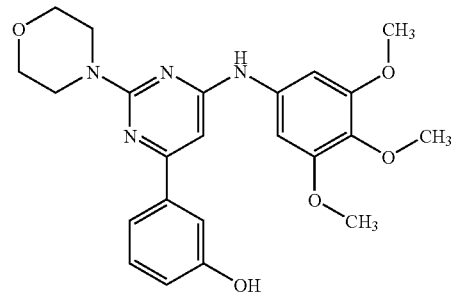 | 3-{2-morpholin-4-yl-6-[(3,4,5-trimethoxyphenyl)amino]pyrimidin-4-yl}phenol | 439.5 |
| 65 | 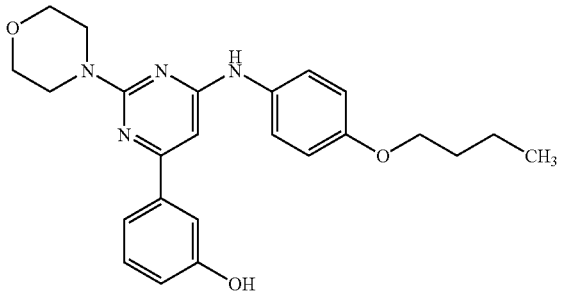 | 3-{6-[(4-butoxyphenyl)amino]-2-morpholin-4-ylpyrimidin-4-yl}phenol | 421.5 |
| 66 | 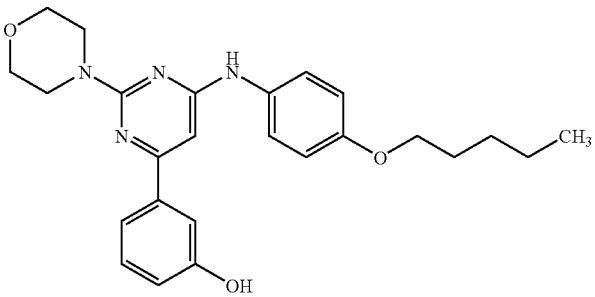 | 3-(2-morpholin-4-yl-6-{[4-(pentyloxy)phenyl]amino}pyrimidin-4-yl)phenol | 435.5 |

-continued

| Example | Structure | Name | LC/MS m/z (MH+) |
|---|---|---|---|
| 67 | 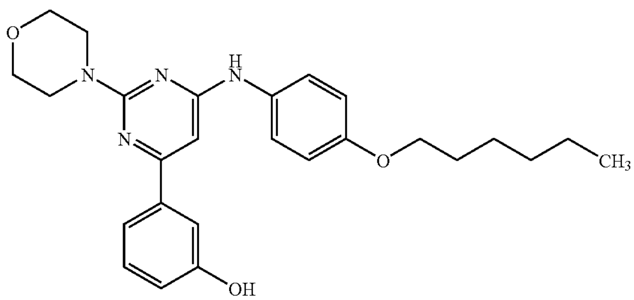 | 3-(6-{[4-(hexyloxy)phenyl]amino}-2-morpholin-4-ylpyrimidin-4-yl)phenol | 449.6 |
| 68 | 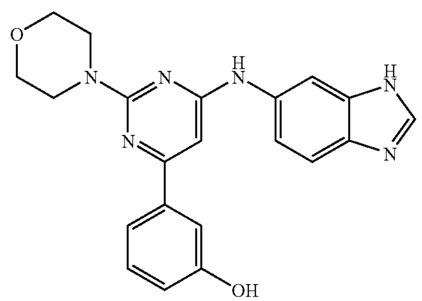 | 3-[6-(1H-benzimidazol-6-ylamino)-2-morpholin-4-ylpyrimidin-4-yl]phenol | 389.4 |
| 69 | 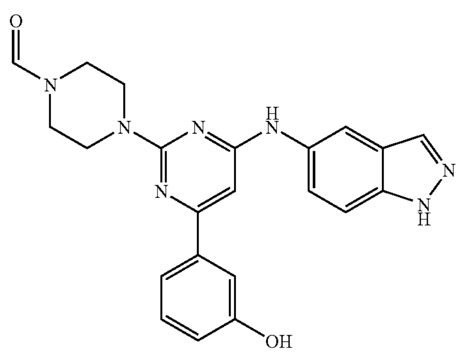 | 4-[4-(3-hydroxyphenyl)-6-(1H-indazol-5-ylamino)pyrimidin-2-yl]piperazine-1-carbaldehyde | 416.5 |
| 70 | 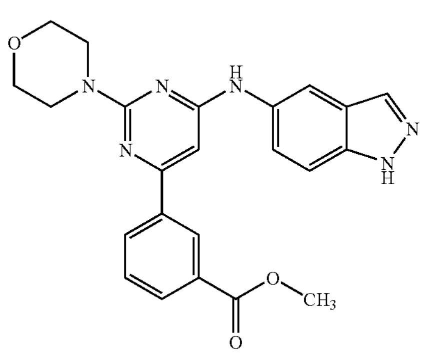 | methyl 3-[6-(1H-indazol-5-ylamino)-2-morpholin-4-ylpyrimidin-4-yl]benzoate | 431.5 |

-continued

| Example | Structure | Name | LC/MS m/z (MH+) |
|---|---|---|---|
| 71 | 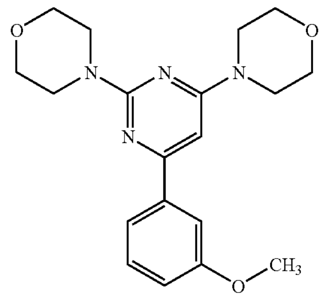 | 4-[4-(3-methoxyphenyl)-6-morpholin-4-ylpyrimidin-2-yl]morpholine | 357.4 |
| 72 | 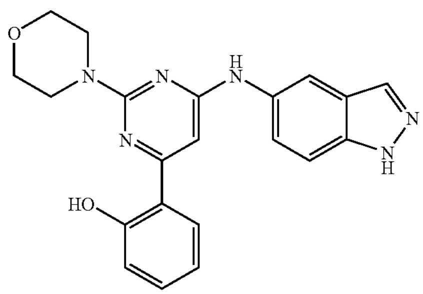 | 2-[6-(1H-indazol-5-ylamino)-2-morpholin-4-ylpyrimidin-4-yl]phenol | 389.4 |
| 73 | 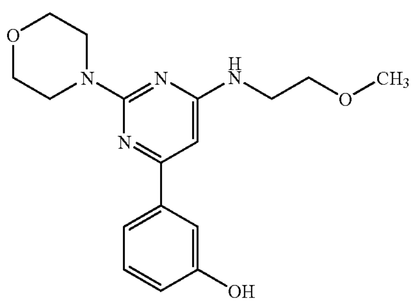 | 3-{6-[(2-methoxyethyl)amino]-2-morpholin-4-ylpyrimidin-4-yl}phenol | 331.4 |
| 74 | 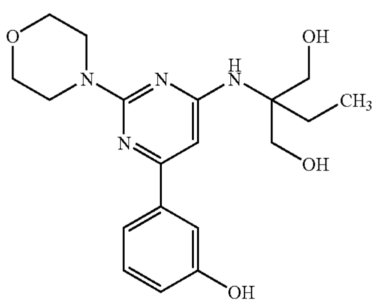 | 2-ethyl-2-{[6-(3-hydroxyphenyl)-2-morpholin-4-ylpyrimidin-4-yl]amino}propane-1,3-diol | 375.4 |
| 75 | 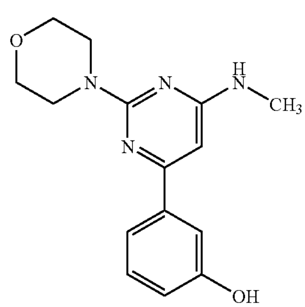 | 3-[6-(methylamino)-2-morpholin-4-ylpyrimidin-4-yl]phenol | 287.3 |

-continued

| Example | Structure | Name | LC/MS m/z (MH+) |
|---|---|---|---|
| 76 | 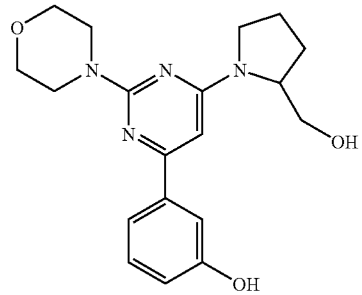 | 3-{6-[2-(hydroxymethyl)pyrrolidin-1-yl]-2-morpholin-4-ylpyrimidin-4-yl}phenol | 357.4 |
| 77 | 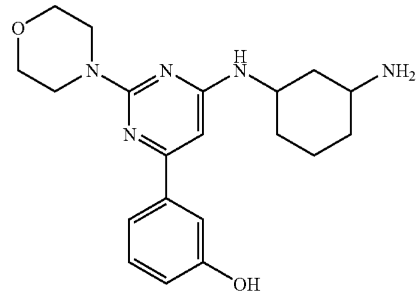 | 3-{6-[(3-aminocyclohexyl)amino]-2-morpholin-4-ylpyrimidin-4-yl}phenol | 370.5 |
| 78 | Chiral | 3-(6-{[(1R,2R)-2-aminocyclohexyl]amino}-2-morpholin-4-ylpyrimidin-4-yl)phenol | 370.5 |
| 79 | 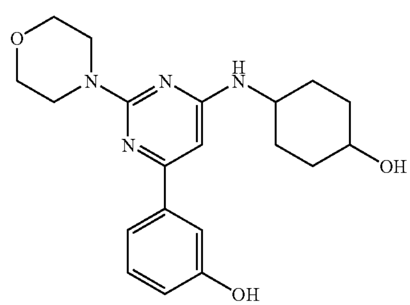 | 3-{6-[(4-hydroxycyclohexyl)amino]-2-morpholin-4-ylpyrimidin-4-yl)phenol | 371.4 |
| 80 | 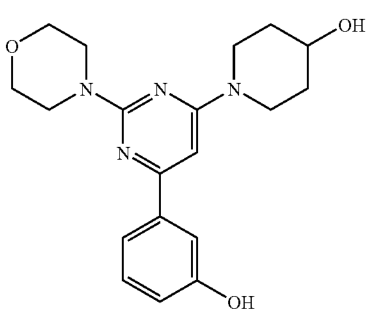 | 1-[6-(3-hydroxyphenyl)-2-morpholin-4-ylpyrimidin-4-yl]piperidin-4-ol | 357.4 |

-continued

| Example | Structure | Name | LC/MS m/z (MH+) |
|---|---|---|---|
| 81 | 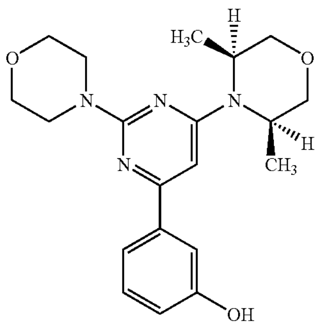 | 3-{6-[(3R,5S)-3,5-dimethylmorpholin-4-yl]-2-morpholin-4-ylpyrimidin-4-yl}phenol | 371.4 |
| 82 | 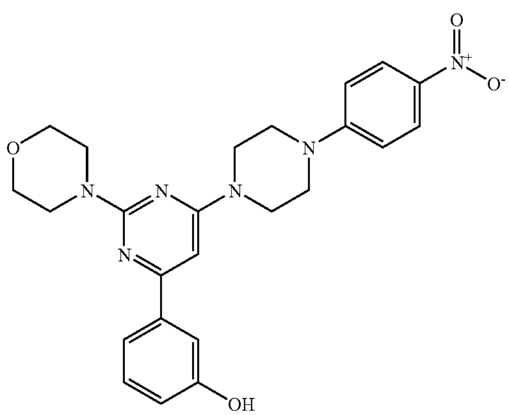 | 3-{2-morpholin-4-yl-6-[4-(4-nitrophenyl)piperazin-1-yl]pyrimidin-4-yl}phenol | 463.5 |
| 83 | 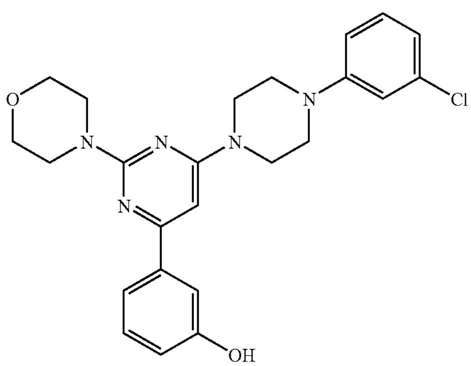 | 3-{6-[4-(3-chlorophenyl)piperazin-1-yl]-2-morpholin-4-ylpyrimidin-4-yl}phenol | 453.0 |
| 84 | 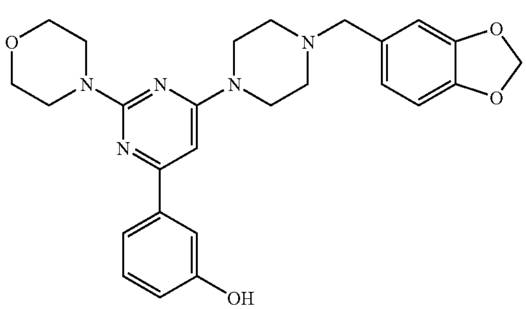 | 3-{6-[4-(1,3-benzodioxol-5-ylmethyl)piperazin-1-yl]-2-morpholin-4-ylpyrimidin-4-yl}phenol | 476.5 |

-continued

| Example | Structure | Name | LC/MS m/z (MH+) |
|---|---|---|---|
| 85 | 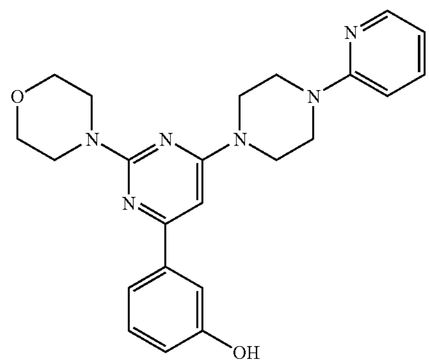 | 3-[2-morpholin-4-yl-6-(4-pyridin-2-ylpiperazin-1-yl)pyrimidin-4-yl]phenol | 419.5 |
| 86 | 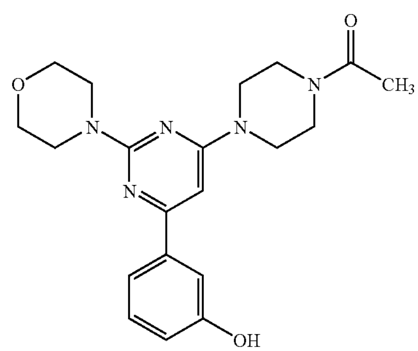 | 3-[6-(4-acetylpiperazin-1-yl)-2-morpholin-4-ylpyrimidin-4-yl]phenol | 384.4 |
| 87 | 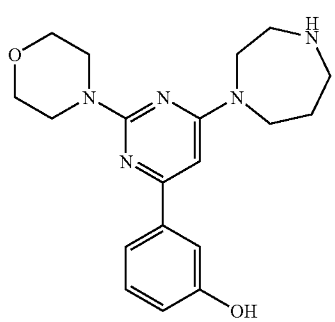 | 3-[6-(1,4-diazepan-1-yl)-2-morpholin-4-ylpyrimidin-4-yl]phenol | 356.4 |
| 88 | 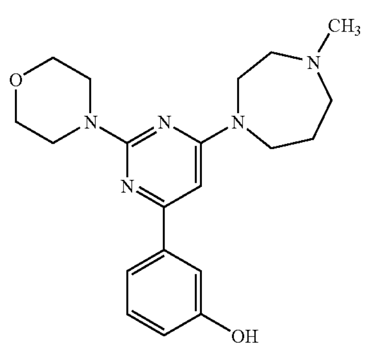 | 3-[6-(4-methyl-1,4-diazepan-1-yl)-2-morpholin-4-ylpyrimidin-4-yl]phenol | 370.5 |

| Example | Structure | Name | LC/MS m/z (MH+) |
|---|---|---|---|
| 89 | 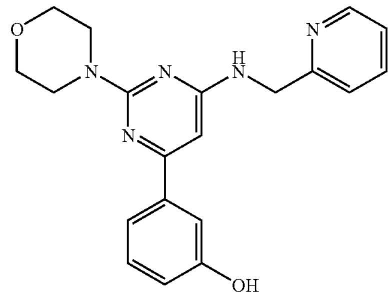 | 3-{2-morpholin-4-yl-6-[(pyridin-2-ylmethyl)amino]pyrimidin-4-yl}phenol | 364.4 |
| 90 | 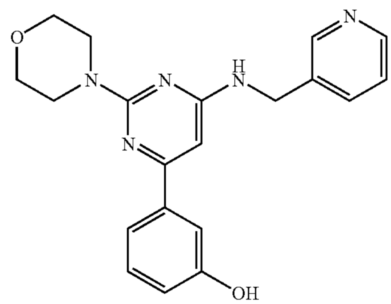 | 3-{2-morpholin-4-yl-6-[(pyridin-3-ylmethyl)amino]pyrimidin-4-yl}phenol | 364.4 |
| 91 | 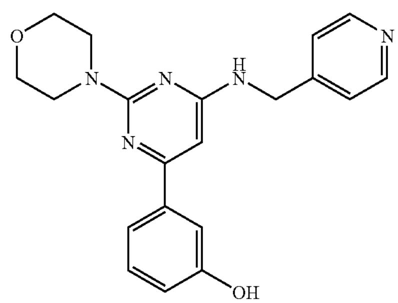 | 3-{2-morpholin-4-yl-6-[(pyridin-4-ylmethyl)amino]pyrimidin-4-yl}phenol | 364.4 |
| 92 | 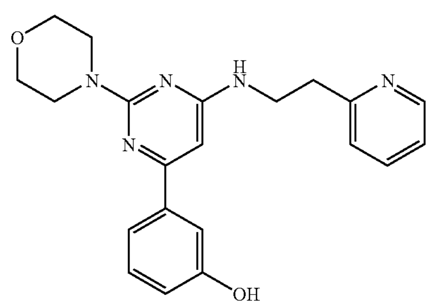 | 3-{2-morpholin-4-yl-6-[(2-pyridin-2-ylethyl)amino]pyrimidin-4-yl}phenol | 378.4 |
| 93 | 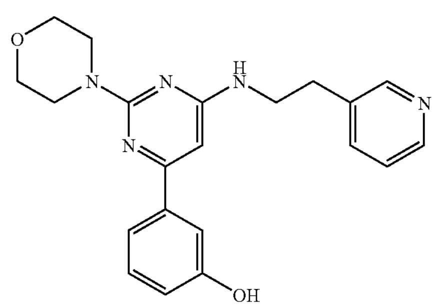 | 3-{2-morpholin-4-yl-6-[(2-pyridin-3-ylethyl)amino]pyrimidin-4-yl}phenol | 378.4 |

-continued

| Example | Structure | Name | LC/MS m/z (MH+) |
|---|---|---|---|
| 94 | 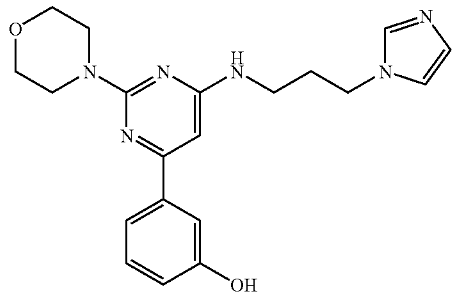 | 3-(6-{[3-(1H-imidazol-1-yl)propyl]amino}-2-morpholin-4-ylpyrimidin-4-yl)phenol | 381.4 |
| 95 | 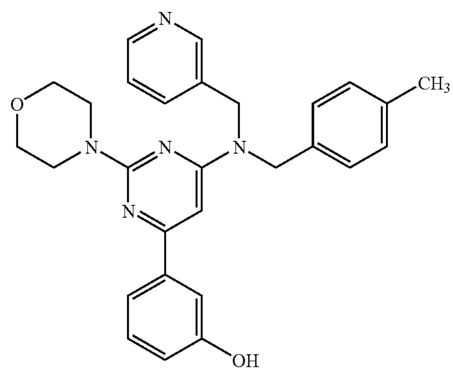 | 3-{6-[(4-methylbenzyl)(pyridin-3-ylmethyl)amino]-2-morpholin-4-ylpyrimidin-4-yl}phenol | 468.6 |
| 96 | 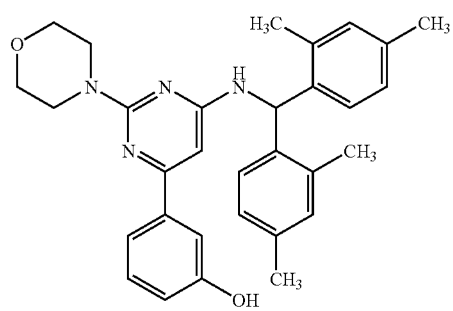 | 3-(6-{[bis(2,4-dimethylphenyl)methyl]amino}-2-morpholin-4-ylpyrimidin-4-yl)phenol | 495.6 |
| 97 | 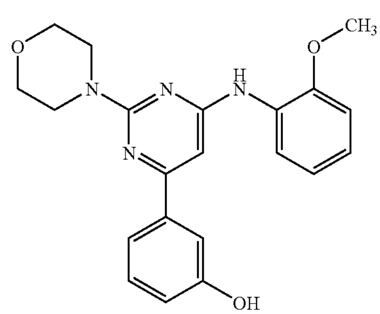 | 3-{6-[(2-methoxyphenyl)amino]-2-morpholin-4-ylpyrimidin-4-yl}phenol | 379.4 |

-continued

| Example | Structure | Name | LC/MS m/z (MH+) |
|---|---|---|---|
| 98 | 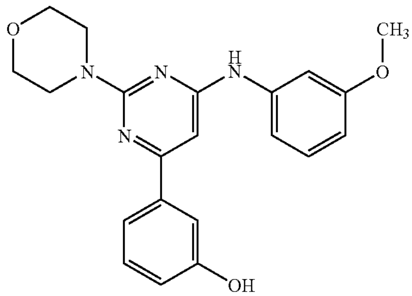 | 3-{6-[(3-methoxyphenyl)amino]-2-morpholin-4-ylpyrimidin-4-yl}phenol | 379.4 |
| 99 | 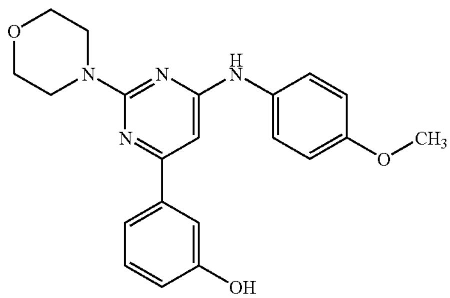 | 3-{6-[(4-methoxyphenyl)amino]-2-morpholin-4-ylpyrimidin-4-yl}phenol | 379.4 |
| 100 | 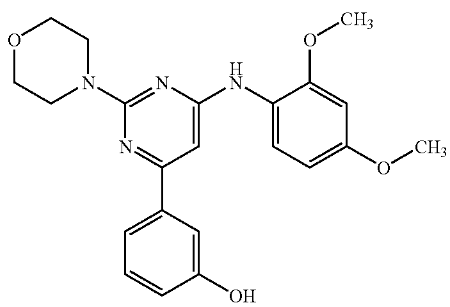 | 3-{6-[(2,4-dimethoxyphenyl)amino]-2-morpholin-4-ylpyrimidin-4-yl}phenol | 409.5 |
| 101 | 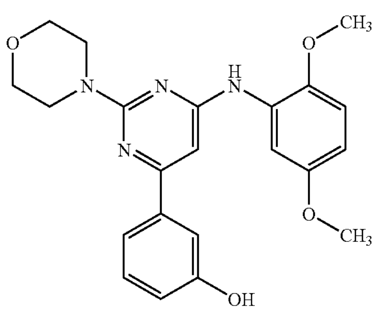 | 3-{6-[(2,5-dimethoxyphenyl)amino]-2-morpholin-4-ylpyrimidin-4-yl}phenol | 409.5 |
| 102 | 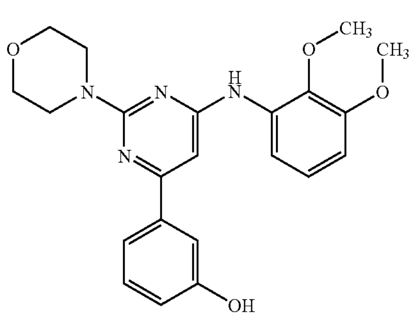 | 3-{6-[(2,3-dimethoxyphenyl)amino]-2-morpholin-4-ylpyrimidin-4-yl}phenol | 409.5 |

-continued

| Example | Structure | Name | LC/MS m/z (MH+) |
|---|---|---|---|
| 103 | 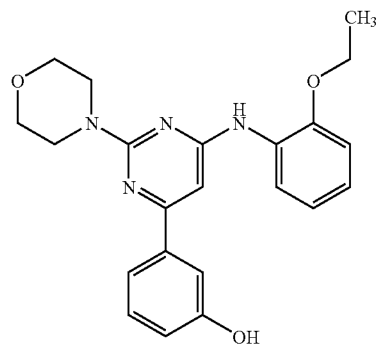 | 3-{6-[(2-ethoxyphenyl)amino]-2-morpholin-4-ylpyrimidin-4-yl}phenol | 393.5 |
| 104 | 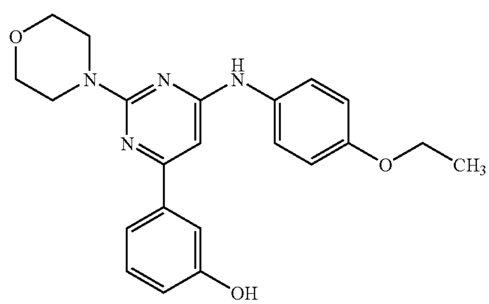 | 3-{6-[(4-ethoxyphenyl)amino]-2-morpholin-4-ylpyrimidin-4-yl}phenol | 393.5 |
| 105 | 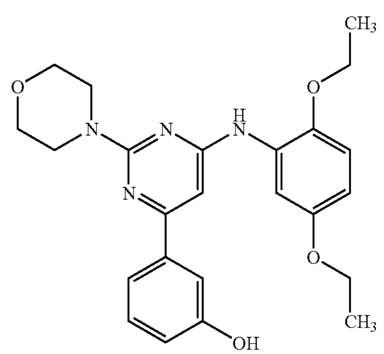 | 3-{6-[(2,5-diethoxyphenyl)amino]-2-morpholin-4-ylpyrimidin-4-yl}phenol | 437.5 |
| 106 | 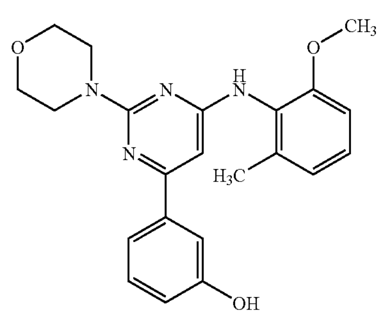 | 3-{6-[(2-methoxy-6-methylphenyl)amino]-2-morpholin-4-ylpyrimidin-4-yl}phenol | 393.5 |

-continued

| Example | Name | LC/MS m/z (MH+) |
|---|---|---|
| 107 | 3-{2-morpholin-4-yl-6-[(3-phenoxyphenyl)amino]pyrimidin-4-yl}phenol | 441.5 |
| 108 | 3-{2-morpholin-4-yl-6-[(4-phenoxyphenyl)amino]pyrimidin-4-yl}phenol | 441.5 |
| 109 | 3-(6-{[3-(benzyloxy)phenyl]amino}-2-morpholin-4-ylpyrimidin-4-yl)phenol | 455.5 |
| 110 | 3-{6-[(4-methoxydibenzo[b,d]furan-3-yl)amino]-2-morpholin-4-ylpyrimidin-4-yl}phenol | 469.5 |

| Example | Structure | Name | LC/MS m/z (MH+) |
|---|---|---|---|
| 111 | 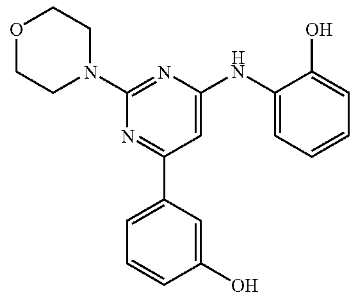 | 2-{[6-(3-hydroxyphenyl)-2-morpholin-4-ylpyrimidin-4-yl]amino}phenol | 365.4 |
| 112 | 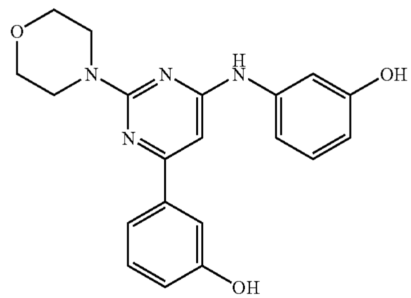 | 3-{6-[(3-hydroxyphenyl)amino]-2-morpholin-4-ylpyrimidin-4-yl}phenol | 365.4 |
| 113 | 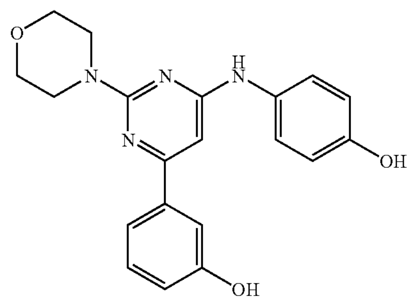 | 3-{6-[(4-hydroxyphenyl)amino]-2-morpholin-4-ylpyrimidin-4-yl}phenol | 365.4 |
| 114 | 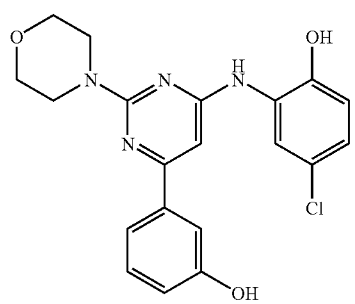 | 4-chloro-2-{[6-(3-hydroxyphenyl)-2-morpholin-4-ylpyrimidin-4-yl]amino}phenol | 399.8 |
| 115 | 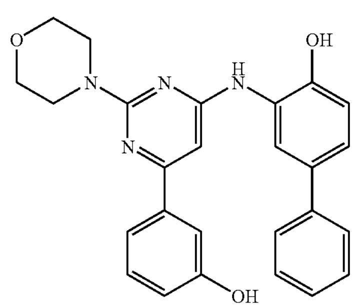 | 3-{[6-(3-hydroxyphenyl)-2-morpholin-4-ylpyrimidin-4-yl]amino}-1,1'-biphenyl-4-ol | 441.5 |

-continued
| Example | Structure | Name | LC/MS m/z (MH+) |
|---|---|---|---|
| 116 | 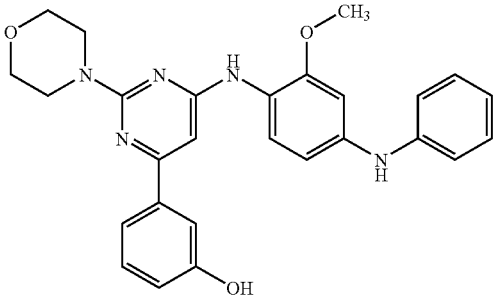 | 3-{6-[(4-anilino-2-methoxyphenyl)amino]-2-morpholin-4-ylpyrimidin-4-yl}phenol | 470.5 |
| 117 | 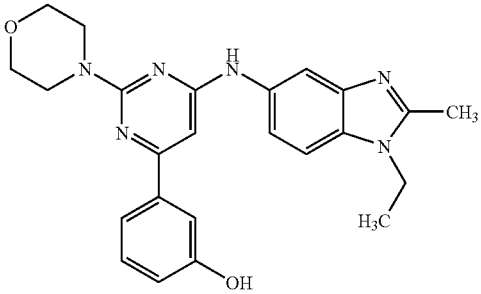 | 3-{6-[(1-ethyl-2-methyl-1H-benzimidazol-5-yl)amino]-2-morpholin-4-ylpyrimidin-4-yl}phenol | 431.5 |
| 118 | 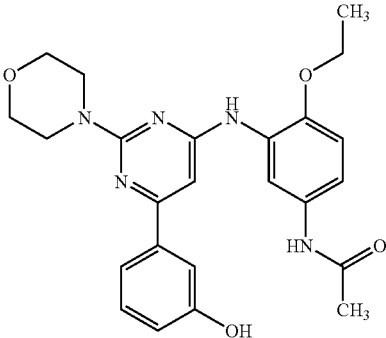 | N-(4-ethoxy-3-{[6-(3-hydroxyphenyl)-2-morpholin-4-ylpyrimidin-4-yl]amino]phenyl)acetamide | 450.5 |
| 119 | 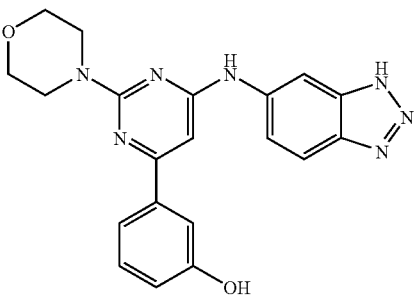 | 3-[6-(1H-1,2,3-benzotriazol-6-ylamino)-2-morpholin-4-ylpyrimidin-4-yl]phenol | 390.4 |

| Example | Structure | Name | LC/MS m/z (MH+) |
|---|---|---|---|
| 120 | 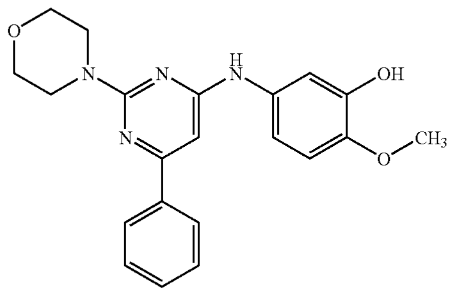 | 2-methoxy-5-[(2-morpholin-4-yl-6-phenylpyrimidin-4-yl)amino]phenol | 379.4 |
| 121 | 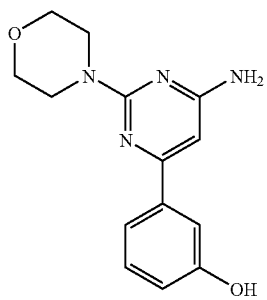 | 3-(6-amino-2-morpholin-4-ylpyrimidin-4-yl)phenol | 273.3 |
| 122 | 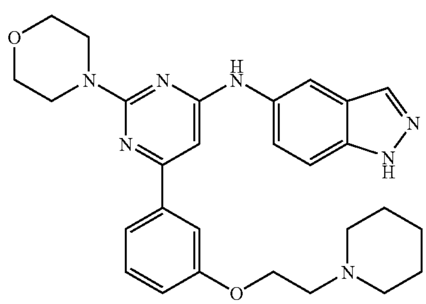 | N-{2-morpholin-4-yl-6-[3-(2-piperidin-1-ylethoxy)phenyl]pyrimidin-4-yl}-1H-indazol-5-amine | 500.6 |
| 123 | 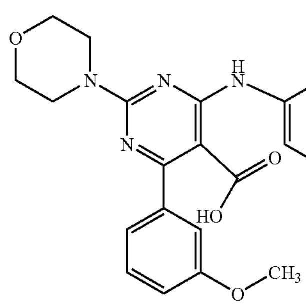 | 4-(3-methoxyphenyl)-2-morpholin-4-yl-6-(pyridin-3-ylamino)pyrimidine-5-carboxylic acid | 408.4 |

-continued

| Example | Structure | Name | LC/MS m/z (MH+) |
|---|---|---|---|
| 124 | 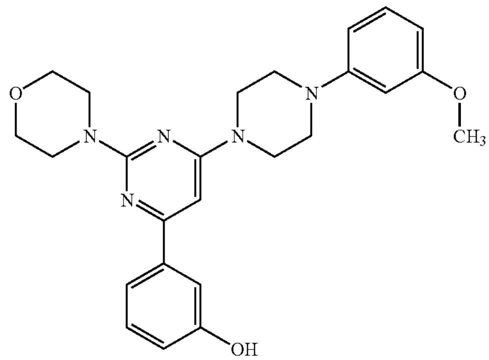 | 3-{6-[4-(3-methoxyphenyl)piperazin-1-yl]-2-morpholin-4-ylpyrimidin-4-yl}phenol | 448.5 |
| 125 | 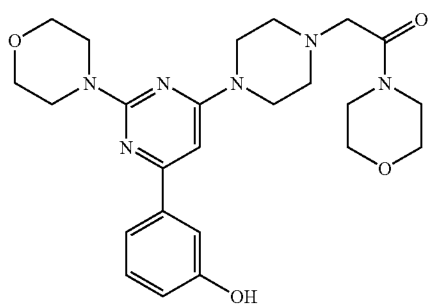 | 3-{2-morpholin-4-yl-6-[4-(2-morpholin-4-yl-2-oxoethyl)piperazin-1-yl]pyrimidin-4-yl}phenol | 469.6 |
| 126 | 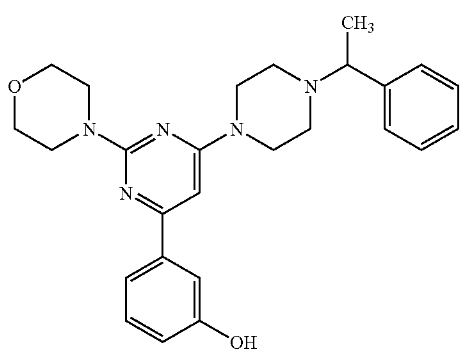 | 3-{2-morpholin-4-yl-6-[4-(1-phenylethyl)piperazin-1-yl]pyrimidin-4-yl}phenol | 446.6 |
| 127 | 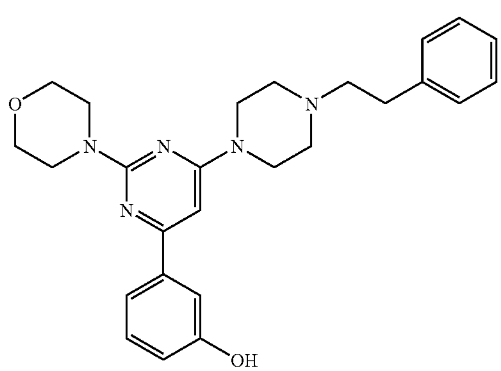 | 3-{2-morpholin-4-yl-6-[4-(2-phenylethyl)piperazin-1-yl]pyrimidin-4-yl}phenol | 446.6 |

-continued

| Example | Structure | Name | LC/MS m/z (MH+) |
|---|---|---|---|
| 128 | 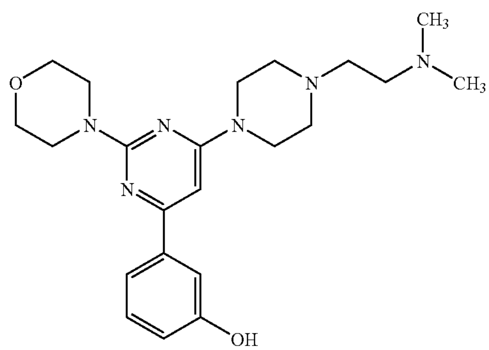 | 3-(6-{4-[2-(dimethylamino)ethyl]piperazin-1-yl}-2-morpholin-4-ylpyrimidin-4-yl)phenol | 413.5 |
| 129 | 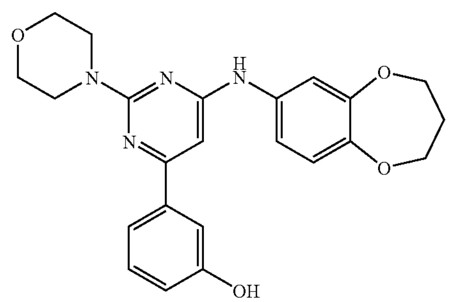 | 3-[6-(3,4-dihydro-2H-1,5-benzodioxepin-7-ylamino)-2-morpholin-4-ylpyrimidin-4-yl]phenol | 421.5 |
| 130 | 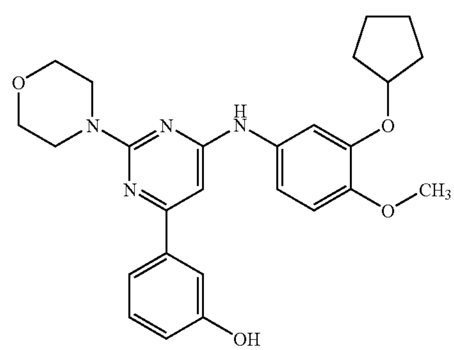 | 3-(6-{[3-(cyclopentyloxy)-4-methoxyphenyl]amino}-2-morpholin-4-ylpyrimidin-4-yl)phenol | 463.5 |
| 131 | 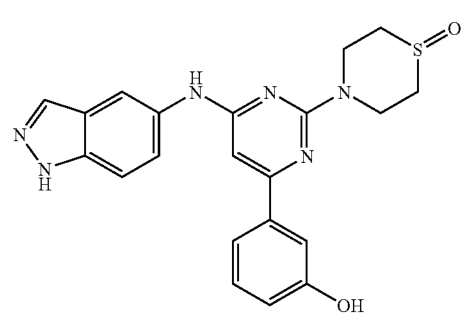 | 3-[6-(1H-indazol-5-ylamino)-2-(1-oxidothiomorpholin-4-yl)pyrimidin-4-yl]phenol | 421.5 |

| Example | Name | LC/MS m/z (MH+) |
|---|---|---|
| 132 | 3-[2-(2,6-dimethylmorpholin-4-yl)-6-(1H-indazol-5-ylamino)pyrimidin-4-yl]phenol | 417.5 |
| 133 | 5-{[6-(3-hydroxyphenyl)-2-morpholin-4-ylpyrimidin-4-yl]amino}pyridin-2-ol | 366.4 |
| 134 | 6-(3-fluorophenyl)-2-morpholin-4-yl-N-pyridin-3-ylpyrimidin-4-amine | 352.4 |
| 135 | 2-morpholin-4-yl-N-pyridin-3-yl-6-[3-(trifluoromethyl)phenyl]pyrimidin-4-amine | 402.4 |
| 136 | 6-(3-methoxyphenyl)-2-morpholin-4-yl-N-pyridin-3-ylpyrimidin-4-amine | 364.4 |

-continued

| Example | Structure | Name | LC/MS m/z (MH+) |
|---|---|---|---|
| 137 | 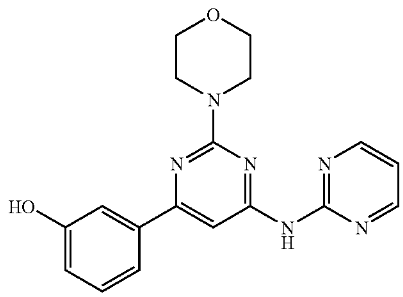 | 3-[2-morpholin-4-yl-6-(pyrimidin-2-ylamino)pyrimidin-4-yl]phenol | 351.4 |
| 138 | 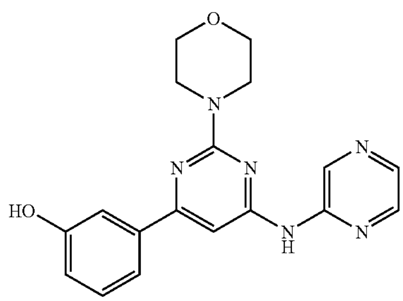 | 3-[2-morpholin-4-yl-6-(pyrazin-2-ylamino)pyrimidin-4-yl]phenol | 351.4 |
| 139 | 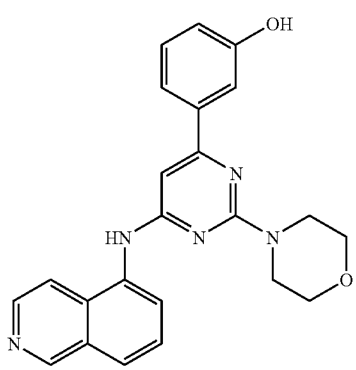 | 3-[6-(isoquinolin-5-ylamino)-2-morpholin-4-ylpyrimidin-4-yl]phenol | 400.5 |
| 140 | 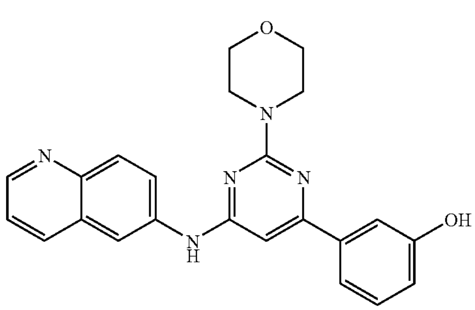 | 3-[2-morpholin-4-yl-6-(quinolin-6-ylamino)pyrimidin-4-yl]phenol | 400.5 |

| Example | Structure | Name | LC/MS m/z (MH+) |
|---|---|---|---|
| 141 | 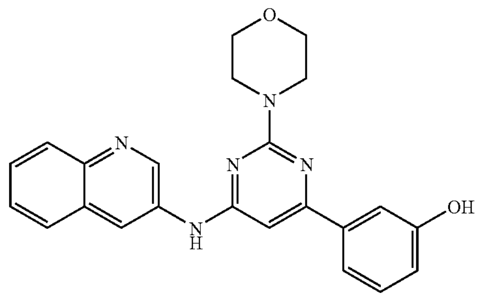 | 3-[2-morpholin-4-yl-6-(quinolin-3-ylamino)pyrimidin-4-yl]phenol | 400.5 |
| 142 | 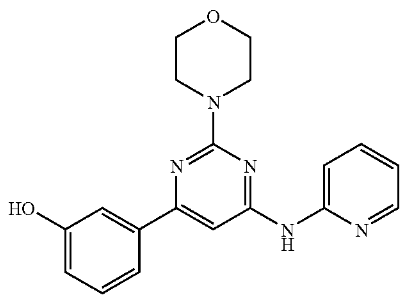 | 3-[2-morpholin-4-yl-6-(pyridin-2-ylamino)pyrimidin-4-yl]phenol | 350.4 |
| 143 | 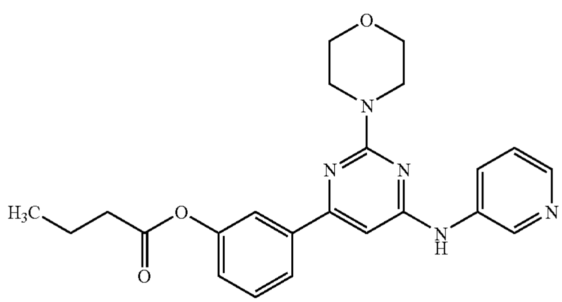 | 3-[2-morpholin-4-yl-6-(pyridin-3-ylamino)pyrimidin-4-yl]phenyl butyrate | 420.5 |
| 144 | 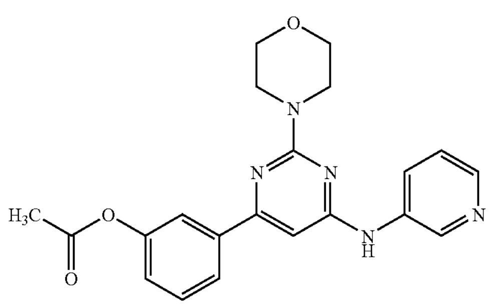 | 3-[2-morpholin-4-yl-6-(pyridin-3-ylamino)pyrimidin-4-yl]phenyl acetate | 392.4 |
| 145 | 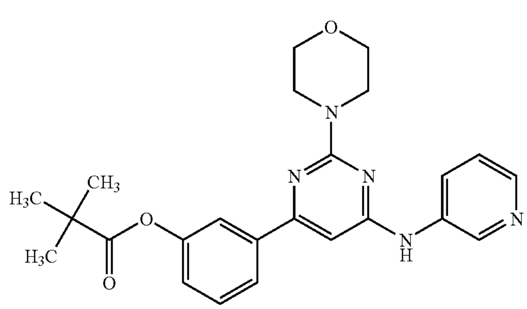 | 3-[2-morpholin-4-yl-6-(pyridin-3-ylamino)pyrimidin-4-yl]phenyl pivalate | 434.5 |

-continued

| Example | Structure | Name | LC/MS m/z (MH+) |
|---|---|---|---|
| 146 | 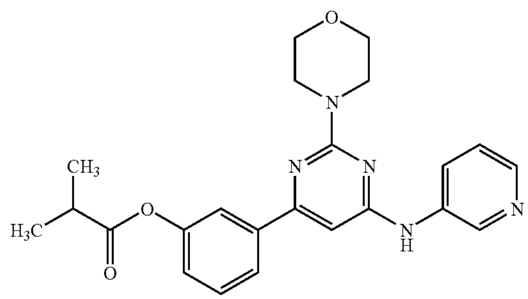 | 3-[2-morpholin-4-yl-6-(pyridin-3-ylamino)pyrimidin-4-yl]phenyl 2-methylpropanoate | 420.5 |
| 147 | 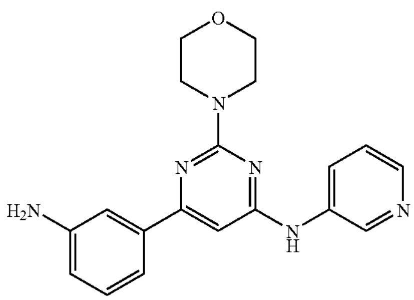 | 6-(3-aminophenyl)-2-morpholin-4-yl-N-pyridin-3-ylpyrimidin-4-amine | 349.4 |
| 148 | 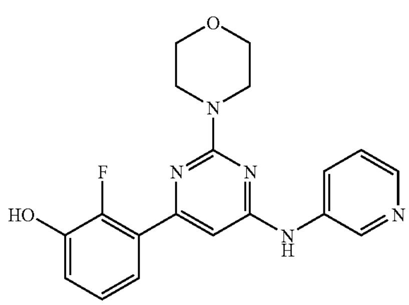 | 2-fluoro-3-[2-morpholin-4-yl-6-(pyridin-3-ylamino)pyrimidin-4-yl]phenol | 368.4 |
| 149 | 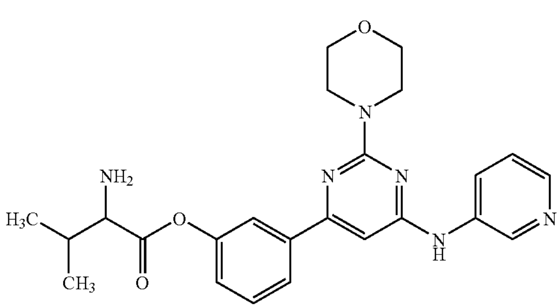 | 3-[2-morpholin-4-yl-6-(pyridin-3-ylamino)pyrimidin-4-yl]phenyl valinate | 449.5 |

-continued
| Example | Structure | Name | LC/MS m/z (MH+) |
|---|---|---|---|
| 150 | 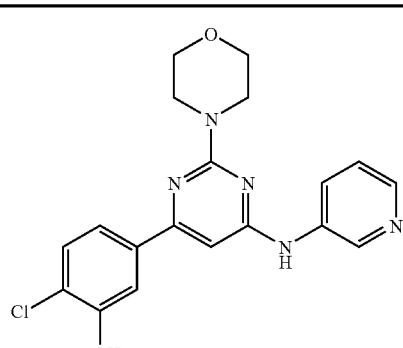 | 2-chloro-5-[2-morpholin-4-yl-6-(pyridin-3-ylamino)pyrimidin-4-yl]phenol | 384.8 |
| 151 | 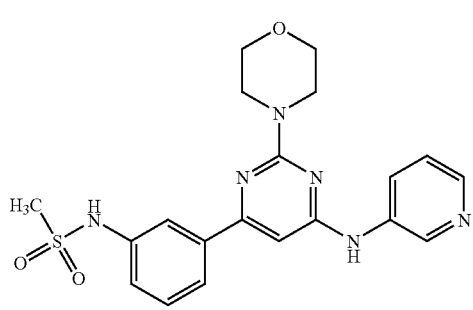 | N-{3-[2-morpholin-4-yl-6-(pyridin-3-ylamino)pyrimidin-4-yl]phenyl}methanesulfonamide | 427.5 |
| 152 | 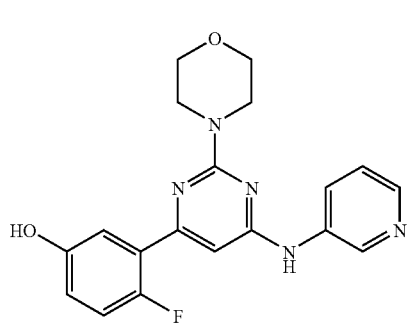 | 4-fluoro-3-[2-morpholin-4-yl-6-(pyridin-3-ylamino)pyrimidin-4-yl]phenol | 368.4 |
| 153 | 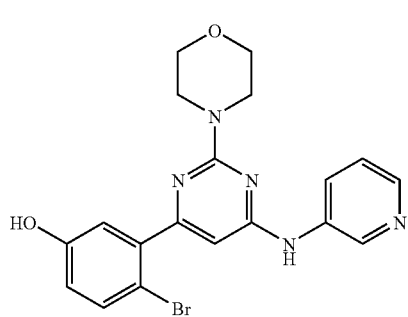 | 4-bromo-3-[2-morpholin-4-yl-6-(pyridin-3-ylamino)pyrimidin-4-yl]phenol | 429.3 |

| Example | Structure | Name | LC/MS m/z (MH+) |
|---|---|---|---|
| 154 | 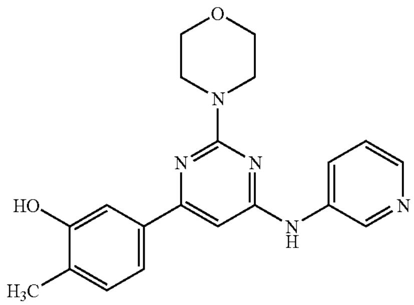 | 2-methyl-5-[2-morpholin-4-yl-6-(pyridin-3-ylamino)pyrimidin-4-yl]phenol | 364.4 |
| 155 | 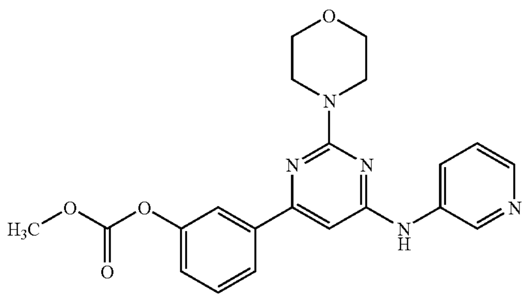 | methyl 3-[2-morpholin-4-yl-6-(pyridin-3-ylamino)pyrimidin-4-yl]phenyl carbonate | 408.4 |
| 156 | 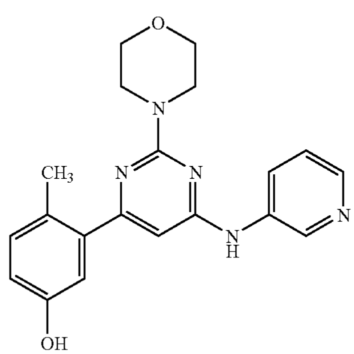 | 4-methyl-3-[2-morpholin-4-yl-6-(pyridin-3-ylamino)pyrimidin-4-yl]phenol | 364.4 |
| 157 | 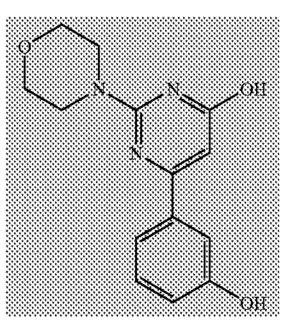 | 6-(3-hydroxyphenyl)-2-morpholin-4-ylpyrimidin-4-ol | 274.3 |

-continued
| Example | Structure | Name | LC/MS m/z (MH+) |
|---|---|---|---|
| 158 | 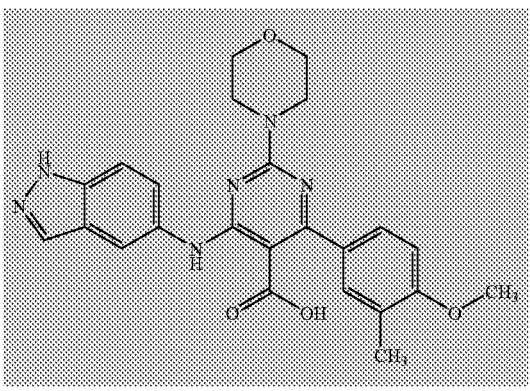 | 4-(1H-indazol-5-ylamino)-6-(4-methoxy-3-methylphenyl)-2-morpholin-4-ylpyrimidine-5-carboxylic acid | 461 |
| 159 | 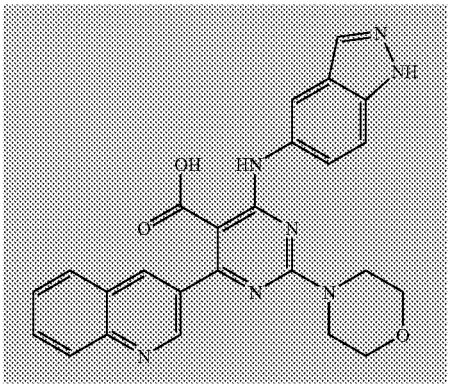 | 4-(1H-indazol-5-ylamino)-2-morpholin-4-yl-6-quinolin-3-ylpyrimidine-5-carboxylic acid | 468 |
| 160 | 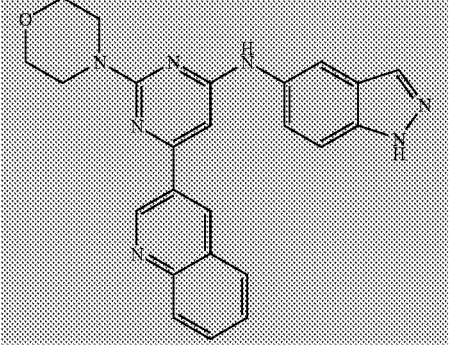 | N-(2-morpholin-4-yl-6-quinolin-3-ylpyrimidin-4-yl)-1H-indazol-5-amine | 424 |
| 161 | 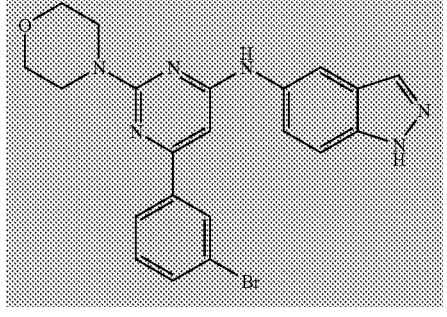 | N-[6-(3-bromophenyl)-2-morpholin-4-ylpyrimidin-4-yl]-1H-indazol-5-amine | 452 |

Example 162

4-Substituted Pyrimidinyl Compounds

Modifications in the 4-position of the pyrimidinyl core can be accomplished starting from the 4-ester moiety, as shown in Scheme 1 below. The ester 1 can be reduced to the alcohol 2 and then reoxydized to the corresponding aldehyde 3. The aldehyde can be used as a substrate for reductive amination with primary or secondary amines to afford 4-alkyl (or dialkyl)aminomethyl substituted pyrimidines 4 (representative procedure given below). As an alternate route, alcohol 2 can be converted to a good leaving group such as mesylate, tosylate (5) triflate and the like, and reacted with suitable nucleophiles such as primary or secondary amines, alcohols, thiols. As an additional alternate route the ester can be hydrolyzed to the carboxylic acid, which can be easily coupled with a variety of primary and secondary amines to afford 4-amides 6. Reduction of the amide will afford the desired 4-alkyl (or dialkyl)aminomethyl substituted pyrimidines 4 (see scheme 1). Compound 1 and its analogs can be obtained via Knoevenagel condensation of suitable aldehydes with ethyl acetoacetate, followed by oxidation of the dihydropyrimidine core with DDQ, with a procedure essentially identical to the one used in the solid phase synthesis of this class of compounds (other known agents e.g. CAN, can also be used in the aromatization step).

General procedure for the synthesis of {[6-(3-methoxyphenyl)-2-morpholin-4-yl-4-(3-pyridylamino) pyrimidin-5-yl]methyl}dialkylamines

[6-(3-methoxyphenyl)-2-morpholin-4-yl-4-(3-pyridylamino) pyrimidin-5-yl]formaldehyde (3)

Ester 1 is suspended in THF and DIBALH (1.6 N solution in THF, 3 eq) is added dropwise via a syringe. The reaction mixture is stirred at 50° C. overnight, then cooled down to room temperature and quenched with water. Product 2 precipitates and is filtered off, dried and used as is in the following step. Alcohol 2 is dissolved in DMA, and $MnO_2$ (xs) is added. The reaction mixture is stirred at room temperature overnight, and the solid is filtered off. The resulting clear solution is concentrated distilling off the solvent under reduced pressure and water is added. The precipitate thus obtained is filtered off, triturated with more water and dried, obtaining aldehyde 3, which is not purified further.

{[6-(3-methoxyphenyl)-2-morpholin-4-yl-4-(3-pyridylamino) pyrimidin-5-yl]methyl}dialkylamines (4)

A mixture of aldehyde 3 (1 eq), the desired amine (2.5-3 eq), and $NaCNBH_3$ in MeOH is refluxed overnight. The reac-

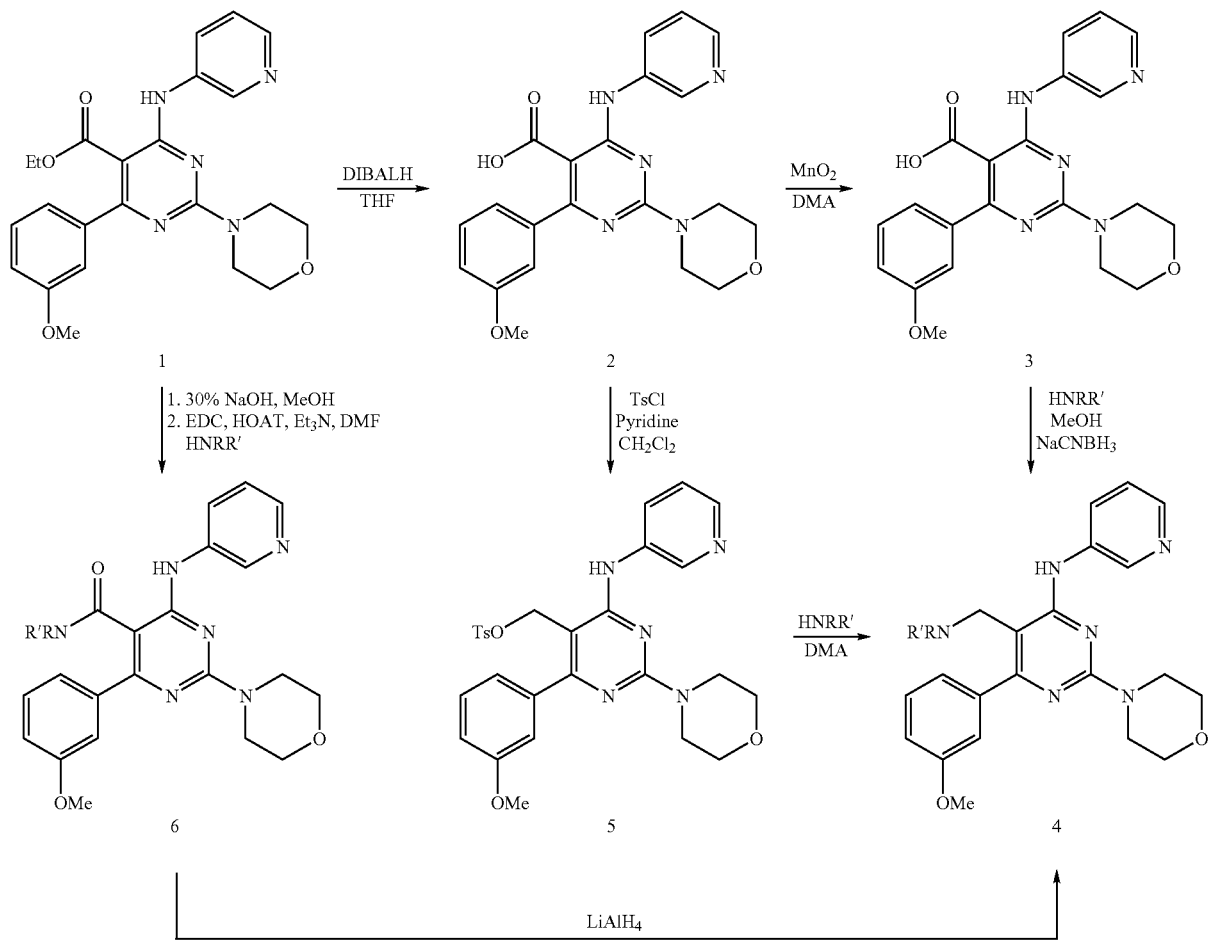

Scheme 1 tion mixture is cooled down to room temperature and 2N aq Na₂CO₃ solution is added. The mixture is stirred for 1 h and extracted several times with chloroform. The organic extracts are collected and dried (Na₂SO₄). Evaporation of the solvent and purification of the residue by reverse phase preparatory HPLC affords the desired compounds 4.

Example 163

Pyrimidinyl Compounds Having Carbon-Carbon Linkages at Position 2

The use of diverse amidines in the cyclization reaction with suitably substituted benzoylacetates can afford pyrimidines bearing a carbon-carbon linkage in position 2. Some examples are depicted in Schemes 2 and 3 below. The desired amidines are either commercially available or can be obtained from available precursors through procedures known by one skilled in the art.

6-(3-methoxyphenyl)-2-(2-morpholin-4-yl-2-oxoethyl)-3-hydropyrimidin-4-one (8)

In a round bottom flask, oven dried and kept under N₂, Cs₂CO₃ (1.5 eq) is suspended in dry DMF. 3-morpholin-4-yl-3-oxopropanamidine hydrochloride (1.2 eq) is added, followed by ethyl ethyl 3-(3-methoxyphenyl)-3-oxopropanoate 7 (1 eq). The reaction mixture is stirred at 115° C. overnight, then cooled down to room temperature. The DMF is distilled off under reduced pressure and the residue is dissolved in water, neutralizing with 5% HCl solution. The aqueous phase is then extracted with CH₂Cl₂ (×5). The organic extracts are collected and dried (Na₂SO₄). After evaporation of the solvent under reduced pressure the desired 6-(3-methoxyphenyl)-2-(2-morpholin-4-yl-2-oxoethyl)-3-hydropyrimidin-4-one 8 is obtained.

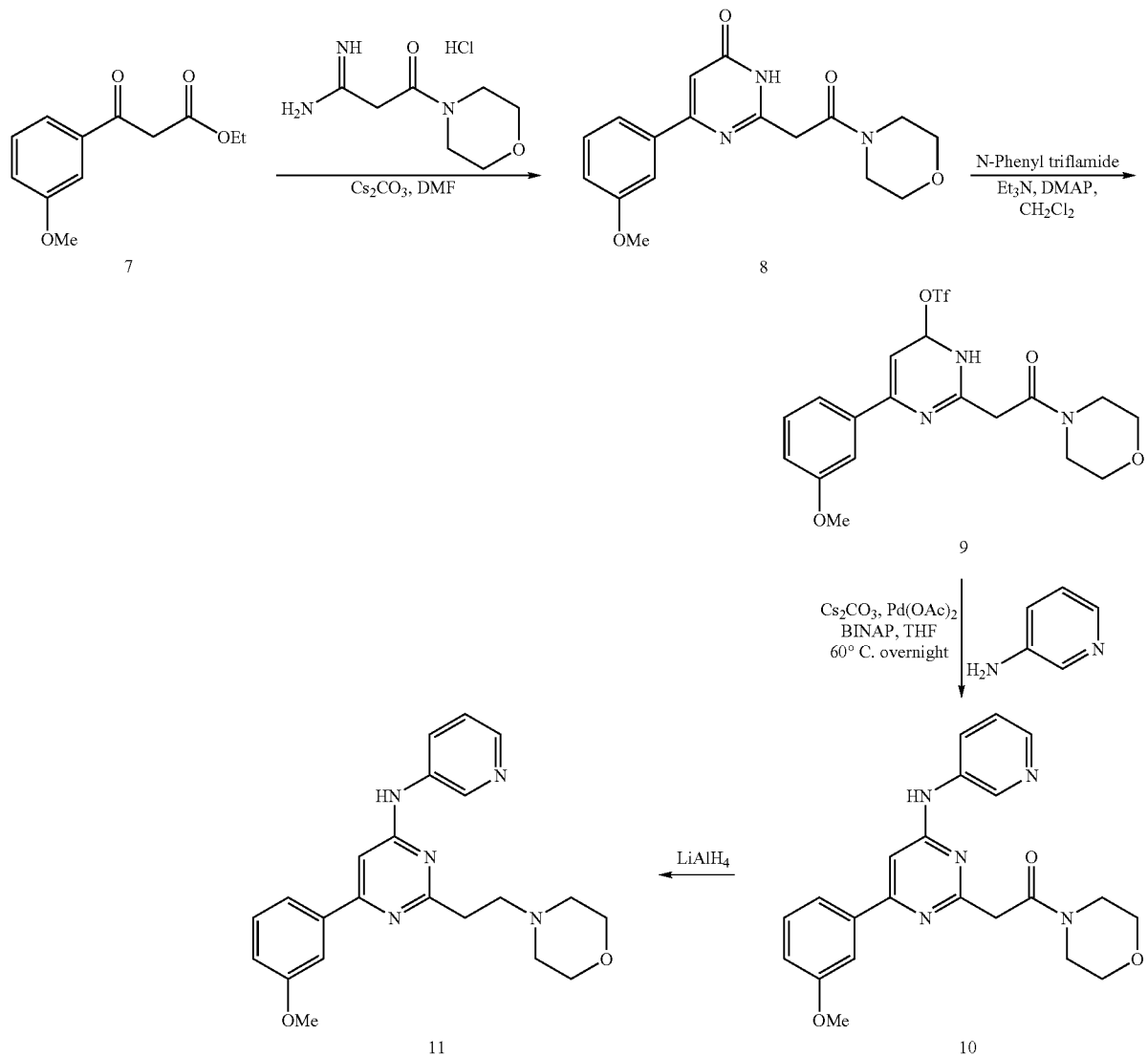

Scheme 2

6-(3-methoxyphenyl)-2-(2-morpholin-4-yl-2-oxoethyl)pyrimidin-4-yl (trifluoromethyl)sulfonate (9)

6-(3-methoxyphenyl)-2-(2-morpholin-4-yl-2-oxoethyl)-3-hydropyrimidin-4-one 8 (1 eq) is dissolved in CH$_2$Cl$_2$ in a round bottom flask, oven dried and kept under N$_2$. Triethylamine is added (1.4 eq) followed by N-Phenyl trifluoromethanesulfonimide (1.2 eq) and DMAP (10 mol %). The reaction mixture is stirred at room temperature overnight. The solvent is evaporated under reduced pressure and the residue purified by chromatography on silicagel (ethyl acetate/hexanes 1:5), obtaining the desired 6-(3-methoxyphenyl)-2-(2-morpholin-4-yl-2-oxoethyl)pyrimidin-4-yl (trifluoromethyl)sulfonate 9.

2-[6-(3-methoxyphenyl)-4-(3-pyridylamino)pyrimidin-2-yl]-1-morpholin-4-ylethan-1-one (10)

[6-(3-methoxyphenyl)-2-(2-morpholin-4-ylethyl)pyrimidin-4-yl]-3-pyridylamine (11)

A dry round bottom flask is charged with LiAlH$_4$ (4 eq), and dry THF is added. The suspension is cooled down to 0° C. and a solution of compound 10 in THF is added dropwise. The reaction mixture is stirred 4 h at room temperature then cooled down to 0° C. and quenched with water, followed by 10% NaOH and then water again. The mixture is stirred overnight and the solid is filtered off. The aqueous phase is extracted with CH$_2$Cl$_2$, the organic extracts are collected and dried (Na$_2$SO$_4$). After evaporation of the solvent under reduced pressure and purification by reverse phase preparatory HPLC [6-(3-methoxyphenyl)-2-(2-morpholin-4-ylethyl)pyrimidin-4-yl]-3-pyridylamine 11 is obtained.

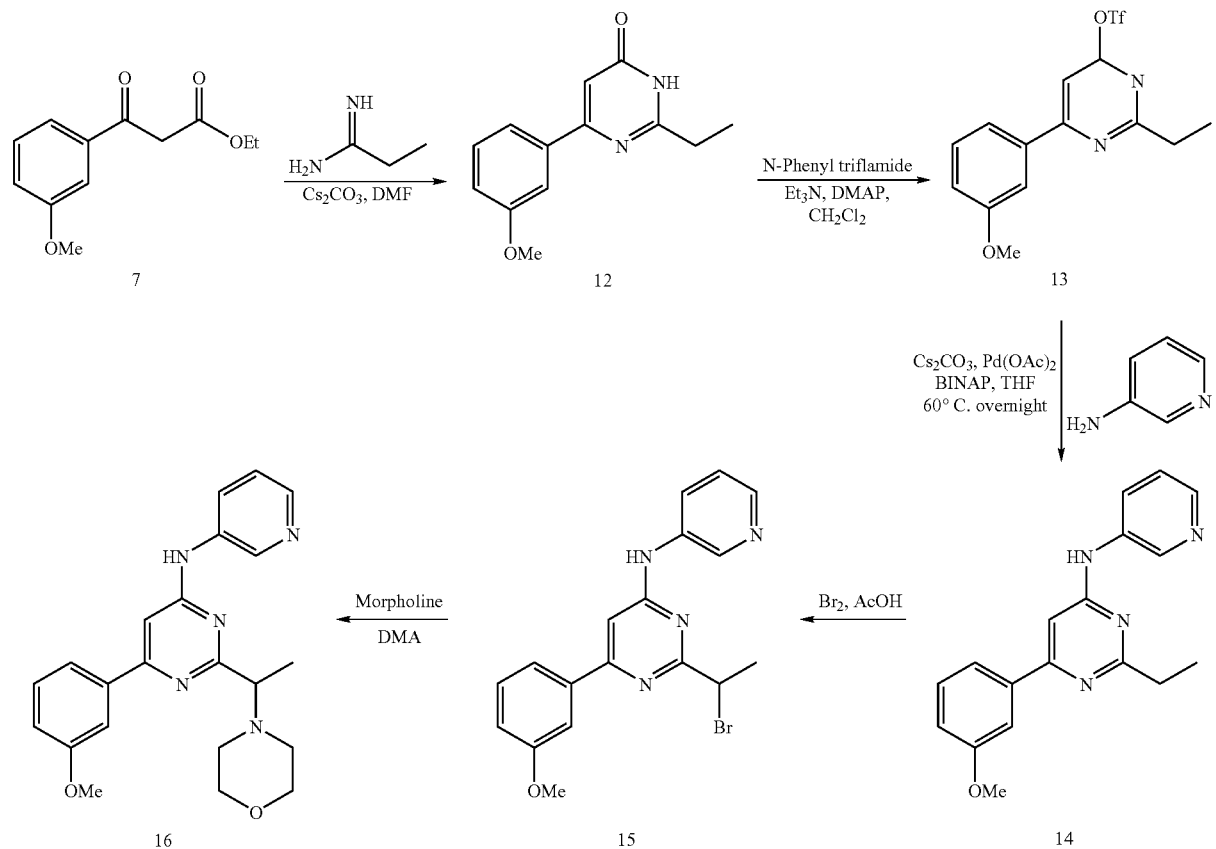

Scheme 3

A round bottom flask, oven dried and kept under N$_2$ atmosphere is charged with Cs$_2$CO$_3$ (1.4 eq), Pd(OAc)$_2$ (5 mol %), and S-(−)-BINAP (7.5 mol %). The flask is purged with N$_2$ for about 5-10 min and a solution of compound 9 (1 eq) in dry THF is added via a syringe, followed by 3-aminopyridine (2 eq) in one portion. The flask is equipped with a reflux condenser, purged again with N$_2$ for 5 min and the reaction mixture is refluxed overnight. The reaction mixture is cooled down to room temperature and the solvent is evaporated under reduced pressure. The residue is washed with water (×2) and triturated with methanol to afford the desired 2-[6-(3-methoxyphenyl)-4-(3-pyridylamino)pyrimidin-2-yl]-1-morpholin-4-ylethan-1-one 10.

[2-(bromoethyl)-6-(3-methoxyphenyl)pyrimidin-4-yl]-3-pyridylamine (15)

[2-ethyl-6-(3-methoxyphenyl)pyrimidin-4-yl]-3-pyridylamine 14 (synthesized with a procedure similar to the one previously described) (1 eq) is dissolved in acetic acid, then sodium acetate (2 eq) is added. To this mixture, a solution of bromine (1 eq) in acetic acid is added dropwise. The reaction is stirred at room temperature for 3 h. The reaction mixture is concentrated under reduced pressure, water is added and the solution basified (pH ~10-11) with sat. aq. Na$_2$CO$_3$ solution. The product 15 crashes out, is filtered off, dried, and used as is in the following step.

[6-(3-methoxyphenyl)-2-(morpholin-4-ylethyl)pyrimidin-4-yl]-3-pyridylamine (16)

Compound 15 (1 eq) is dissolved in 3 ml of dimethyl acetamide and morpholine (5 eq) is added. The reaction mixture is stirred at 60° C. for 4 h, then cooled down to room temperature. Water is added to the mixture and the crash out is filtered off, washed with water and purified by reverse phase preparatory HPLC, obtaining [6-(3-methoxyphenyl)-2-(morpholin-4-ylethyl)pyrimidin-4-yl]-3-pyridylamine 16.

Example 164

4-C and 4-O Substituted Pyrimidinyl Compounds

Substitution at the 4-position is not limited to an amino group, as described in Example 163. Position 4 can also bear an oxygen or a carbon linker. Ethers and 4-aryl, alkyl or 4-substituted alkyl pyrimidines can be obtained via standard procedures (i.e. SNAr, Mitsunobu, Suzuki, Stille, Heck and Sonogashira couplings) known to the one skilled in the art and exemplified by the following schemes 4 and 5.

($Na_2SO_4$) evaporated and purified by reverse phase preparatory HPLC, obtaining compound 18.

General procedure for the synthesis of 6-(3-methoxyphenyl)-2-morpholin-4-yl-4-Aryl (or heteroaryl) oxypyrimidines (20)

The desired hydroxy substituted aromatic or heteroaromatic compound (1 eq) and triflate 17 (1 eq) are dissolved in DMF, and solid $K_2CO_3$ (2 eq) is added in one portion. The reaction mixture is heated at 115° C. overnight. The reaction mixture is cooled down to room temperature, most of the DMF is distilled off and water is added to the residue to obtain a precipitate. The solid is filtered off, dried, and purified by reverse phase preparatory HPLC, obtaining compound 19. Ester 19 is dissolved in a mixture of EtOH and 30% NaOH (1:1) and the solution is heated at 60° C. overnight. The solution is cooled down to room temperature and concentrated. Purification by reverse phase preparatory HPLC affords compound 20.

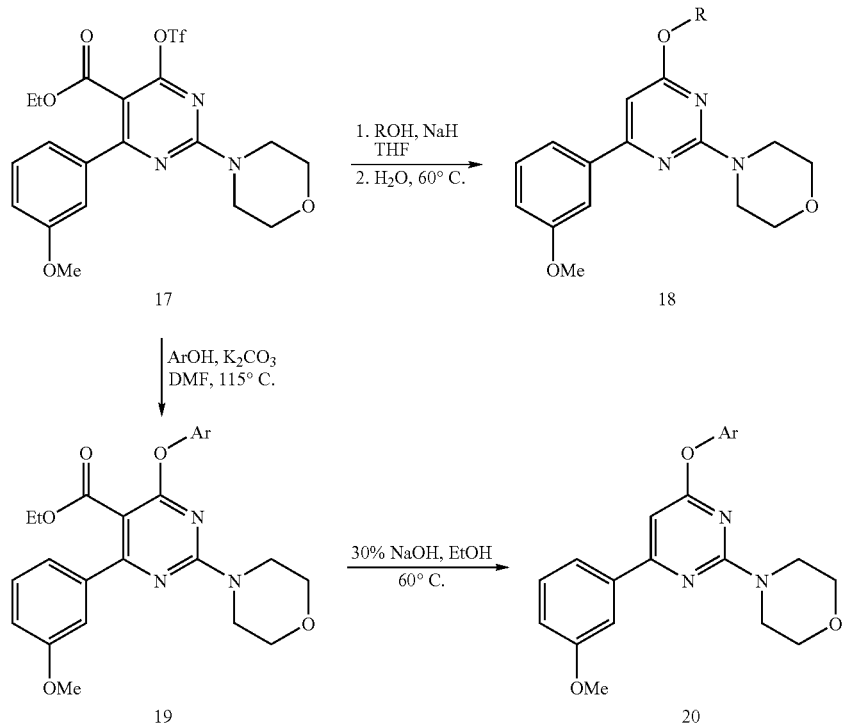

Scheme 4

General procedure for the synthesis of 4-Alkoxy-6-(3-methoxyphenyl)-2-morpholin-4-ylpyrimidines (18)

NaH (60% in mineral oil, ~1.2 eq) is suspended in dry NMP and the desired alcohol (1 eq) is added. The reaction mixture is stirred at room temperature for 1 h, then triflate 17 is added in one portion and the mixture heated at 100° C. for 2 h. The reaction is cooled down to room temperature, quenched with water, and heated at 60° C. The water is extracted with $CH_2Cl_2$, the organic extracts are dried General procedure for Suzuki couplings: Synthesis of 3-Methoxy-1-(2-morpholin-4-yl-6-aryl (or heteroaryl) pyrimidin-4-yl) benzenes (22)

A round bottom flask is charged with 2N $Na_2CO_3$ solution (4 eq) and THF and the mixture is sparged with $N_2$ through a dispersion tube. Triflate 21 (1 eq) and the desired boronic acid or boronate (1.2 eq) are subsequently added, followed by Pd(dppf)$_2$Cl$_2$ (2.5 mol %). The reaction mixture is refluxed overnight, cooled to room temperature and diluted with EtOAc. The two phases are separated, the organic phase is washed with 2N aq $Na_2CO_3$, brine, and dried ($Na_2SO_4$).

Evaporation of the solvent under reduced pressure, and purification by column chromatography on silicagel affords the desired product 22.

General Procedure for Sonogashira couplings: Synthesis of 3-Methoxy-1-(2-morpholin-4-yl-6-alkynyl pyrimidin-4-yl) benzenes (23)

A round bottom flask is charged with THF, and the solvent is sparged with nitrogen for 10 minutes, using a dispersion tube. The alkyne (1 eq), pyrrolidine (2 eq) and triflate 21 (1 eq) are added, while bubbling nitrogen through the solution. Pd[P(Ph)$_3$]$_4$ (2.5 mol %) is added last, and the sparging stopped. The flask is equipped with a reflux condenser and the reaction mixture is refluxed overnight under nitrogen, then cooled down to room temperature. The THF is evaporated, the residue is triturated with water and ether and purified by reverse phase preparatory HPLC to obtain product 23.

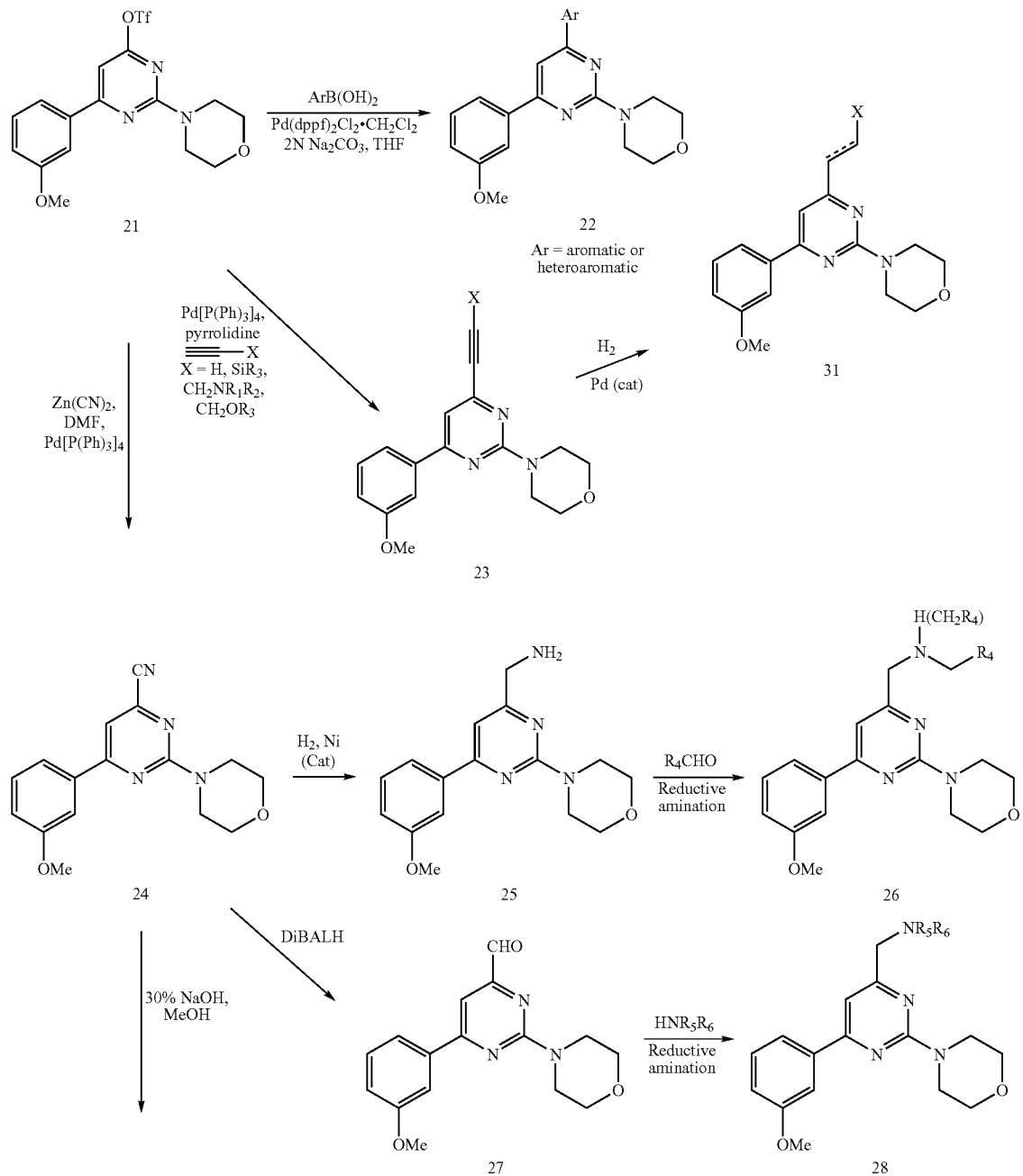

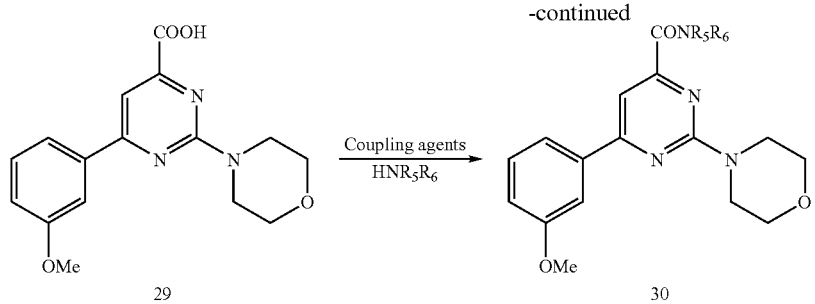

6-(3-methoxyphenyl)-2-morpholin-4-ylpyrimidine-4-carbonitrile (24)

A dry round bottom flask is charged with triflate 21 (1 eq) and zinc cyanide (2 eq), and DMF is added. Nitrogen is bubbled through the solution for 5 minutes and Pd[P(Ph)$_3$]$_4$ is added in one portion. The reaction mixture is stirred at 90° C. overnight. After cooling down to room temperature sat. NaHCO$_3$ is added, and the mixture extracted with EtOAc. The organic extracts are collected and dried (Na$_2$SO$_4$). Evaporation of the solvent under reduced pressure and purification by column chromatography on silicagel (10% methanol in methylene chloride) afforded the desired product 24.

6-(3-methoxyphenyl)-2-morpholin-4-ylpyrimidine-4-carboxylic acid (29)

Compound 24 is dissolved in a 1:1 mixture of EtOH and 30% aq. NaOH. The solution is heated to 100° C. for 2 h. The mixture is cooled down to room temperature, concentrated and neutralized with 1 N HCl. The precipitate thus formed is washed with water twice and dried, to afford the desired product 25.

Synthesis of N,N-disubstuituted[6-(3-methoxyphenyl)-2-morpholin-4-ylpyrimidin-4-yl]carboxamides (30)

Carboxylic acid 29 (1 eq) is suspended in DMF. Et$_3$N (2 eq) and the desired amine (1.3 eq) are added, followed by EDC (1.2 eq) and HOAT (1.2 eq). The reaction mixture is stirred at room temperature for 2 days. Water is added, and the mixture is extracted with EtOAc. The residue is purified by preparatory HPLC obtaining the desired product 30.

The above compounds can be modified further via synthetic methodologies known to the one skilled in the art. In compound 23 the triple bond can be completely or partially reduced under hydrogenation conditions by appropriate choice of the catalyst, such as Ni, 10% Pd/C, 5% Pd/C, or Lindlar catalyst. Nitrile 24 can be reduced under different conditions to the 4-aminomethylpyrimidine 25 or to aldehyde 27, which can be functionalized further capping with carboxylic acids (on 25) or via reductive aminations (on both 25 and 27) to afford a variety of 4-aminomethyl substituted pyrimidines.

Example 165

6-Substituted Pyrimidinyl Compounds

The group in position 6 can be subject to synthetic modifications after formation of an advanced intermediate, when aromatic 1,2- 1,3- and 1,4-dialdehydes are used as substrates in the Knoevenagel condensation step, as exemplified by Scheme 6. The formyl group can then be directly reduced to hydroxymethyl, or used as a handle for reductive aminations.

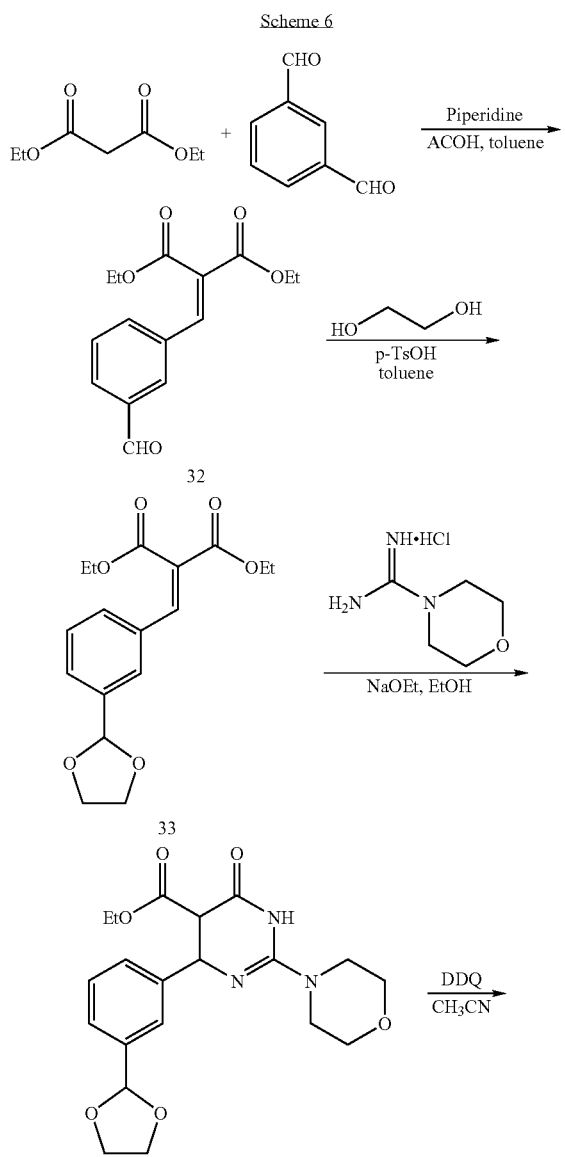

Scheme 6

-continued

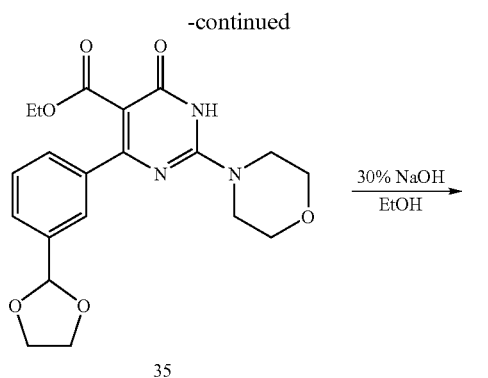
35

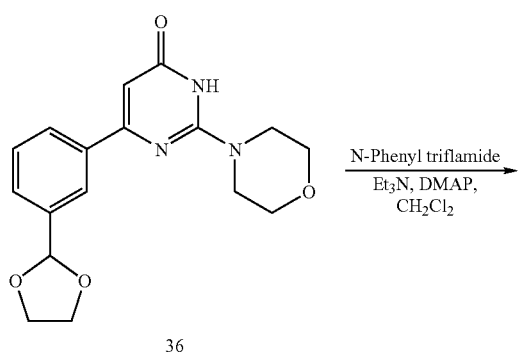
36

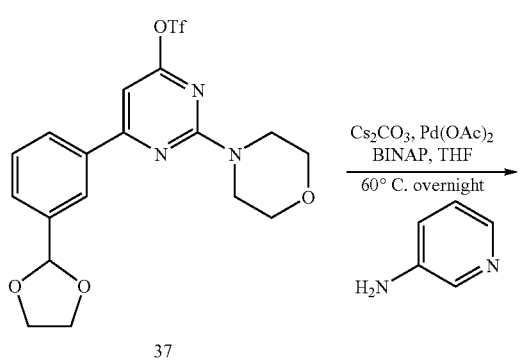
37

38

-continued

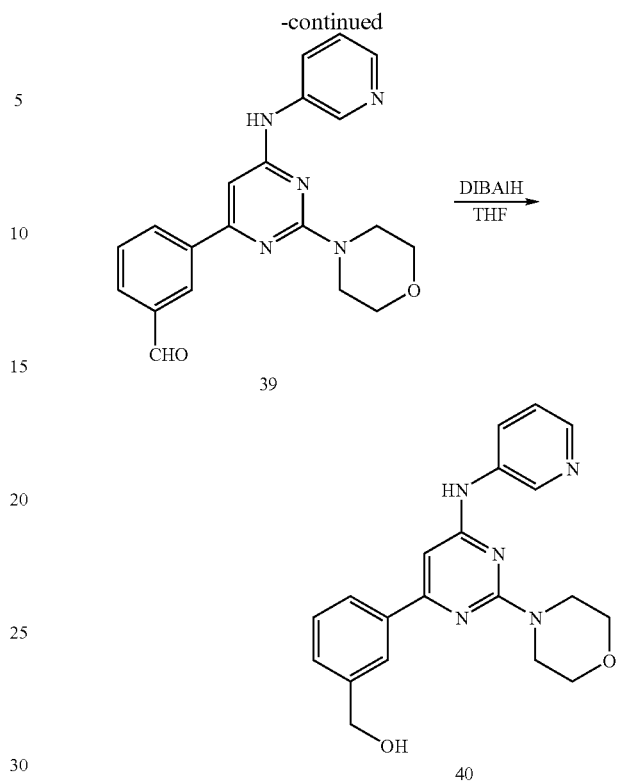
39

40

Diethyl 2-[(3-formylphenyl)methylene]propane-1,3-dioate (32)

Benzene 1,3 dicarbaldehyde (1 eq) is dissolved in toluene, and diethylmalonate (1 eq) is added, followed by piperidine (0.1 eq) and AcOH (0.1 eq). The flask is equipped with a Dean Stark trap and the reaction mixture is refluxed overnight. The reaction mixture is cooled down to room temperature, washed with water, 2% aq HCl, sat. aq NaHCO$_3$, brine, and dried. The solvent is evaporated under reduced pressure and the product 32 is isolated by column chromatography on silicagel.

Diethyl 2-[(3-(1,3-dioxolan-2-yl)phenyl)methylene]propane-1,3-dioate (33)

The solution of product 32 in toluene, from the previous reaction, is filtered, transferred to a round bottom flask, and ethylene glycol (2.4 eq) is added, followed by p-toulenesulfonic acid (0.5 eq). The reaction mixture is refluxed overnight with a Dean-Stark trap, then cooled down to room temperature, washed with sat. aq NaHCO$_3$, brine, and dried (Na$_2$SO$_4$). Product 33 is not purified further but used as is in the following step.

Ethyl 4-(3-(1,3-dioxolan-2-yl)phenyl)-6-morpholin-4-yl-2-oxo-1,3,4-trihydropyridine-3-carboxylate (34)

A dry round bottom flask is charged with dry EtOH, and Na (3 eq) is added. The reaction mixture is stirred till complete dissolution of Na, then morpholino carboxamidine hydrochloride (1.2 eq) is added, followed by compound 33 (1 eq). The reaction mixture is stirred at room temperature overnight. The solvent is removed under reduced pressure and water is added to the residue. The solid thus obtained is filtered, washed with water and dried, to afford crude 34 which is used in the next step without further purification.

4-(3-(1,3-Dioxolan-2-yl)phenyl)-6-morpholin-4-ylhydropyridin-2-one (36)

Substrate 34 (1 eq) is dissolved in $CH_3CN$. DDQ (1.2 eq) is added. The reaction mixture is stirred at room temperature overnight. The solvent is evaporated, and the residue purified by column chromatography on silicagel (10% MeOH in $CH_2Cl_2$) to obtain the desired ester 35, which undergoes hydrolysis and decarboxylation to 36 under conditions similar to the ones previously described for compound 20.

4-(3-(1,3-dioxolan-2-yl)phenyl)-6-morpholin-4-yl-2-pyridyl(trifluoromethyl)sulfonate (37)

The title compound is prepared following the same procedure as the one used for compound 9, described above.

[4-(3-(1,3-Dioxolan-2-yl)phenyl)-6-morpholin-4-yl(2-pyridyl)]-3-pyridylamine (38)

A round bottom flask, oven dried and kept under $N_2$ atmosphere is charged with $Cs_2CO_3$ (1.4 eq), $Pd(OAc)_2$ (5 mol %), and S-(−)-BINAP (7.5 mol %). The flask is purged with $N_2$ for about 5-10 min and a solution of compound 37 (1 eq) in dry THF is added via a syringe, followed by 3-aminopyridine (2 eq) in one portion. The flask is equipped with a reflux condenser, purged again with $N_2$ for 5 min and the reaction mixture is refluxed overnight. The reaction mixture is cooled down to room temperature and the solvent is evaporated under reduced pressure. The residue is washed with water (×2) and triturated with methanol to afford compound 38.

3-[2-morpholin-4-yl-6-(3-pyridylamino)-4-pyridyl]benzaldehyde (39)

Compound 38 was suspended in wet acetone and p-toluenesulfonic acid (0.2 eq) was added. The reaction mixture was refluxed overnight, then concentrated under reduced pressure. The residue was triturated with diethyl ether, water and MeOH to afford the desired aldehyde 39.

{3-[2-morpholin-4-yl-6-(3-pyridylamino)-4-pyridyl]phenyl}methan-1-ol (40)

Aldehyde 39 is suspended in THF and DIBALH (1.6 N solution in THF, 3 eq) is added dropwise via a syringe. The reaction mixture is stirred at room temperature overnight, then quenched with water. The aqueous phase is extracted repeatedly with EtOAc. The organic extracts are collected and dried ($Na_2SO_4$). Evaporation of the solvent under reduced pressure and purification by reverse phase preparatory HPLC, affords compound 40.

Substituents in position 6 can be varied using suitable aldehydes in the Knoevenagel step, as previously described. These substrates need not to be limited to aromatic aldehydes. The synthetic route can be extended to heteroaromatic, heterocyclic and aliphatic aldehydes. In particular, substituted phenylacetaldehydes (41, n=1) and 3-phenylpropionaldehydes (41, n=2), allow access to compounds such as 42 in which the substituted aromatic group is linked to the pyrimidine core by a single carbon or a 2 carbons spacer, as shown in Scheme 7.

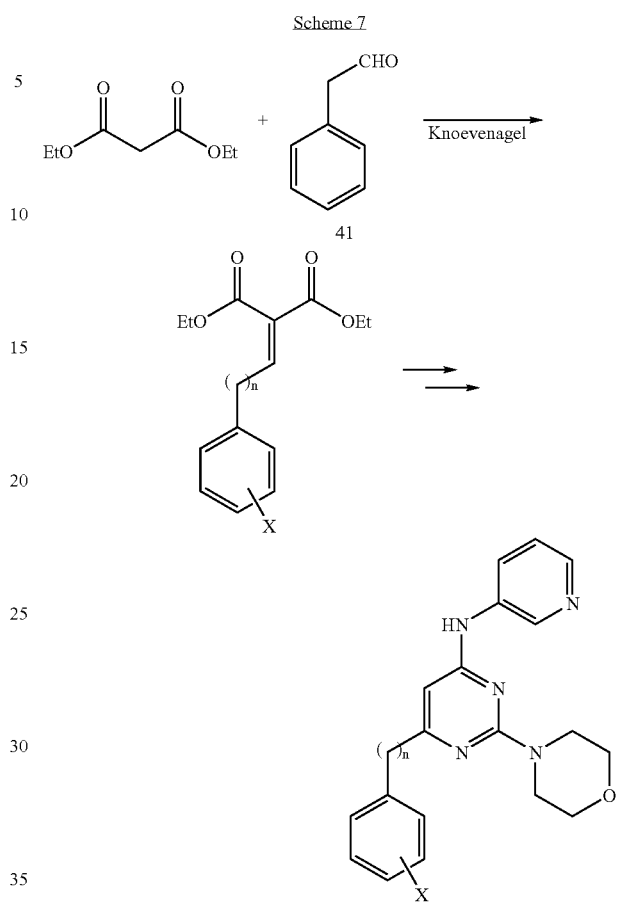

Example 166

PI3K Assay Procedures

Method 1: Homogenous Solution Phase Assay

Compounds to be tested are dissolved in DMSO and directly distributed to 384-well flashplates at 1.25 µL per well. To start the reaction, 20 µL of 6 nM PI3 kinase are added into each well followed by 20 µL of 400 nM ATP containing a trace of radio-labeled ATP and 900 nM 1-alpha-phosphatidylinositol (PI). The plates are briefly centrifuged to remove any air gap. The reaction is performed for 15 minutes and then stopped by the addition of 20 µL of 100 mM EDTA. The stopped reaction is incubated overnight at RT to allow the lipid substrate to bind by hydrophobic interaction to the surface of the flashplate. The liquid in the wells is then washed away, and the labeled substrate is detected with scintillation counting.

Method 2: One Step Solid Phase Assay

This method is similar to Method 1 except that the lipid substrate (1-alpha-phosphatidylinositol) is first dissolved in a coating buffer and incubated on flashplate at room temperature over night to allow the lipid substrate to bind by hydrophobic interaction to the surface of the flashplate. Unbound substrate is then washed away. On the day of assay, 20 µL of 6 nM PI3 kinase are added into each well followed by 20 μL of 400 nM ATP containing trace of radio-labeled ATP. Compounds are added together with enzyme and ATP to the lipid-coated plates. The plates are briefly centrifuged to remove any air gap. The reaction is performed for two to three hours. The reaction is stopped by addition of 20 μL of 100 mM EDTA or by immediate plate washing. Phosphorylated lipid substrate is detected with scintillation counting.

The compounds of Examples 11a, 13, 19, 34-49, 51-53, 55, 57-59, 61-64, 68, 71-76, 79, 81, 82, 85-87, 89-91, 118, 119, 121, 122, 124 and 133-156 displayed an $IC_{50}$ value of less than 20 μM with respect to PI3K when tested in the homogeneous solution assay (Method 1), as described above. The compounds of Examples 20, 21, 23, 47, 55-60, 62, 63, 65, 70, 71-75, 77-95, 97-120, 122-125, 127, 129, 130, 133, 137 and 143-155 displayed an $IC_{50}$ value of less than 20 μM with respect to PI3K when tested in the one step solid phase assay (Method 2), as described above.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the above disclosure.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the formula:

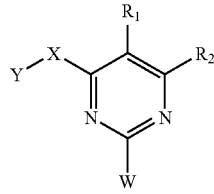

or a stereoisomer, tautomer, or pharmaceutically acceptable salt thereof, wherein $R_1$ is H;

$R_2$ is selected from the group consisting of substituted aryl and substituted heteroaryl, where said substituted heteroaryl is selected from the group consisting of a substituted pyridyl, a substituted pyrazinyl, a substituted pyrimidinyl, a substituted pyrrolyl, a substituted pyrazolyl, a substituted indazolyl, a substituted quinolinyl, and a substituted isoquinolinyl;

X is a direct bond;

Y is substituted or unsubstituted heterocyclyl; and

W is substituted and or unsubstituted morpholinyl.

2. The compound of claim 1, wherein said substituted aryl is a substituted phenyl.

3. The compound of claim 1, wherein said substituted aryl is hydroxy phenyl.

4. The compound of claim 1, wherein said substituted heteroaryl is a substituted pyridyl.

5. The compound of claim 1, wherein said unsubstituted heterocyclyl is selected from the group consisting of morpholinyl, pyrrolidinyl, imidazolidinyl, piperazinyl, piperidinyl, and diazepanyl.

6. The compound of claim 1, wherein said unsubstituted heterocyclyl is morpholinyl.

7. The compound of claim 1, wherein W is unsubstituted morpholinyl.

8. A composition, comprising a compound of claim 1 and a pharmaceutically acceptable carrier.

9. The composition of claim 8 further comprising at least one additional agent for the treatment of breast cancer.

10. The composition of claim 9, wherein the at least one additional agent for the treatment of breast cancer is selected from the group consisting of irinotecan, topotecan, gemcitabine, imatinib mesylate, herceptin, 5-fluorouracil, leucovorin, carboplatin, cisplatin, taxanes, tezacitabine, cyclophosphamide, vinca alkaloids, imatinib, anthracyclines, rituximab, tamoxifen, CPT 11, and trastuzumab.

11. A method for treating breast cancer comprising administering to a subject in need of such treatment an effective amount of a compound of claim 1.

12. The method of claim 11 further comprising administering to said subject at least one additional agent for the treatment of breast cancer.

13. The method of claim 12, wherein the at least one additional agent for the treatment of breast cancer is selected form the group consisting of irinotecan, topotecan, gemcitabine, imatinib mesylate, herceptin, 5-fluorouracil, leucovorin, carboplatin, cisplatin, taxanes, tezacitabine, cyclophosphamide, vinca alkaloids, imatinib, anthracyclines, rituximab, tamoxifen, CPT 11, and trastuzumab.

* * * * *